US006855725B2

(12) United States Patent
Bleisch et al.

(10) Patent No.: US 6,855,725 B2
(45) Date of Patent: Feb. 15, 2005

(54) EXCITATORY AMINO ACID RECEPTOR ANTAGONISTS

(75) Inventors: Thomas John Bleisch, Noblesville, IN (US); Sandra Ann Filla, Ashland, MA (US); Paul Leslie Ornstein, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/451,820

(22) PCT Filed: Dec. 20, 2001

(86) PCT No.: PCT/US01/45862

§ 371 (c)(1),
(2), (4) Date: Jun. 25, 2003

(87) PCT Pub. No.: WO02/053556

PCT Pub. Date: Jul. 11, 2002

(65) Prior Publication Data

US 2004/0063749 A1 Apr. 1, 2004

Related U.S. Application Data

(60) Provisional application No. 60/259,922, filed on Jan. 5, 2001.

(51) Int. Cl.[7] ..................... A61K 31/47; C07D 217/06; C07D 401/00
(52) U.S. Cl. ......................... 514/307; 546/147; 546/148
(58) Field of Search ................................ 546/147, 148; 514/307

(56) References Cited

U.S. PATENT DOCUMENTS

| 5,356,902 A | 10/1994 | Ornstein |
| 5,446,051 A | 8/1995 | Ornstein |
| 5,670,516 A | 9/1997 | Arnold et al. |
| 5,767,117 A | 6/1998 | Moskowitz |
| 6,579,886 B2 | 5/2003 | Bleakman et al. |
| 6,566,370 B1 | 6/2003 | Bell et al. |

FOREIGN PATENT DOCUMENTS

| EP | 0 590 789 | 4/1994 |
| WO | WO 98/45270 | 10/1998 |
| WO | WO 01/02367 | 1/2001 |

OTHER PUBLICATIONS

Neuropharmacology, 37, pp. 25–36 (1998), "Kainate GluR5 receptor subtype mediates the nociceptive response to formalin in the rat".
Neuropharmacology, 37, pp. 1211–1222 (1998), "Decahydroisoquinolines: novel competitive AMPA/kainite antagonists with neuroprotective effects in global cerebral ischaemia".
Y. Sahara, et al., "Glutamate Receptor Subunits GluR5 and KA–2 Are Coexpressed in Rat Trigeminal Ganglion Neurons," The Journal of Neuroscience, vol. 17, No. 17, pp. 6611–6620 (1997).
Z. Alam, et al., "Plasma levels of neuroexcitatory amino acids in patients with migraine or tension headache," Journal of Neurological Sciences, vol. 156, pp. 102–106 (1998).
Procter, et al., "Possible role of GluR54 glutamate receptors in spinal nociceptive processing in the anaesthetized rat," Journal of Physiology, 504.P, 101P–102P (1997).
Nikam, et al., The search for AMPA/Gly(N) receptor antagonists: Drugs of the Future, vol. 24, No. 10, pp. 1107–1124 (1999).
Proctor, et al., " Actions of kainite and AMPA selective glutamate receptor ligands on nociceptive processing in the spinal cord," Neuropharmacology, vol. 37, pp. 1287–1297 (1998).
Bleakman, et al., "Kainate receptor pharmacology and physiology," Cellular and Molecular Life Sciences, 56/7–8 (1999) 558–556.
National Library of Medicine (NLM), Bethesda, MD, US: Mitsilostas, et al., "Non–NMDA glutamate receptors modulate capsaicin induced c–fos expression within trigeminal nucleus caudalis," Database accession No. 10003939 & British Journal of Pharmacology, vol. 127, No. 3, pp. 623–630 (1999).

*Primary Examiner*—D. Margaret Seaman
(74) *Attorney, Agent, or Firm*—Alexander Wilson

(57) ABSTRACT

The present invention provides compounds of Formula I or Formula II, or the pharmaceutically acceptable salts or prodrugs thereof, pharmaceutical compositions comprising compounds or Formula I or Formula II, and methods for treating neurological disorders and neurodegenerative diseases, particularly migraine.

52 Claims, No Drawings

EXCITATORY AMINO ACID RECEPTOR ANTAGONISTS

This is the national phase application, under 35 USC 371, for PCT/US01/45862, filed 20 Dec. 2001, which claims the benefit under 35 USC 119(e), of U.S. provisional application Ser. No. 60/259,922, filed 05 Jan. 2001.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathways in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). Molecular biological studies have established that AMPA receptors are composed of subunits ($GluR_1$–$GluR_4$), which can assemble to form functional ion channels. Five kainate receptors have been identified which are classified as either High Affinity (KA1 and KA2) or Low Affinity (composed of $GluR_5$, $GluR_6$, and/or $GluR_7$ subunits). Bleakman et al., *Molecular Pharmacology*, 49, No.4, 581,(1996). The second general type of receptor is the G-protein coupled or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacol. Sci.*, 14, 13 (1993). Both types of excitatory amino acid receptor appear not only to mediate normal synaptic transmission along excitatory pathways, but also to participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of neurological disorders and conditions. The medical consequences of such neuronal degeneration makes the abatement of these degenerative neurological processes an important therapeutic goal. For instance, excitatory amino acid receptor excitotoxicity has been implicated in the pathophysiology of numerous neurological disorders, including the etiology of cerebral deficits subsequent to cardiac bypass surgery and grafting, stroke, cerebral ischemia, spinal cord lesions resulting from trauma or inflammation, perinatal hypoxia, cardiac arrest, and hypoglycemic neuronal damage. In addition, excitotoxicity has been implicated in chronic neurodegenerative conditions including Alzheimer's Disease, Huntington's Chorea, inherited ataxias, AIDS-induced dementia, amyotrophic lateral sclerosis, idiopathic and drug-induced Parkinson's Disease, as well as ocular damage and retinopathy. Other neurological disorders implicated with excitotoxicity and/or glutamate dysfunction include muscular spasticity including tremors, drug tolerance and withdrawal, brain edema, convulsive disorders including epilepsy, depression, anxiety and anxiety related disorders such as post-traumatic stress syndrome, tardive dyskinesia, and psychosis related to depression, schizophrenia, bipolar disorder, mania, and drug intoxication or addiction (see generally U.S. Pat. Nos. 5,446,051 and 5,670,516). Excitatory amino acid receptor antagonists may also be useful as analgesic agents and for treating or preventing various forms of headache, including cluster headache, tension-type headache, and chronic daily headache. In addition, published International Patent application WO 98/45720 reports that excitatory amino acid receptor excitotoxicity participates in the etiology of acute and chronic pain states including severe pain, intractable pain, neuropathic pain, post-traumatic pain.

It is also known that trigeminal ganglia, and their associated nerve pathways, are associated with painful sensations of the head and face such as headache and, in particular, migraine. Moskowitz (*Cephalalgia*, 12, 5–7, (1992) proposed that unknown triggers stimulate the trigeminal ganglia which in turn innervate vasculature within cephalic tissue, giving rise to the release of vasoactive neuropeptides from axons innervating the vasculature. These neuropeptides initiate a series of events leading to neurogenic inflammation of the meninges, a consequence of which is pain. This neurogenic inflammation is blocked by sumatriptan at doses similar to those required to treat acute migraine in humans. However, such doses of sumatriptan are associated with contraindications as a result of sumatriptan's attendant vasoconstrictive properties (see MacIntyre, P. D., et al., *British Journal of Clinical Pharmacology*, 34, 541–546 (1992); Chester, A. H., et al., *Cardiovascular Research*, 24, 932–937 (1990); Conner, H. E., et al., *European Journal of Pharmacology*, 161, 91–94 (1990)). Recently, it has been reported that all five members of the kainate subtype of ionotropic glutamate receptors are expressed on rat trigeminal ganglion neurons, and in particular, high levels of $GluR_5$ and KA2 have been observed. (Sahara et al., *The Journal of Neuroscience*, 17(17), 6611 (1997)). As such, migraine presents yet another neurological disorder which may be implicated with glutamate receptor excitotoxicity.

The use of a neuroprotective agent, such as an excitatory amino acid receptor antagonist, is believed to be useful in treating or preventing all of the aforementioned disorders and/or reducing the amount of neurological damage associated with these disorders. For example, studies have shown that AMPA receptor antagonists are neuroprotective in focal and global ischemia models. The competitive AMPA receptor antagonist NBQX (2,3-dihydroxy-6-nitro-7-sulfamoylbenzo[f]quinoxaline) has been reported effective in preventing global and focal ischemic damage. Sheardown et al., *Science*, 247, 571 (1900); Buchan et al., *Neuroreport*, 2, 473 (1991); LePeillet et al., *Brain Research*, 571, 115

(1992). The noncompetitive AMPA receptor antagonists GKYI 52466 has been shown to be an effective neuroprotective agent in rat global ischemia models. LaPeillet et al., *Brain Research*, 571, 115 (1992). European Patent Application Publication No. 590789A1 and U.S. Pat. Nos. 5,446,051 and 5,670,516 disclose that certain decahydroisoquinoline derivative compounds are AMPA receptor antagonists and, as such, are useful in the treatment of a multitude of disorders conditions, including pain and migraine headache. WO 98/45270 discloses that certain decahydroisoquinoline derivative compounds are selective antagonists of the iGluR$_5$ receptor and are useful for the treatment of various types of pain, including; severe, chronic, intractable, and neuropathic pain In accordance with the present invention, Applicants have discovered novel compounds that are antagonists of the iGluR$_5$ receptor subtype and, thus, could be useful in treating the multitude of neurological disorders or neurodegenerative diseases, as discussed above. Such antagonists could address a long felt need for safe and effective treatments for neruological disorders, without attending side effects. The treatment of neurological disorders and neurodegenerative diseases is hereby furthered.

SUMMARY OF THE INVENTION

The present invention provides a compound of Formula I

Formula I

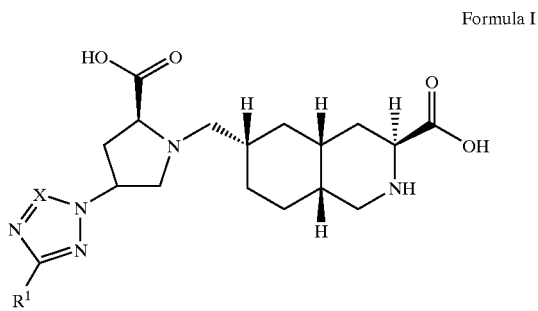

wherein

R$^1$ is H, (C$_1$–C$_6$)alkyl, (C$_1$–C$_6$)alkoxy, (C$_3$–C$_{10}$) cycloalkyl, SO$_2$R$^2$, CH$_2$SR$^2$, (C$_1$–C$_6$)alkyl(C$_1$–C$_6$) alkoxy, aryl, (C$_1$–C$_6$)alkylaryl, (C$_1$–C$_6$)alky (substituted)aryl, or substituted aryl;

R$^2$ is (C$_1$–C$_6$)alkyl; and

X is CH or N, or a pharmaceutically acceptable salt or prodrug thereof.

In addition, the present invention also provides a compound of Formula II

Formula II

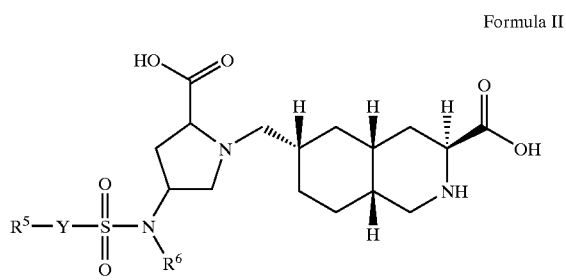

wherein

Y is (CH$_2$)$_n$

R$^5$ is aryl, substituted aryl, (C$_1$–C$_6$)alkyl, (C$_1$–C$_6$) alkylaryl, or CF$_3$;

R$^6$ is H, (C$_1$–C$_6$)alkyl, or (C$_1$–C$_6$)alkylaryl; and n is 0, 1, 2, or 3, or a pharmaceutically acceptable salt or prodrug thereof.

In another embodiment, the present invention provides a method of treating or preventing a neurological disorder, or neurodegenerative condition, comprising administering to a patient in need thereof an effective amount of a compound of Formula I or Formula II, or a pharmaceutically acceptable salt thereof. Examples of such neurological disorders, or neurodegenerative conditions, include: cerebral deficits subsequent to cardiac bypass surgery and grafting; stroke; cerebral ischemia; spinal cord lesions resulting from trauma or inflammation; perinatal hypoxia; cardiac arrest; hypoglycemic neuronal damage; Alzheimer's Disease; Huntington's Chorea; inherited ataxias; AIDS-induced dementia; amyotrophic lateral sclerosis; idiopathic and drug-induced Parkinson's Disease; ocular damage and retinopathy; muscular spasticity including tremors; drug tolerance and withdrawal; brain edema; convulsive disorders including epilepsy; depression; anxiety and anxiety related disorders such as post-traumatic stress syndrome; tardive dyskinesia; psychosis related to depression, schizophrenia, bipolar disorder, mania, and drug intoxication or addiction; headache, including cluster headache, tension-type headache, and chronic daily headache; migraine; and acute and chronic pain states including severe pain, intractable pain, neuropathic pain, and post-traumatic pain.

Specifically, the present invention provides a method of treating or preventing migraine comprising administering to a patient in need thereof an effective amount of a compound of Formula I or Formula II, or a pharmaceutically acceptable salt or prodrug thereof.

In addition, the present invention provides pharmaceutical compositions of compounds of Formula I and Formula II, including the pharmaceutically acceptable salts, prodrugs, and hydrates thereof, comprising, a compound of Formula I or Formula II in combination with a pharmaceutically acceptable carrier, diluent or excipient. This invention also encompasses novel intermediates, and processes for the synthesis of the compounds of Formula I and Formula II.

The present invention also provides the use of a compound of Formula I or Formula II for the manufacture of a medicament for treating or preventing a neurological disorder, or neurodegenerative condition.

More specifically, the present invention provides the use of a compound of Formula I or Formula II for the manufacture of a medicament for treating or preventing migraine.

DETAILED DESCRIPTION OF THE INVENTION

The present invention provides compounds functional as iGluR$_5$ receptor antagonists as well as pharmaceutically acceptable salts, prodrugs, and compositions thereof. These compounds are useful in treating or preventing neurological disorders, or neurodegenerative diseases, particularly migraine. As such, methods for the treatment or prevention of neurological disorders, or neurodegenerative diseases, are also provided by the present invention. Particularly, the present invention provides a method for the treatment of migraine which can be demonstrated by a particular mechanism of action, inhibition of neurogenic dural protein extravasation. By treating a migraineur with a compound or composition which is an antagonist of the iGluR$_5$ receptor, the neurogenic extravasation which mediates migraine is inhibited without the attending side effects of agents designed to optimize the 5-HT$_1$-like mediated vasoconstrictive activity of sumatriptan.

It should be understood by the skilled artisan that all of the compounds useful for the methods of the present invention are available for prodrug formulation. As used herein, the term "prodrug" refers to a compound of Formula I or Formula II which has been structurally modified such that in vivo the prodrug is converted, for example, by hydrolytic, oxidative, reductive, or enzymatic cleavage into the parent compound (e.g. the carboxylic acid (drug), or as the case may be the parent dicarboxylic acid) as given by Formula I or Formula II. Such prodrugs may be, for example, metabolically labile mono- or di-ester derivatives of the parent compounds having a carboxylic acid group. It is to be understood that the present invention includes any such prodrugs, such as metabolically labile ester or diester derivatives of compounds of the Formula I and Formula II. In all cases, the use of the compounds described herein as prodrugs is contemplated, and often is preferred, and thus, the prodrugs of all of the compounds employed are encompassed in the names of the compounds herein. Preferred prodrugs include the diester derivatives of Formula I and Formula II. Conventional procedures for the selection and preparation of suitable prodrugs are well known to one of ordinary skill in the art.

More specifically, examples of prodrugs of Formula I and Formula II which are understood to be included within the scope of the present invention, are represented by Formulas Ia and IIa below:

Formula Ia

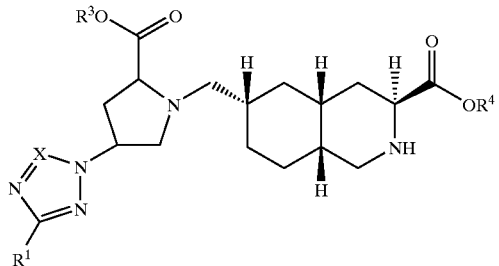

wherein
$R^1$, $R^2$, and X are as defined in Formula I; and
$R^3$ and $R^4$ each independently represent hydrogen, ($C_1$-$C_{20}$)alkyl, ($C_2$-$C_6$)alkenyl, ($C_1$-$C_6$)alkylaryl, ($C_1$-$C_6$)alkyl($C_3$-$C_{10}$)cycloalkyl, ($C_1$-$C_6$)alkyl-N,N-$C_1$-$C_6$ dialkylamine, ($C_1$-$C_6$)alkyl-pyrrolidine, ($C_1$-$C_6$)alkyl-piperidine, or ($C_1$-$C_6$)alkylmorpholine; with the proviso that at least one of $R^3$ or $R^4$ is other than hydrogen,
or a pharmaceutically acceptable salt thereof.

Formula IIa

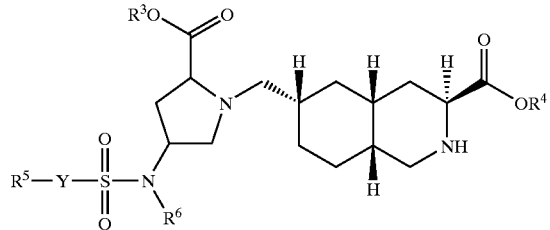

wherein
Y is $(CH_2)_n$
$R^5$ and $R^6$ are as defined in Formula II; and $R^3$ and $R^4$ each independently represent hydrogen, ($C_1$-$C_{20}$)alkyl, ($C_2$-$C_6$)alkenyl, ($C_1$-$C_6$)alkylaryl, ($C_1$-$C_6$)alkyl($C_3$-$C_{10}$)cycloalkyl, ($C_1$-$C_6$)alkyl-N,N-$C_1$-$C_6$ dialkylamine, ($C_1$-$C_6$)alkyl-pyrrolidine, ($C_1$-$C_6$)alkyl-piperidine, or ($C_1$-$C_6$)alkylmorpholine; with the proviso that at least one of $R^3$ or $R^4$ is other than hydrogen; and
n is 0, 1, 2, 3,
or a pharmaceutically acceptable salt thereof.

It is understood that the iGluR$_5$ receptor antagonists of the present invention may exist as pharmaceutically acceptable salts and, as such, salts are therefore included within the scope of the present invention. The term "pharmaceutically acceptable salt" as used herein, refers to salts of the compounds provided by, or employed in the present invention which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

It will be understood by the skilled reader that most or all of the compounds used in the present invention are capable of forming salts, and that the salt forms of pharmaceuticals are commonly used, often because they are more readily crystallized and purified than are the free bases. In all cases, the use of the pharmaceuticals described herein as salts is contemplated in the description herein, and often is preferred, and the pharmaceutically acceptable salts of all of the compounds are included in the names of them.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, hydroiodide, dihydroiodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid, hydroiodic and hydrobromic acid, and those formed with organic acids such as maleic acid, mandelic acid, and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of Formula I or Formula II can be resolved by one of ordinary skill in the art using standard techniques well known in the art, such as those described by J. Jacques, et al., "Enantiomers, Racemates, and Resolutions", John Wiley and Sons, Inc., 1981.

The compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The specific stereoisomers and enantiomers of compounds of Formula I and Formula II can be prepared by one of ordinary skill in the art utilizing well known techniques and processes, such as those disclosed by Eliel and Wilen, "Stereochemistry of Organic Compounds", John Wiley & Sons, Inc., 1994, Chapter 7, Separation of Stereoisomers. Resolution. Racemization, and by Collet and Wilen, "Enantiomers, Racemates, and Resolutions", John Wiley & Sons, Inc., 1981. For example, the specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

As a preferred embodiment of the present invention, the compounds of Formula I and Formula Ia have the following configurations:

Formula I

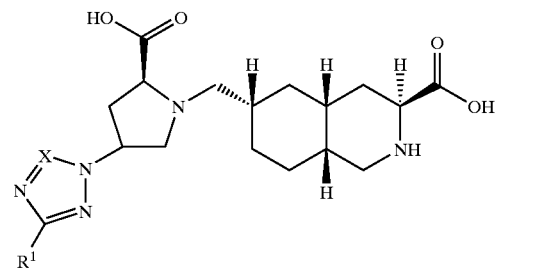

Formula I(a)

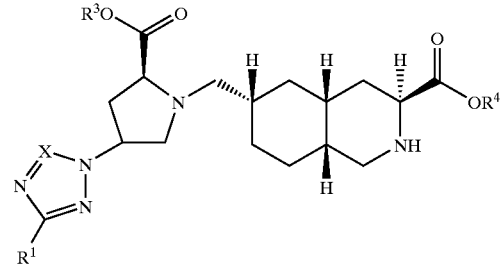

wherein $R^1$, $R^3$, $R^4$, and X are as defined hereinabove.

As yet another preferred embodiment of the present invention, the compounds of Formula II and Formula IIa have the following configurations:

Formula II

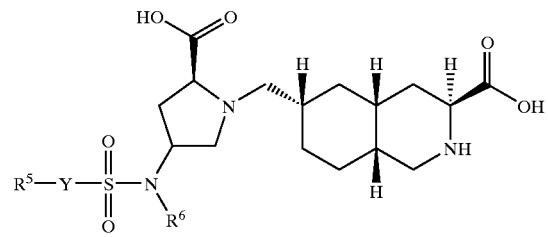

Formula IIa

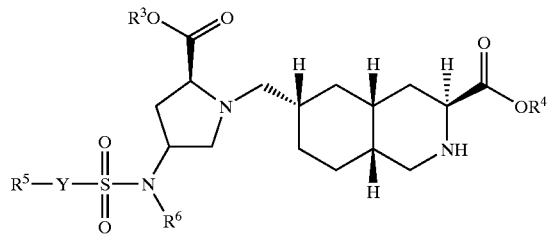

wherein $R^3$, $R^4$, $R^5$, $R^6$, and Y are as defined hereinabove.

As used herein the term "Pg" refers to a suitable nitrogen protecting group. Examples of a suitable nitrogen protecting group as used herein refers to those groups intended to protect or block the nitrogen group against undesirable reactions during synthetic procedures. Choice of the suitable nitrogen protecting group used will depend upon the conditions that will be employed in subsequent reaction steps wherein protection is required, and is well within the knowledge of one of ordinary skill in the art. Commonly used nitrogen protecting groups are disclosed in Greene, "Protective Groups In Organic Synthesis," (John Wiley & Sons, New York (1981)). Suitable nitrogen protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, .alpha.-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, .alpha., .alpha.-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred suitable nitrogen protecting groups are formyl, acetyl, methyloxycarbonyl, benzoyl, pivaloyl, t-butylacetyl, phenylsulfonyl, benzyl, t-butyloxycarbonyl (Boc) and benzyloxycarbonyl (Cbz).

As used herein the term "$(C_1-C_4)$alkyl" refers to a straight or branched, monovalent, saturated aliphatic chain of 1 to 6 carbon atoms and includes, but is not limited to methyl, ethyl, n-propyl, isopropyl, n-butyl, isobutyl and the like.

As used herein the term "$(C_1-C_6)$alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like.

As used herein the term "$(C_1-C_{10})$alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like.

As used herein the term "$(C_1-C_{20})$alkyl" refers to a straight or branched, monovalent, saturated aliphatic chain of 1 to 20 carbon atoms and includes, but is not limited to, methyl, ethyl, propyl, isopropyl, butyl, isobutyl, t-butyl, pentyl, isopentyl, hexyl, 3-methylpentyl, 2-ethylbutyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-nonadecyl, n-eicosyl and the like. It is understood that the terms "$(C_1-C_4)$alkyl", "$(C_1-C_6)$alkyl", and "$(C_1-C_{10})$alkyl" are included within the definition of "$(C_1-C_{20})$alkyl".

As used herein, the terms "Me", "Et", "Pr", "iPr", "Bu" and "t-Bu" refer to methyl, ethyl, propyl, isopropyl, butyl and tert-butyl respectively.

As used herein, the term "$(C_1-C_4)$alkoxy" refers to an oxygen atom bearing a straight or branched, monovalent, saturated aliphatic chain of 1 to 4 carbon atoms and includes, but is not limited to methyoxy, ethyoxy, n-propoxy, isopropoxy, n-butoxy, and the like.

As used herein the term "$(C_1-C_6)$alkoxy" refers to an oxygen atom bearing a straight or branched, monovalent, saturated aliphatic chain of 1 to 6 carbon atoms and includes, but is not limited to methoxy, ethoxy, n-propoxy, isopropoxy, n-butoxy, n-pentoxy, n-hexoxy, and the like.

As used herein, the term "$(C_1-C_6)$alkyl$(C_1-C_6)$alkoxy" refers to a straight or branched, monovalent, saturated aliphatic chain of 1 to 6 carbon atoms which has a $(C_1-C_6)$ alkoxy group attached to the aliphatic chain.

As used herein, the terms "Halo", "Halide" or "Hal" refer to a chlorine, bromine, iodine or fluorine atom, unless otherwise specified herein.

As used herein the term "$(C_2-C_6)$alkenyl" refers to a straight or branched, monovalent, unsaturated aliphatic chain having from two to six carbon atoms. Typical $C_2-C_6$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein, the term "aryl" refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like. The term "substituted aryl" refers to an aryl group substituted with one or two moieties chosen from the group consisting of halogen, hydroxy, cyano, nitro, $(C_1-C_6)$alkyl, $(C_1-C_6)$alkoxy, $(C_1-C_6)$alkyl $(C_3-C_{10})$cycloalkyl, $(C_1-C_6)$alkylaryl, $(C_1-C_6)$ alkoxycarbonyl, $SO_2CH_3$, phenyl, phenoxy protected carboxy, carboxymethyl, hydroxymethyl, amino, aminomethyl, or trifluoromethyl.

As used herein, the term "$(C_1-C_6)$alkylaryl" refers to a straight or branched, monovalent, saturated aliphatic chain of 1 to 6 carbon atoms which has an aryl group attached to the aliphatic chain. Included within the term "$C_1-C_6$ alkylaryl" are the following:

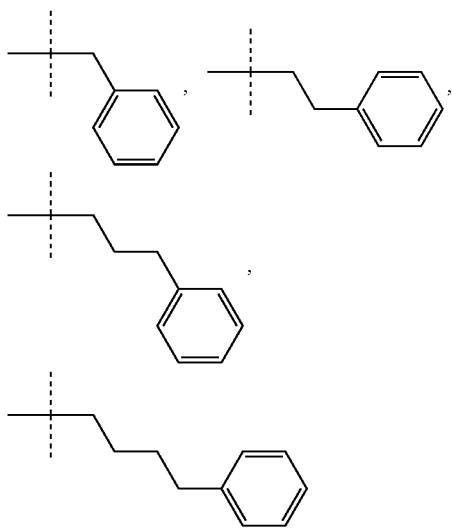

and the like.

As used herein, the term "$(C_1-C_6)$alky(substituted)laryl" refers to a straight or branched, monovalent, saturated aliphatic chain of 1 to 6 carbon atoms which has a substituted aryl group, as defined above, attached to the aliphatic chain.

As used herein, the term "aryl$(C_1-C_6)$alkyl" refers to an aryl group which has a straight or branched, monovalent, saturated aliphatic chain of 1 to 6 carbon atoms attached to the aryl group. Included within the term "aryl$(C_1-C_6)$alkyl" are the following:

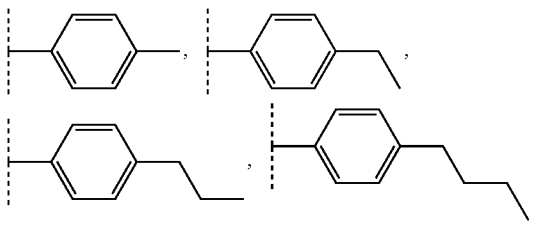

and the like.

As used herein the term "$(C_3-C_{10})$cycloalkyl" refers to a saturated hydrocarbon ring structure composed of one or more fused or unfused rings containing from three to ten carbon atoms. Typical $C_3-C_{10}$ cycloalkyl groups include cyclopropyl, cyclobutyl, cyclopentyl, cyclohexyl, cycloheptyl, cyclooctyl, adamantanyl, and the like.

As used herein, the term "$C_1-C_6$ alkyl$(C_3-C_{10})$cycloalkyl" refers to a straight or branched, monovalent, saturated aliphatic chain of 1 to 6 carbon atoms which has a $(C_3-C_{10})$cycloalkyl attached to the aliphatic chain. Included within the term "$C_1-C_6$ alkyl$(C_3-C_{10})$cycloalkyl" are the following:

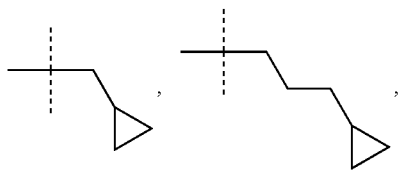

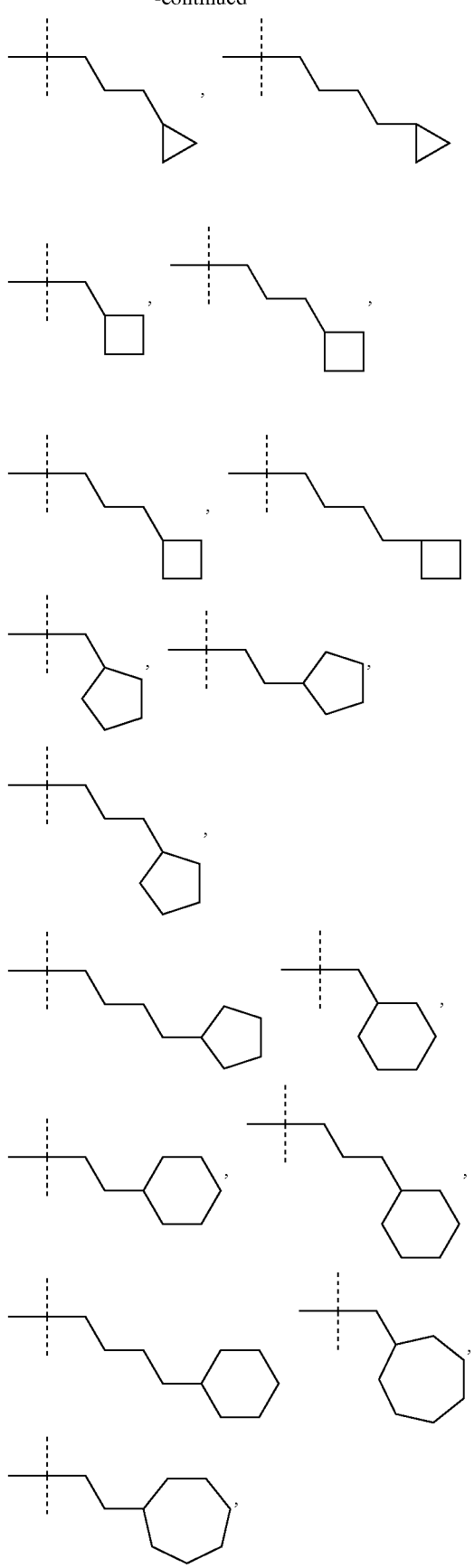

-continued

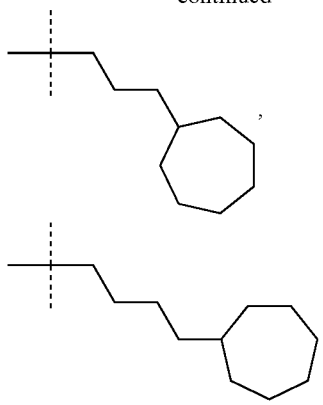

and the like.

As used herein, the term "($C_1$–$C_6$) alkoxycarbonyl" refers to a carbonyl group having a ($C_1$–$C_6$)alkyl group attached to the carbonyl carbon through an oxygen atom. Examples of this group include t-butoxycarbonyl, methoxycarbonyl, and the like.

As used herein the term "heterocycle" refers to a five- or six-membered ring, which contains one to four heteroatoms selected from the group consisting of oxygen, sulfur, and nitrogen. The remaining atoms of the ring are recognized as carbon by those of skill in the art. Rings may be saturated or unsaturated. Examples of heterocycle groups include thiophenyl, furyl, pyrrolyl, imidazolyl, pyrrazolyl, thiazolyl, thiazolidinyl, isothiazolyl, oxazolyl, isoxazolyl, triazolyl, thiadiazolyl, oxadiazolyl, tetrazolyl, pyridyl, pyrimidyl, pyrazinyl, pyridiazinyl, triazinyl, imidazolyl, dihydropyrimidyl, tetrahydropyrimdyl, pyrrolidinyl, piperidinyl, piperazinyl, pyrazolidinyl, pyrimidinyl, imidazolidimyl, morpholinyl, pyranyl, thiomorpholinyl, and the like. The term "substituted heterocycle" represents a heterocycle group substituted with one or two moieties chosen from the group consisting of halogen, hydroxy, cyano, nitro, oxo, ($C_1$–$C_6$)alkyl, ($C_1$–$C_4$)alkoxy, $C_1$–$C_6$ alkyl($C_3$–$C_{10}$)cycloalkyl, ($C_1$–$C_6$)alkylaryl, ($C_1$–$C_6$) alkoxycarbonyl, phenyl, phenoxy, protected carboxy, carboxymethyl, hydroxymethyl, amino, aminomethyl, or trifluoromethyl. Further, the heterocycle group can be optionally fused to one or two aryl groups to form a benzo-fused group. Examples of substituted heterocycle include 1,2,3,4-tetrahydrodibenzeofuranyl, 2-methylbezylfuranyl, and 3,5 dimethylisoxazolyl, and the like.

As used herein the term "N,N-$C_1$–$C_6$ dialkylamine" refers to a nitrogen atom substituted with two straight or branched, monovalent, saturated aliphatic chains of 1 to 6 carbon atoms. Included within the term "N,N-$C_1$–$C_6$ dialkylamine" are —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, and the like.

As used herein the term "$C_1$–$C_6$alkyl-N,N-$C_1$–$C_6$ dialkylamine" refers to straight or branched, monovalent, saturated aliphatic chain of 1 to 6 carbon atoms which has an N,N-$C_1$–$C_6$ dialkylamine attached to the aliphatic chain. Included within the term "$C_1$–$C_6$ alkyl-N,N-$C_1$–$C_6$ dialkylamine" are the following:

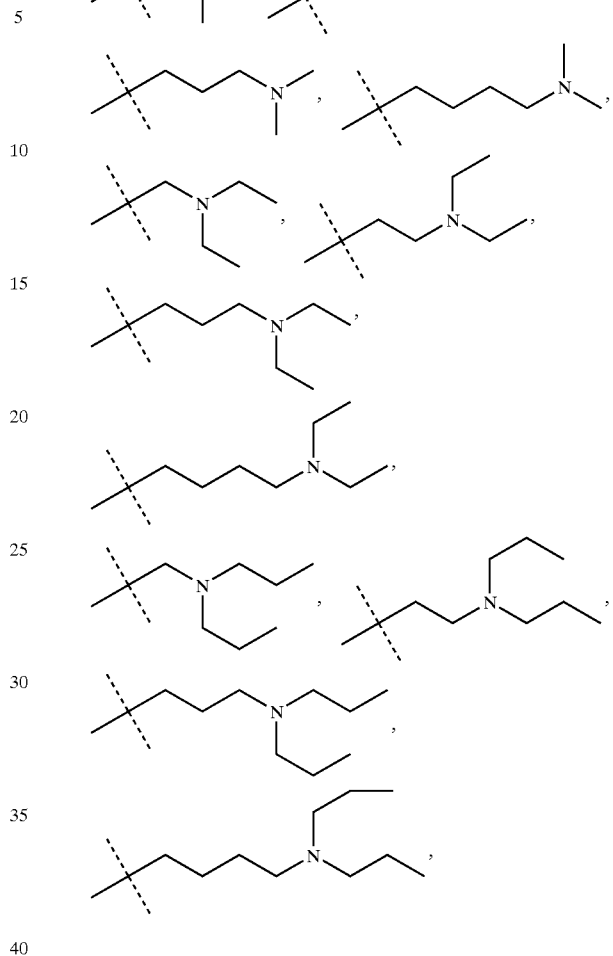

and the like.

As used herein the term "($C_1$–$C_6$)alkyl-pyrrolidine" refers to a straight or branched, monovalent, saturated aliphatic chain of 1 to 6 carbon atoms which has a pyrrolidine attached to the aliphatic chain. Included within the scope of the term "($C_1$–$C_6$)alkyl-pyrrolidine" are the following:

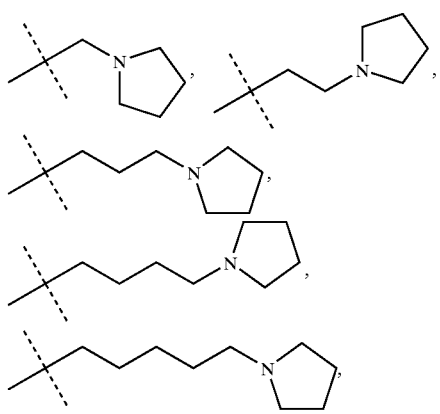

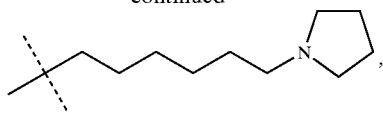

and the like.

As used herein the term "($C_1$–$C_6$)alkyl-piperidine" refers to a straight or branched, monovalent, saturated aliphatic chain of 1 to 6 carbon atoms which has a piperidine attached to the aliphatic chain. Included within the scope of the term "($C_1$–$C_6$)alkyl-piperidine" are the following:

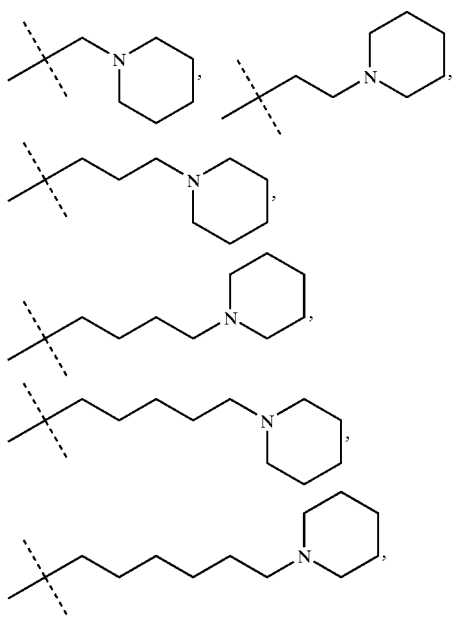

and the like.

As used herein the term "($C_1$–$C_6$)alkyl-morpholine" refers to a straight or branched, monovalent, saturated aliphatic chain of 1 to 6 carbon atoms which has a morpholine attached to the aliphatic chain. Included within the scope of the term "$C_1$–$C_6$ alkyl-morpholine" are the following:

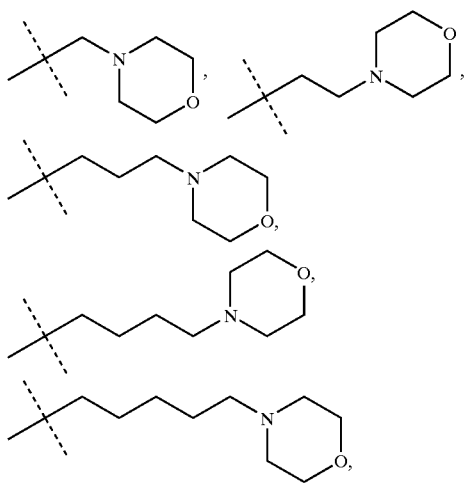

and the like.

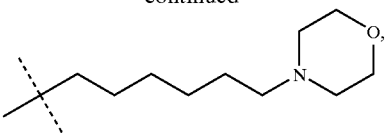

The designation "◂▬" refers to a bond that protrudes forward out of the plane of the page.

The designation "⋯⋯" refers to a bond that protrudes backward out of the plane of the page.

As used herein the term "iGluR$_5$" refers to the kainate ionotropic glutamate receptor, subtype 5, of the larger class of excitatory amino acid receptors.

As used herein the term "migraine" refers a disorder of the nervous system characterized by recurrent attacks of head pain (which are not caused by a structural brain abnormality such as those resulting from tumor or stroke), gasrointestinal disturbances, and possibly neurological symptoms such as visual distortion. Characteristic headaches of migraine usually last one day and are commonly accompanied by nausea, emesis, and photophobia.

Migraine may represent a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of migraine contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human.

The term "iGluR$_5$ receptor antagonist" or "iGluR$_5$ antagonist", as used herein, refers to those excitatory amino acid receptor antagonists which bind to, and antagonize the activity of, the iGluR$_5$ kainate receptor subtype. As a preferred embodiment, the present invention further provides selective iGluR$_5$ receptor antagonists. "Selective iGluR$_5$ receptor antagonist" or "selective iGluR$_5$ antagonist" as used herein, includes those excitatory amino acid receptor antagonists which selectively bind to, and antagonize, the iGluR$_5$ kainate receptor subtype, relative to the iGluR$_2$ AMPA receptor subtype. Preferably the "selective iGluR$_5$ antagonists" for use according to the methods of the present invention have a binding affinity at least 10 fold greater for iGluR$_5$ than for iGluR$_2$, more preferably at least 100 fold greater. WO 98/45270 provides examples of selective iGluR$_5$ receptor antagonists and discloses methods for synthesis.

As used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

Oral administration is a preferred route of administering the compounds employed in the present invention whether administered alone, or as a combination of compounds capable of acting as a selective iGluR$_5$ receptor antagonist. Oral administration, however, is not the only route, nor even the only preferred route. Other preferred routes of administration include transdermal, percutaneous, pulmonary, intravenous, intramuscular, intranasal, buccal, sublingual, or intrarectal routes. Where the selective iGluR$_5$ receptor antagonist is administered as a combination of compounds, one of the compounds may be administered by one route, such as oral, and the other may be administered by the transdermal, percutaneous, pulmonary, intravenous, intramuscular, intranasal, buccal, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating compounds of Formula I or Formula II are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I or Formula II, including the pharmaceutically acceptable salts, prodrugs, and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment. The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

The following table provides an illustrative list of formulations suitable for use with the compounds employed in the present invention. The following is provided only to illustrate the invention and should not be interpreted as limiting the present invention in any way.

Formulation 1

Hard gelatin capsules are prepared using the following ingredients:

|  | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
|---|---|
| Active Ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| Active Ingredient | 60.0 mg |
|---|---|
| Starch | 45.0 mg |
| Microcrystalline cellulose | 35.0 mg |
| Polyvinylpyrrolidone | 4.0 mg |
| Sodium carboxymethyl starch | 4.5 mg |
| Magnesium stearate | 0.5 mg |
| Talc | 1.0 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules each containing 80 mg medicament are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into bard gelatin capsules in 200 mg quantities.

Formulation 6

Suppositories each containing 225 mg of active ingredient may be made as follows:

| Active Ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| Active Ingredient | 100 mg |
|---|---|
| Mannitol | 100 mg |
| 5 N Sodium hydroxide | 200 ml |
| Purified water to total | 5 ml |

It is understood by one of ordinary skill in the art that the procedures as described above can also be readily applied to a method of treating neurological disorders or neurodegenerative conditions, particularly migraine, comprising administering to a patient an effective amount of a compound of Formula I or Formula II.

Compounds of Formula I and Formula II can be prepared, for example, by following the procedures set forth in Scheme I and Scheme II, respectively. All substituents, unless otherwise indicated, are previously defined. The reagents and starting materials are readily available to one of ordinary skill in the art. For example, certain starting materials can be prepared by one of ordinary skill in the art following procedures disclosed in U.S. Pat. No. 5,356,902 (issued Oct. 18, 1994) and U.S. Pat. No. 5,446,051 (issued Aug. 29, 1995).

Scheme I

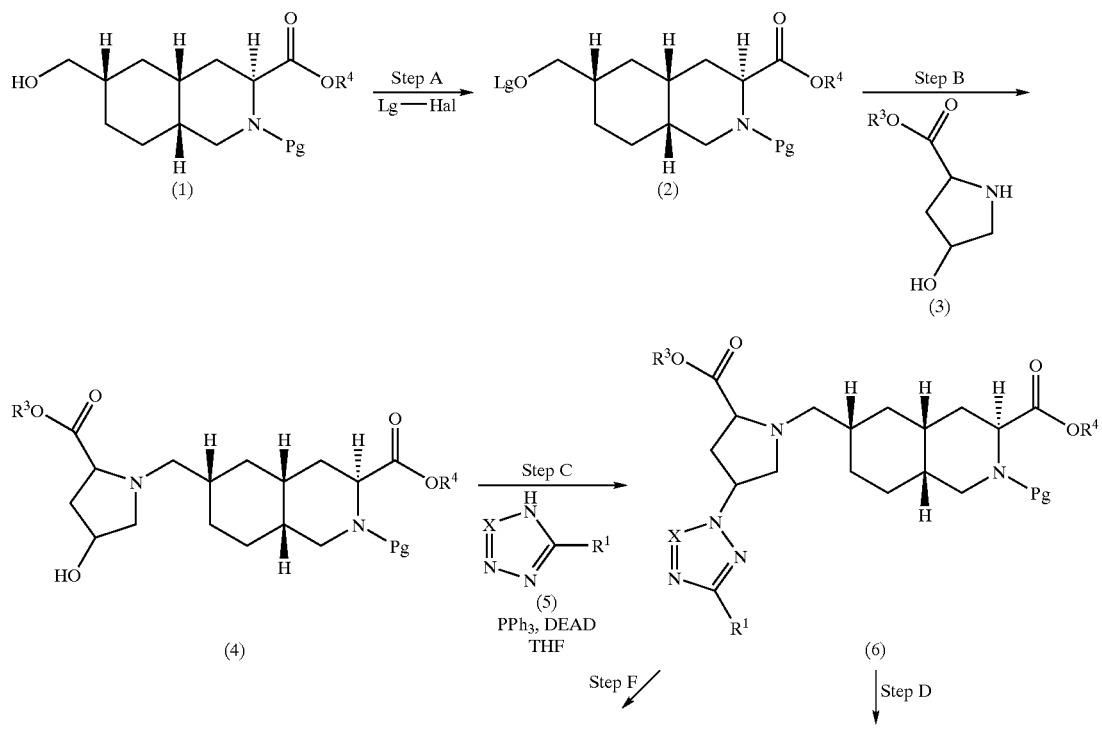

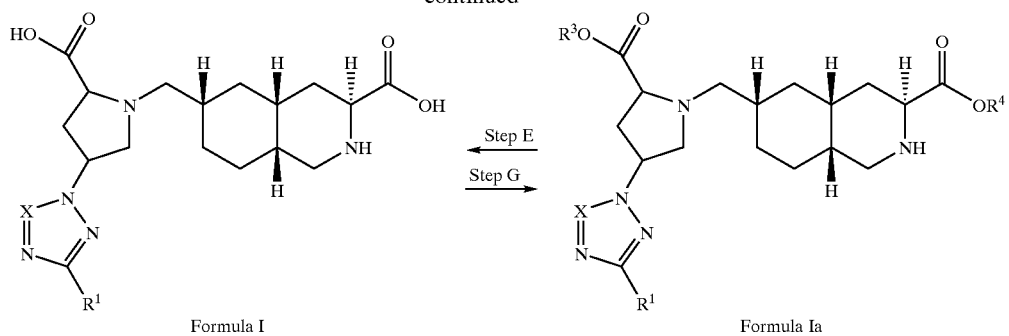

Formula I                        Formula Ia

In Scheme I, step A, the 6-hydroxymethyl-2-methoxycarbonyl-decahydroisoquinoline-3-carboxylate of compound (1) (Pg is a suitable nitrogen protecting group as defined hereinabove, with methoxycarbonyl being preferred) is treated under standard conditions with a compound of formula Lg-Hal, wherein Lg is a suitable leaving group and Hal represents a chloro, bromo or iodo atom, to provide the compound of structure (2). For example, a solution of compound (1), dissolved in a suitable organic solvent such as dichloromethane and cooled to 0° C., is treated with an excess of a suitable organic base, such as triethylamine, followed by about 1 to 2 equivalents of a compound of formula Lg-Hal. Examples of Lg-Hal include m-nitrobenzenesulfonyl chloride, p-nitrobenzenesulfonyl chloride, p-bromobenzenesulfonyl chloride, p-toluenesulfonyl chloride, benzenesulfonyl chloride, methanesulfonyl chloride, trifluoromethanesulfonyl chloride, and the like. The reaction mixture is warmed to room temperature and stirred for about 5 to 20 hours. The compound (2) is then isolated using standard procedures. For example, the reaction mixture is washed with water, the organic layer separated and dried over anhydrous sodium sulfate, filtered, and concentrated under vacuum to provide crude compound (2). Column chromatography can then be performed on silica gel with a suitable eluent such as 10–50% ethyl acetate/hexane to provide the purified compound (2).

In Scheme I, Step B, compound (2) is treated under standard conditions with a pyrrolidine of structure (3) to provide the compound of structure (4). For example, compound (2) of Step A above is mixed with about 1–1.5 equivalents of 4-hydroxy-L-proline ethyl ester ($R^3$ is ethyl) and 1–1.5 equivalents of potassium carbonate and heated at reflux in a suitable solvent such as acetonitrile for about 60–70 hours. The reaction mixture is cooled to room temperature and solvents removed under vacuum. Compound (4) is then isolated using standard procedures such as extraction techniques. For example, the reaction mixture is partitioned between water and an organic solvent such as diethyl ether, and the aqueous layer extracted 2–6 times with diethyl ether. The organic layers are combined, dried over anhydrous sodium sulfate, filtered, and concentrated under vacuum to provide compound (4). Compound (4) can then be purified by chromatography on silica gel with a suitable eluent such as ethyl acetate/hexanes or methanol/chloroform.

In Scheme I, Step C, compound (4) is treated with a compound of structure (5) in the presence of $PPh_3$ and DEAD to give the compound of structure (6). For example, a solution of Ethyl-6-(5-ethoxycarbonyl)-3-hydroxypyrrolidinyl)methyl)-2-methoxycarbonyl-decahydroisoquinoline-3-carboxylate, about 1–1.4 equivalents of compound (5) (where $R^1$ is as defined hereinabove) and about 1–1.4 equivalents of triphenylphosphine in tetrahydrofuran is cooled to 0° C. Diethyl azodicarboxylate (about 1–1.4 equivalents) is added dropwise and the reaction is allowed to warm to room temperature then stirred for about 15–20 hours. The solvents are removed under vacuum to provide the compound of structure (6). Compound (6) can then be purified by chromatography on SCX silica gel and/or silica gel with a suitable eluent such as 2 N ammonia in ethanol and/or ethyl acetate/hexanes.

In Scheme I, Step D, compound (6) is deprotected under standard conditions well known in the art to provide the compound of Formula Ia. For example, when Pg is a methoxycarbonyl protecting group, compound (8) is dissolved in a suitable organic solvent such as dichloromethane under an atmosphere of nitrogen and treated with a trialkylsilyl iodide ($Alk_3SiI$) such as trimethylsilyl iodide, triethylsilyl iodide, tributylsilyl iodide, and the like, with trimethylsilyl iodide being most preferred. The reation mixture is allowed to warm to room temperature and stirred for about 10–20 hours. The reaction is quenched by addition of saturated aqueous $NaHCO_3$. The aqueous layer is then extracted 2–6 times with dichloromethane. The organics are then combined, washed with a 1N solution of sodium thiosulfate, dried over magnesium sulfate, filtered, and concentrated in vacuo to provide the compound of Formula Ia. The material can then be purified by chromatography on silica gel with a suitable eluent such as methanol/dichoromethane, to provide the purified compound of Formula Ia.

In Scheme I, Step E, the compound of Formula Ia is hydrolyzed to the compound of Formula I under conditions well known in the art. For example, the compound of Formula Ia is dissolved in a suitable organic solvent such as methanol, and treated with an excess of a suitable base. Examples of suitable bases include aqueous lithium hydroxide, sodium hydroxide, potassium hydroxide, and the like, with lithium hydroxide being preferred. The reaction is stirred for about 10–20 hours. The reaction mixture is then neutralized to pH 6 with 1N HCl and concentrated under vacuum to provide the crude compound of Formula I. This material is then purified by techniques well known in the art, such as cation exchange chromatography eluting with methanol/water followed by 2 N ammonia in methanol to provide the purified compound of Formula I.

In Scheme I, Step F, compound (6) is deprotected and hydrolyzed concomitantly to provide the compound of Formula I. For example, a solution of compound (6) dissolved in 6N HCl is heated to reflux (90–95° C.) for about 15–20 hours. The reaction mixture is then allowed to cool to room temperature and concentrated in vacuo to provide the compound of Formula I. The compound of Formula I can then be purified by techniques well known in the art, such as cation exchange chromatography eluting with methanol/water followed by 2N ammonia in methanol or ethanol to provide the purified compound of Formula I.

In Scheme I, Step G, the compound of Formula I can be esterified, under conditions well known in the art, to provide the compound of Formula Ia. For example, the compound of Formula I is dissolved in a suitable organic solvent such as ethanol, and treated with an excess of a suitable acid. Examples of suitable acids include gaseous hydrochloric acid, aqueous sulfuric acid, p-toluene sulfonic acid, and the like with gaseous hydrochloric acid being preferred. The reaction mixture is heated to reflux (78–85° C.) for about 15–25 hours. The reaction mixture concentrated under vacuum to provide the crude compound of Formula Ia. This material can then be purified by techniques well known in the art, such as cation exchange chromatography eluting with methanol/water followed by 2N ammonia in ethanol to provide the purified compound of Formula Ia.

hours. The solvents are removed under vacuum to provide the compound of structure (8) wherein $R^6$ represents hydrogen. Compound (8) may then be purified by chromatography on SCX silica gel and/or silica gel with a suitable eluent such as 2N ammonia in ethanol and/or ethyl acetate/hexanes.

The compound of structure (8) may used directly in Steps D or F or compound (8) may be further alkylated to provide the compound of structure (8) wherein R6 is other than hydrogen. For example, to a solution of compound (8) in tetrahydrofuran is added a 1M solution of sodium bis(trimethyl-silyl)amide dropwise. The mixture is then stirred for about 30 minutes then a compound of formula $R^6$-hal is added, wherein hal represents bromine, iodine or chlorine and $R^6$, for the purpose of the present step, represents $(C_1-C_6)$alkyl or $(C_1-C_6)$alkylaryl. The mixture is then stirred for about 2 to 18 hours at about RT to 65 degrees celsius, then allowed to cool to RT. To the mixture is then added about 5 ml of water and about 5 ml of diethylether. The organic layer is then separated and the aqueous layer is extracted about 3 times with diethyl ether. The organics are

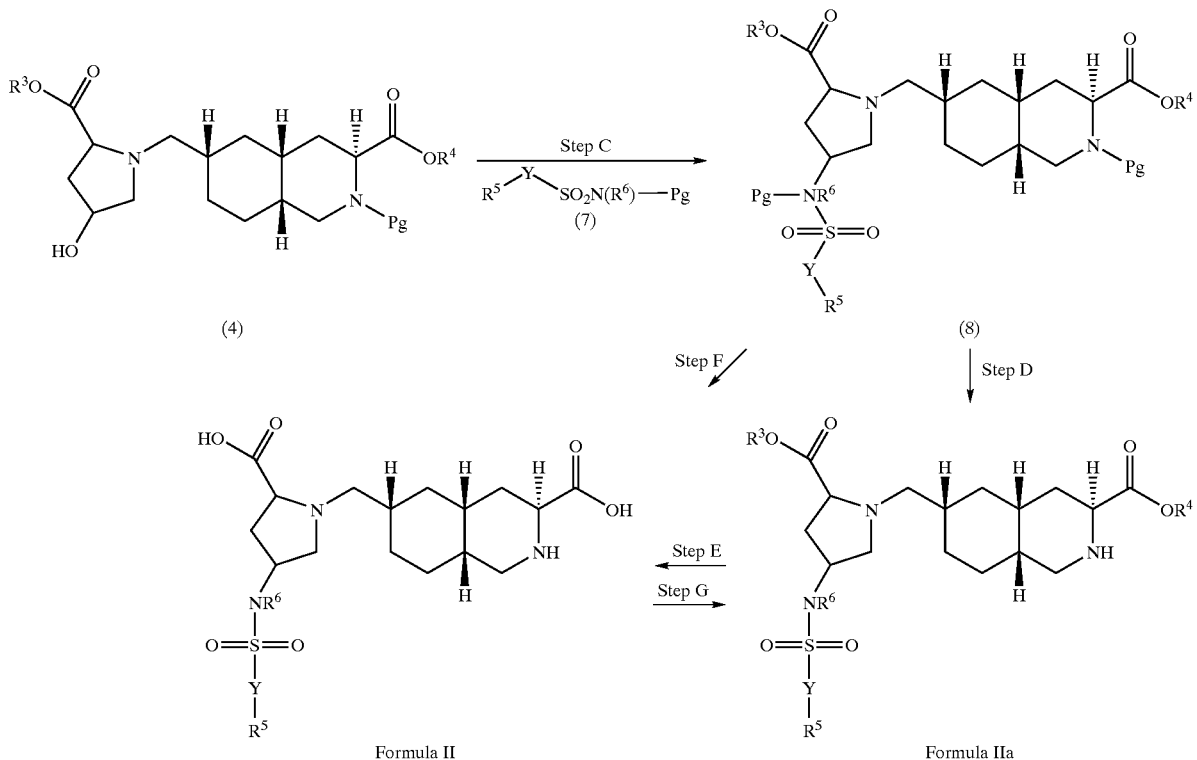

Scheme II

In Scheme II, Step C, compound (4) (which can be prepared as described in Scheme I, Steps A and B) is treated with a compound of structure (7) (wherein $R^6$ represents hydrogen) in the presence of $PPh_3$ and DEAD to give the compound of structure (8) (wherein $R^6$ represents hydrogen). For example, a solution of Ethyl-6-(5-ethoxycarbonyl)-3-hydroxypyrrolidinyl)methyl)-2-methoxycarbonyl-decahydroisoquinoline-3-carboxylate, about 1–1.4 equivalents of compound (7) and about 1–1.4 equivalents of triphenylphosphine in tetrahydrofuran is cooled to 0° C. Diethyl azodicarboxylate (about 1–1.4 equivalents) is added dropwise and the reaction is allowed to warm to room temperature then stirred for about 15–20 hours. The solvents are removed under vacuum to provide combined, dried over $MgSO_4$, filtered, and concentrated under vacuum to provide the compound of structure (8), wherein $R^6$ represents $(C_1-C_6)$alkyl or $(C_1-C_6)$alkylaryl. This material may then be purified by chromatography on SCX silica gel and/or silica gel with a suitable eluent such as 2N ammonia in ethanol and/or ethyl acetate/hexanes.

In Scheme II, Step D, compound (8) is deprotected under standard conditions well known in the art to provide the compound of Formula IIa. For example, when Pg is a methoxycarbonyl protecting group, compound (8) is dissolved in a suitable organic solvent such as dichloromethane under an atmosphere of nitrogen and treated with trimethylsilyl iodide. The reation mixture is allowed to warm to room temperature and stirred for about about 10–20 hours. The reaction is quenched by addition of saturated aqueous NaHCO$_3$. The aqueous layer is then extracted 2–6 times with dichloromethane. The organics are then combined, washed with a 1N solution of sodium thiosulfate, dried over magnesium sulfate, filtered, and concentrated in vacuo to the compound of Formula IIa. The material can then be purified by chromatography on silica gel with a suitable eluent such as methanol/dichoromethane, to provide the purified compound of Formula IIa.

In Scheme II, Step E, the compound of Formula IIa is hydrolyzed to the compound of Formula II under conditions well known in the art. For example, the compound of Formula IIa is dissolved in a suitable organic solvent such as methanol, and treated with an excess of a suitable base. Examples of suitable bases include aqueous lithium hydroxide, sodium hydroxide, potassium hydroxide, and the like, with lithium hydroxide being preferred. The reaction is stirred for about about 10–20 hours. The reaction mixture is then neutralized to pH 6 with 1N HCl and concentrated under vacuum to provide the crude compound of Formula II. This material may then be purified by techniques well known in the art, such as cation exchange chromatography eluting with methanol/water followed by 2N ammonia in methanol to provide the purified compound of Formula II.

In Scheme II, Step F, compound (8) is deprotected and hydrolyzed concomitantly to provide the compound of Formula II. For example, a solution of compound (8) dissolved in 6.0 N HCl is heated at reflux (90–95° C.) for about 15–20 hours. The reaction mixture is then allowed to cool to room temperature and concentrated in vacuo to provide the compound of Formula II. The compound of Formula II may then be purified by techniques well known in the art, such as cation exchange chromatography eluting with methanol/water followed by 2 N ammonia in methanol or ethanol to provide the purified compound of Formula II.

In Scheme II, Step G, the compound of Formula II is esterified to provide the compound of Formula IIa. For example, the compound of Formula H is dissolved in a suitable organic solvent such as ethanol, and treated with an excess of a suitable acid. Examples of suitable acids include gaseous hydrochloric acid, aqueous sulfuric acid, p-toluene sulfonic acid, and the like with gaseous hydrochloric acid being preferred. The reaction mixture is heated at reflux (78–85° C.) for about 15–24 hours. The reaction mixture concentrated under vacuum to provide the crude compound of Formula IIa. This material may then be purified by techniques well known in the art, such as cation exchange chromatography eluting with methanol/water followed by 2 N ammonia in ethanol to provide the purified compound of Formula Ia.

The nitrogen-protected sulfonamides of structure (7), in Scheme II above, may be synthesized according to the procedures described in Scheme II(a) below:

Scheme II(a)

R$^5$—Y—SO$_2$NH$_2$ →(Step A, (Boc)$_2$O, DMAP, Et3N, CH$_2$Cl$_2$)→ R$^5$—Y—SO$_2$NH—Pg
(vii)                                                                (7)

In Scheme II(a), Step A, a sulfonamide of structure (vii), where Y and R$^5$ are as defined hereinabove, is treated with di-tert-butyl dicarbonate to provide the N-protected sulfonamide of structure (7). For example, to a solution of a sulfonamide of structure (vii) (which is readily available or can be readily prepared by one of ordinarly skill in the art), triethylamine, and 4-dimethylaminopyridine, in dichloromethane is added di-tert-butyl dicarbonate. The reaction is stirred for about 18 hours at ambient temperature and then washed with about 200 mL of a 10% aqueous solution of sodium hydrogen sulfate and about 200 mL of brine. The organic layer is removed and dried over magnesium sulfate and concentrated under vacuum to afford the N-protected sulfonamide compound of structure (7).

The Formula I and Formula II compounds of the present invention may be chemically synthesized from a common intermediate, a 6-hydroxymethyl-2-methoxycarbonyl-decahydroisoquinoline-3-carboxylate. This 6-hydroxymethyl intermediate, in turn, may be chemically synthesized from a 6-oxo-2-methoxycarbonyl-decahysdroisoquinoline-3-carboxylic acid intermediate, the synthesis of which is described in U.S. Pat. No. 4,902,695, No. 5,446,051, and No. 5,356,902.

Routes for the synthesis of the 6-hydroxymethyl-2-methoxycarbonyl-decahydroisoquinoline-3-carboxylate intermediate, useful for the synthesis of the compounds of the present invention, are shown in Schemes IIa and IIIb below.

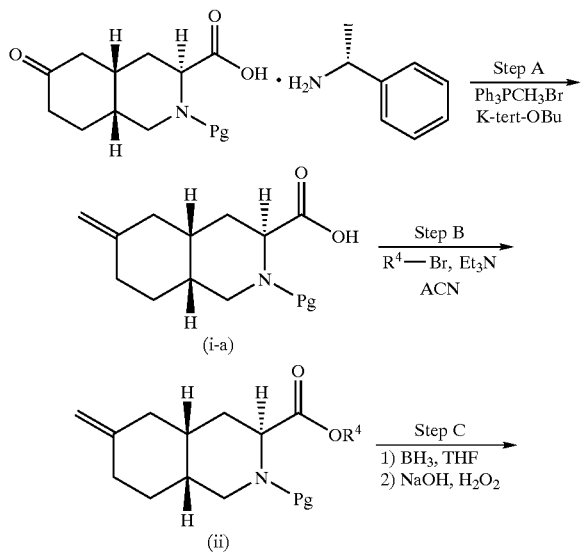

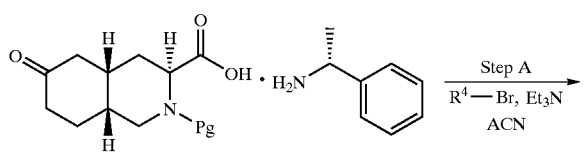

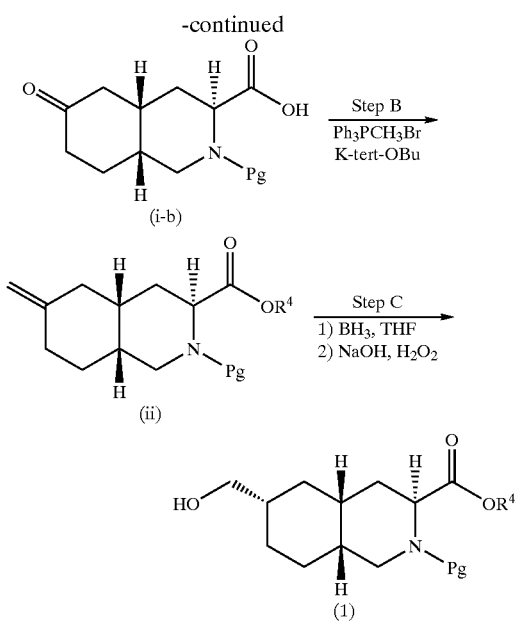

In Scheme IIIa, Step A, 6-oxo-decahydroisoquinoline-3-carboxylic acid is treated with methyltriphenylphosphonium bromide to provide the 6-methylidine-decahydroisoquinoline-3-carboxylic acid of compound (i-a). For example, a slurry of 1 equivalent of 6-oxo-2-methoxycarbonyl-decahydroisoquinoline-3-carboxylic acid and about 1.4 equivalents of methyltriphenylphosphonium bromide in THF and DMF is stirred mechanically under an atmosphere of nitrogen and cooled to −10° C. Potassium tert-butoxide solution (2.4 equiv in THF) is added dropwise over a 10 minute period. The slurry is allowed to warm to room temperature and stirred thus for 2.5 hours (complete by TLC at this time). The reaction is partitioned between water and EtOAc and the layers are separated. The organic phase is extracted 2 times with water and the aqueous portions are combined and washed 2–6 times with dichloromethane. The aqueous solution is made acidic by addition of 6 M HCl solution and extracted 2–6 times with dichloromethane. These last three organic extracts are combined, dried with sodium sulfate and concentrated under reduced pressure to provide the compound of structure (i-a).

In Scheme IIIa, Step B, the intermediate 6-methylidine-decahydroisoquinoline-3-carboxylic acid (compound (i-a)) is esterified by reaction with a compound of formula $R^4$-Br (where $R^4$ is as herein defined) to provide the 6-methylidine-decahydroisoquinoline-3-carboxylate intermediate of compound (ii). For example 6-methylidine-2-methoxycarbonyl-decahydroisoquinoline-3-carboxylic acid is dissolved in acetonitrile and treated with triethylamine and bromoethane. The reaction is heated at 50° C. for about 3 hours, cooled and partitioned between 50:50 ethyl acetate/heptane and 1N HCL. The organic phase is isolated and washed 3 times with water, saturated sodium bicarbonate, brine, dried over anhydrous sodium sulfate, filtered, and concentrated under vacuum to provide the compound of structure (ii). This crude material is dissolved in 10% ethyl acetate/heptane and applied to a plug of silica gel (10 g in 10% ethyl acetate/heptane). The plug is eluted with, 10% ethyl acetate/heptane, 15% ethyl acetate/heptane, and 25% ethyl acetate/heptane. The eluents are combined and concentrated under vacuum to provide the purified compound of structure (ii).

In Scheme IIIa, Step C, the 6-methylidine-decahydroisoquinoline-3-carboxylate intermediate (compound (ii)) is subjected to hydroboration, followed by oxidation to provide the 6-hydroxymethyl-decahydroisoquinoline-3-carboxylate intermediate of compound (1). For example, Ethyl-6-methylidine-2-methoxycarbonyl-decahydroisoquinoline-3-carboxylate is dissolved in THF and cooled to about −15° C. under an atmosphere of nitrogen with stirring. A 1M solution of $BH_3$·THF is added dropwise over 5–7 minutes and the reaction mixture is stirred for about 2 hours at −10 to −12° C. The reaction is then slowly treated with a suitable base, such as lithium hydroxide, and then treated slowly with 30% $H_2O_2$ over 15 minutes. The reaction mixture is allowed to warm to room temperature and then partitioned between ethyl acetate and 50% saturated sodium chloride solution. The aqueous layer is extracted with ethyl acetate and the combined organics are washed with sodium bisulfite solution, brine, dried over anhydrous sodium sulfate, filtered, and concentrated under vacuum to provide the intermediate of compound (1).

Alternatively, the 6-hydroxymethyl-2-methoxycarbonyl-decahydroisoquinoline-3-carboxylate intermediate (compound (1)) may be made according to the synthetic route described in Scheme IIIb. In Scheme IIIb, Step A, 6-oxo-decahydroisoquinoline-3-carboxylic acid is esterified by reaction with a compound of formula $R^4$-Br (where $R^4$ is as herein defined) to provide the 6-oxo-decahydroisoquinoline-3-carboxylate intermediate of compound (i-b). For example 6-oxo-2-methoxycarbonyl-decahydroisoquinoline-3-carboxylic acid is dissolved in acetonitrile and treated with tiethylamine and bromoethane. The reaction is heated at 50° C. for about 3 hours, cooled and partitioned between 50:50 ethyl acetate/heptane and 1N HCL. The organic phase is isolated and washed 3 times with water, saturated sodium bicarbonate, brine, dried over anhydrous sodium sulfate, filtered, and concentrated under vacuum to provide the compound of structure (i-b). This crude material is dissolved in 10% ethyl acetate/heptane and applied to a plug of silica gel (10 g in 10% ethyl acetate/heptane). The plug is eluted with, 10% ethyl acetate/heptane, 15% ethyl acetate/heptane, and 25% ethyl acetate/heptane. The eluents are combined and concentrated under vacuum to provide the purified compound of structure (i-b).

In Scheme IIIb, Step B, the 6-oxo-decahydroisoquinoline-3-carboxylate intermediate of compound (i-b) is treated with methyltriphenylphosphonium bromide to provide the 6-methylidine-decahydroisoquinoline-3-carboxylate of compound (ii). For example a slurry of 1 equivalent of 6-oxo-2-methoxycarbonyl-decahydroisoquinoline-3-carboxylate (compound (i-b)) and about 1.4 equivalents of methyltriphenylphosphonium bromide in THF and DMF is stirred mechanically under an atmosphere of nitrogen and cooled to −10° C. Potassium tert-butoxide solution (2.4 equiv in THF) is added dropwise over a 10 minute period. The slurry is allowed to warm to room temperature and stirred thus for 2.5 hours (complete by TLC at this time). The reaction is partitioned between water and EtOAc and the layers are separated. The organic phase is extracted 2 times with water and the aqueous portions are combined and washed 2–6 times with dichloromethane. The aqueous solution is made acidic by addition of 6 M HCl solution and extracted 2–6 times with dichloromethane. These last three organic extracts are combined, dried with sodium sulfate and concentrated under reduced pressure to provide the compound of structure (ii).

In Scheme IIIb, Step C, following the procedures as described in Scheme IIIa, Step C above, the 6-methylidine-decahydroisoquinoline-3-carboxylate intermediate (compound (ii)) is subjected to hydroboration, followed by oxidation to provide the 6-hydroxymethyl-decahydroisoquinoline-3-carboxylate intermediate of compound (1).

The following preparations and examples further illustrate the invention and represent typical synthesis of the compounds of Formula I and Formula II as described generally above. The reagents and starting materials are readily available to one of ordinary skill in the art. As used herein, the following terms have the meanings indicated: "i.v." refers to intravenously; "p.o." refers to orally; "i.p." refers to intraperitoneally; "eq" or "equiv." refers to equivalents; "g" refers to grams; "mg" refers to milligrams; "L" refers to liters; "mL" refers to milliliters; "μL" refers to microliters; "mol" refers to moles; "mmol" refers to millimoles; "psi" refers to pounds per square inch; "mm Hg" refers to millimeters of mercury; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to dimethyl sulfoxide; "aq" refers to aqueous; "EtOAc" refers to ethyl acetate; "iPrOAc" refers to isopropyl acetate; "MeOH" refers to methanol; "MTBE" refers to tert-butyl methyl ether; "$PPh_3$" refers to triphenylphosphine; "DMAP" refers to dimethyl aminopyridine; "DEAD" refers to diethyl azodicarboxylate; "RT" refers to room temperature; "$K_i$" refers to the dissociation constant of an enzyme-antagonist complex and serves as an index of ligand binding; and "$ID_{50}$" and "$ID_{100}$" refer to doses of an administered therapeutic agent which produce, respectively, a 50% and 100% reduction in a physiological response.

Preparation 1

3S,4aR,6S,8aR Ethyl 6-(((3S,5S)-5-(Ethoxycarbonyl)-3-hydroxypyrrolidinyl)methyl)-2-methoxycarbonyl-1,2,3,4,4a,5,6,7,8,8a-decahydroisoquinoline-3-carboxylate A. Preparation of 3S,4aR,6S,8aR Ethyl 6-((4-Methylphenyl)sulfonyloxy)methyl)-2-methoxycarbonyl-1,2,3,4,4a,5,6,7,8,8a-decahydroisoquinoline-3-carboxylate To a solution of 15.0 g (50.1 mmol) of Ethyl 6-hydroxymethyl-2-methoxycarbonyl-decahydroisoquinoline-3-carboxylate (See Col.11–12, Scheme II of U.S. Pat. No. 5,356,902, the entire contents of which are herein incorporated by reference) cooled to 0° C. in $CH_2Cl_2$ (100 mL), was added triethylamine (20.9 mL, 150.3 mmol) followed by toluenesolfonyl chloride (19.1 g, 100.2 mmol) dissolved in $CH_2Cl_2$ (100 mL). The reaction was warmed to room temperature and stirred 16 h, then partitioned between $CH_2Cl_2$ and 10% aqueous $NaHSO_4$. The aqueous layer was extracted with $CH_2Cl_2$ and the combined organics were dried over $MgSO_4$, filtered, and concentrated in vacuo. Column chromatography (10–50% EtOAc/hexane) provided 20.1 g (89%) of the desired intermediate title compound as a colorless oil:

MS (m/e): 451.5 ($M^+$) Calculated for $C_{22}H_{31}NO_7S$ 0.1 $CH_2Cl_2$: Theory: C, 57.45; H, 6.81; N, 3.03. Found: C, 57.76; H, 6.93; N, 3.35.

$^{13}C$ NMR (DMSO-$d_6$): δ 171.4, 144.8, 132.4, 130.1, 127.6, 74.6, 60.4, 53.1, 52.4, 44.1, 34.6, 31.8, 31.0, 29.8, 28.8, 24.9, 23.3, 21.0, 14.0.

B. Preparation of 3S,4aR,6S,8aR Ethyl 6-(((3S,5S)-5-(Ethoxycarbonyl)-3-hydroxypyrrolidinyl)methyl)-2-methoxycarbonyl-1,2,3,4,4a,5,6,7,8,8a-decahydroisoquinoline-3-carboxylate A mixture of trans 4-hydroxy-L-proline ethyl ester (6.5 g, 33.1 mmol), the compound of Step A above (10.0 g, 22.0 mmol), and potassium carbonate (4.6 g, 33.1 mmol) were heated at reflux in acetonitrile (22 mL) for 60 h. The reaction mixture was cooled to room temperature, and partitioned between $CH_2Cl_2$ and water. The aqueous layer was extracted two times with $CH_2Cl_2$ and the combined organics were dried over $MgSO_4$, filtered, and concentrated in vacuo. Column chromatography (50% EtOAc/hexane followed by 5% MeOH/$CH_2Cl_2$) gave 9.2 g (95%) of the desired intermediate title compound as a colorless oil:

MS (m/e): 441.3($M^+$) Calculated for $C_{22}H_{36}N_2O_7S$: Theory: C, 59.98; H, 8.24; N, 6.36. Found: C, 60.17; H, 8.23; N, 6.42.

EXAMPLE 1

Preparation of (3S,4aR,6S,8aR)-6-[[(2S,4S)-2-carboxy-4-(tetrazol-1-yl)-1-pyrrolidinyl]methyl]decahydroisoquinoline-3-carboxylic acid dihydrochloride

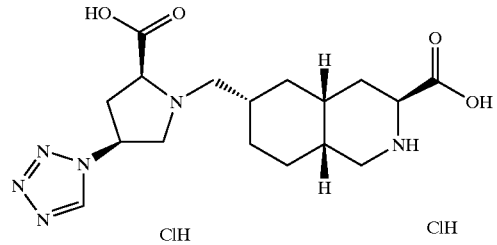

A. Preparation of Ethyl 2-methoxycarbonyl-6-[[2-ethoxycarbonyl-4-(tetrazol-1-yl)-1-pyrrolidinyl]methyl]decahydroisoquinoline-3-carboxylate:

To a 0° C. solution of 0.50 g (1.1 mmol) of material from Preparation 1, 0.087 g (1.2 mmol) of tetrazole, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Chromatography on 25 g silica gel (35% ethyl acetate/toluene) followed by elution through a 5 g Varian Bond Elut® SCX column with 2M ammonia in methyl alcohol afforded 0.17 g (31%) of the title compound.

Positive ion electrospray mass spectrum: $[M+H]^+$=493.

B. A solution of 0.17 g (0.3 mmol) of material from Example 1, step A in 5 mL of 6N hydrochloric acid was heated at 95° C. for 18 hours. The solution was concentrated in vacuo to afford 0.14 g (100%) of the title compound.

Analysis calculated for $C_{17}H_{28}Cl_2N_6O_4$*$2H_2O$: % C, 41.94; % H, 6.27; % N, 16.61. Found: % C, 41.89; % H, 6.61; % N, 17.24.

Positive ion electrospray mass spectrum: $[M+H]^+$=379.

EXAMPLE 2

Preparation of (3S,4aR,6S,8aR)-6-[[(2S,4S)-2-carboxy-4-(5-methyltetrazol-2-yl)-1-pyrrolidinyl]methyl]-decahydroisoquinoline-3-carboxylic acid dihydrochloride

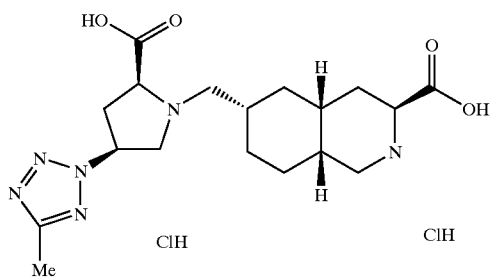

A. Preparation of Ethyl 2-methoxycarbonyl-6-[[2-ethoxycarbonyl-4-(5-methyltetrazol-2-yl)-1-pyrrolidinyl]methyl]decahydroisoquinoline-3-carboxylate:

To a 0° C. solution of 0.50 g (1.1 mmol) of material from Preparation 1, 0.10 g (1.2 mmol) of 5-methyltetrazole, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Elution through a 5 g Varian Bond Elut® SCX column with 2M ammonia in methyl alcohol followed by chromatography on 25 g silica gel (50% ethyl acetate/hexane) afforded 0.23 g (41%) of the title compound.

Positive ion electrospray mass spectrum: $[M+H]^+=507$.

B. A solution of 0.23 g (0.45 mmol) of material from Example 2, step A in 5 mL of 6N hydrochloric acid was heated at 95° C. for 18 hours. The solution was concentrated in vacuo to afford 0.16 g (89%) of the title compound.

Analysis calculated for $C_{18}H_{30}Cl_2N_6O_4*1.5H_2O*0.5HCl$: % C, 42.34; % H, 6.37; % N, 16.15. Found: % C, 42.34; % H, 6.61; % N, 16.45.

Positive ion electrospray mass spectrum: $[M+H]^+=393$.

EXAMPLE 3

Preparation of (3S,4aR,6S,8aR)-6-[[(2S,4S)-2-carboxy-4-(5-phenyltetrazol-2-yl)-1-pyrrolidinyl]methyl]-decahydroisoquinoline-3-carboxylic acid dihydrochloride

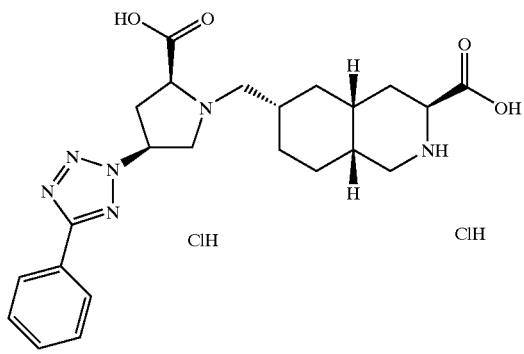

A. Preparation of Ethyl 2-methoxycarbonyl-6-[[2-ethoxycarbonyl-4-(5-phenyltetrazol-2-yl)-1-pyrrolidinyl]methyl]decahydroisoquinoline-3-carboxylate:

To a 0° C. solution of 0.50 g (1.1 mmol) of material from Preparation 1, 0.17 g (1.2 mmol) of 5-phenyltetrazole, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Elution through a 5 g Varian Bond Elut® SCX column with 2M ammonia in methyl alcohol followed by chromatography on 25 g silica gel (35% ethyl acetate/hexane) afforded 0.18 g (28%) of the title compound.

B. A solution of 0.18 g (0.31 mmol) of material from Example 3, step A in 10 mL of 6N hydrochloric acid was heated at 90° C. for 18 hours. The solution was concentrated in vacuo to afford 0.13 g (77%) of the title compound.

Analysis calculated for $C_{23}H_{32}Cl_2N_6O_4*0.5H_2O$: % C, 51.49; % H, 6.20; % N, 15.66. Found: % C, 51.10; % H 5.86; % N, 15.22.

Positive ion electrospray mass spectrum: $[M+H]^+=455$.

EXAMPLE 4

Preparation of (3S,4aR,6S,8aR)-6-[[(2S,4S)-2-carboxy-4-(5-thiomethyltetrazol-2-yl)-1-pyrrolidinyl]methyl]decahydroisoquinoline-3-carboxylic acid dihydrochloride

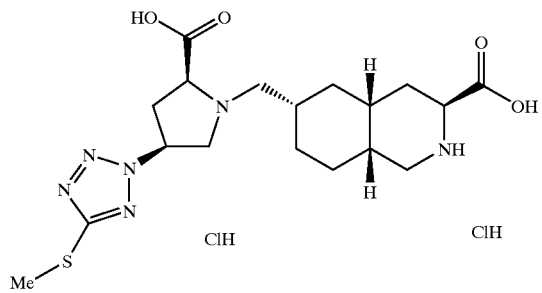

A. Preparation of Ethyl 2-methoxycarbonyl-6-[[2-ethoxycarbonyl-4-(5-thiomethyltetrazol-2-yl)-1-pyrrolidinyl]methyl]decahydroisoquinoline-3-carboxylate:

To a 0° C. solution of 0.50 g (1.1 mmol) of material from Preparation 1, 0.14 g (1.2 mmol) of 5-(methylthio)-tetrazole, and 0.33 g (1.2 mmol) of triphenylphosphine in 5 mL of dry tetrahydrofuran was added 0.24 g (1.2 mmol) of diisopropylazidodicarboxylate dropwise. The mixture was stirred at room temperature for 18 hours, and then concentrated in vacuo. Elution through a 5 g Varian Bond Elut® SCX column with 2M ammonia in methyl alcohol followed by chromatography on 25 g silica gel (35% ethyl acetate/hexane) afforded 0.3 g (51%) of the title compound.

Positive ion electrospray mass spectrum: $[M+H]^+=539$.

B. A solution of 0.3 g (0.55 mmol) of material from Example 4, step A in 10 mL of 6N hydrochloric acid was heated at 95° C. for 18 hours. The solution was concentrated in vacuo to afford 0.16 g (89%) of the title compound.

Analysis calculated for $C_{18}H_{30}Cl_2N_6O_4S*2.0H_2O$: % C, 40.53; % H, 6.42; % N, 15.75. Found: % C, 40.98; % H, 5.81; % N, 15.84.

Positive ion electrospray mass spectrum: $[M+H]^+=425$.

EXAMPLE 5

Preparation of (3S,4aR,6S,8aR)-6-[[(2S,4S)-2-carboxy-4-(N-methanesulfonamido)-1-pyrrolidinyl]methyl]-decahydroisoquinoline-3-carboxylic acid dihydrochloride

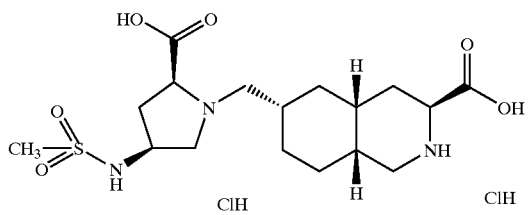

A. Preparation of N-t-butoxycarbonyl-methylsulfonamide:

To a solution of 15.0 g (157 mmol) of methanesulfonamide, 17.6 g (173 mmol) of triethylamine, and 1.9 g (15 mmol) of 4-dimethylaminopyridine in 200 mL of dichloromethane was added 37.9 g (173 mmol) of di-tert-butyl dicarbonate. The reaction was stirred at ambient temperature for 18 hours and was then washed with a 200 mL of a 10% aqueous solution of sodium hydrogen sulfate and 200 mL of brine. The organic layer was removed and dried over magnesium sulfate and concentrated under vacuo to afford 26.1 g (85%) of the title compound.

B. Preparation of Ethyl 2-methoxycarbonyl-6-[[-2-ethoxycarbonyl-4-(N-methanesulfonamido)-1-pyrrolidinyl]methyl]decahydroisoquinoline-3-carboxylate:

To a 0° C. solution of 0.50 g (1.1 mmol) of material from Preparation 1, 0.24 g (1.2 mmol) material from Example 5, step A, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Elution through a 5 g Varian Bond Elut® SCX column with 2M ammonia in methyl alcohol followed by chromatography on 25 g silica 2.5 gel (35% ethyl acetate/hexane) afforded 0.25 g (37%) of the title compound.

Positive ion electrospray mass spectrum: [M+H]$^+$=618.

C. A solution of 0.25 g (0.40 mmol) of material from Example 5, step B in 5 mL of 6N hydrochloric acid was heated at 95° C. for 18 hours. The solution was concentrated in vacuo to afford 0.14 g (90%) of the title compound.

Analysis calculated for $C_{17}H_{31}Cl_2N_3O_6S$*1.5$H_2O$: % C, 40.56; % H, 6.80; % N, 8.35. Found: % C, 40.53; % H, 6.44; % N, 8.11.

Positive ion electrospray mass spectrum: [M+H]$^+$=404.

EXAMPLE 6

Preparation of (3S,4aR,6S,8aR)-6-[[(2S,4S)-2-carboxy-4-(N-benzenesulfonamido)-1-pyrrolidinyl]methyl]decahydroisoquinoline-3-carboxylic acid dihydrochloride

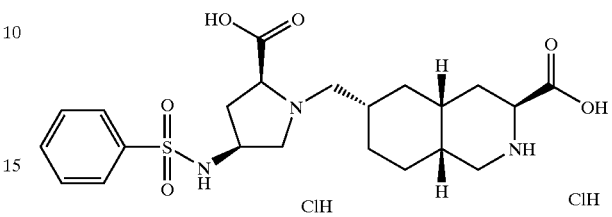

A. Preparation of N-t-butoxycarbonyl-benzenesulfonamide:

To a solution of 5.0 g (31.8 mmol) of benzenesulfonamide, 3.5 g (35 mmol) of triethylamine, and 0.4 g (3.1 mmol) of 4-dimethylaminopyridine in 100 mL of dichloromethane was added 7.6 g (35 mmol) of di-tert-butyl dicarbonate. The reaction was stirred at ambient temperature for 18 hours and was then washed with a 100 mL of a 10% aqueous solution of sodium hydrogen sulfate and 100 mL of brine. The organic layer was removed and dried over magnesium sulfate and concentrated under vacuo to afford 7.1 g (87%) of the title compound.

B. Preparation of Ethyl 2-methoxycarbonyl-6-[[2-ethoxycarbonyl-4-(N-benzenesulfonamido)-1-pyrrolidinyl]methyl]decahydroisoquinoline-3-carboxylate:

To a 0° C. solution of 0.50 g (1.1 mmol) of material from Preparation 1, 0.31 g (1.2 mmol) of material from Example 6, step A, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Elution through a 5 g Varian Bond Elut® SCX column with 2M ammonia in methyl alcohol followed by chromatography on 25 g silica gel (35% ethyl acetate/hexane) afforded 0.24 g (32%) of the title compound.

Positive ion electrospray mass spectrum: [M+H]$^+$=680.

C. A solution of 0.24 g (0.35 mmol) of material from Example 6, step B in 5 mL of 5N hydrochloric acid was heated at 95° C. for 18 hours. The solution was concentrated in vacuo to afford 0.19 g (90%) of the title compound.

Analysis calculated for $C_{22}H_{33}Cl_2N_3O_6S$*1.0$H_2O$: % C, 47.48; % H, 6.34; % N, 7.55. Found: % C, 47.43; % H, 6.63; % N, 7.71.

Positive ion electrospray mass spectrum: [M+H]$^+$=466.

EXAMPLE 7

Preparation of (3S,4aR,6S,8aR)-6-[[(2S,4S)-2-carboxy-4-(N-benzylsulfonamido)-1-pyrrolidinyl]methyl]decahydroisoquinoline-3-carboxylic acid dihydrochloride

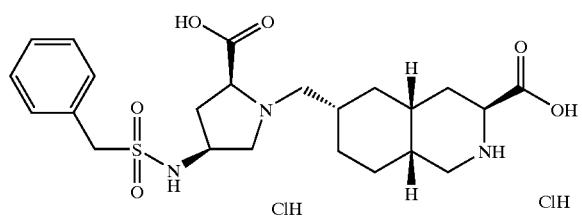

A. Preparation of N-t-butoxycarbonyl-benzylsulfonamide:

To a solution of 5.0 g (29.2 mmol) of α-toluenesulfonamide, 3.2 g (32.1 mmol) of triethylamine, and 0.35 g (2.9 mmol) of 4-dimethylaminopyridine in 100 mL of dichloromethane and was added 7.0 g (32.1 mmol) of di-tert-butyl dicarbonate. The reaction was stirred at ambient temperature for 18 hours and was then washed with a 100 mL of a 10% aqueous solution of sodium hydrogen sulfate and 100 mL of brine. The organic layer was removed and dried over magnesium sulfate and concentrated under vacuo to afford 7.9 g (100%) of the title compound.

B. Preparation of Ethyl 2-methoxycarbonyl-6-[[2-ethoxycarbonyl-4-(N-benzylsulfonamido)-1-pyrrolidinyl]methyl]decahydroisoquinoline-3-carboxylate:

To a 0° C. solution of 0.50 g (1.1 mmol) of material from Preparation 1, 0.32 g (1.2 mmol) material from Example 7, step A, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Elution through a 5 g Varian Bond Elut® SCX column with 2M ammonia in methyl alcohol afforded 0.5 g (65%) of the title compound.

Positive ion electrospray mass spectrum: $[M+H]^+=694$.

C. A solution of 0.5 g (0.7 mmol) of material from Example 7, step B in 5 mL of 5N hydrochloric acid was heated at 95° C. for 18 hours. The solution was concentrated in vacuo to afford 0.4 g (100%) of the title compound.

Analysis calculated for $C_{23}H_{35}Cl_2N_3O_6S*0.5H_2O$: % C, 49.20; % H, 6.46; % N, 7.48. Found: % C, 49.34; % H, 6.66; % N, 7.49.

Positive ion electrospray mass spectrum: $[M+H]^+=480$.

EXAMPLE 8

Preparation of (3S,4aR,6S,8aR)-6-[[(2S,4S)-2-carboxy-4-(N-benzyl-N-benzylsulfonamido-1-pyrrolidinyl]methyl]decahydroisoquinoline-3-carboxylic acid dihydrochloride

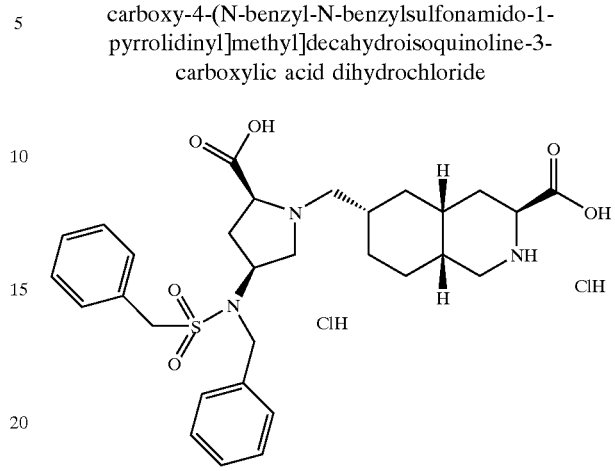

A. Preparation of Ethyl 2-methoxycarbonyl-6-[[2-ethoxycarbonyl-4-(N-benzylsulfonamido)-1-pyrrolidinyl]methyl]decahydroisoquinoline-3-carboxylate:

A solution of 0.4 g (0.6 mmol) of material from Example 7, step B in 5 mL of 1N hydrochloric acid in ethyl acetate was stirred at room temperature for 18 hours. The mixture was diluted with 5 mL of ethyl acetate and washed with 5 mL of sat. sodium bicarbonate. The organic layer was separated and the aqueous layer was extracted one time with 5 mL of ethyl acetate. The combined organics were dried ($MgSO_4$), filtered and concentrated in vacuo to afford 0.2 g (56%) of the title compound Positive ion electrospray mass spectrum: $[M+H]^+=549$.

B. A solution of 0.15 g (0.25 mmol) of material from Example 8, step A in 5 mL of tetrahydrofuran was added 0.26 mL (0.26 mmol) of 1M sodium bis(trimethylsilyl)amide dropwise. The mixture was stirred 30 min then 0.045 g (0.25 mmol) of benzylbromide was added. The mixture was stirred for 18 hours at 65° C. and then allowed to cool to room temperature. To the reaction was added 5 mL of water and 5 mL of diethyl ether. The organic layer was separated and the aqueous layer was extracted three times with 5 mL each of diethyl ether. The combined organics were dried ($MgSO_4$), filtered and concentrated in vacuo. Chromatography on 15 g silica gel (35% ethyl acetate/hexane) afforded 0.052 g (30%) of the title compound.

Positive ion electrospray mass spectrum: $[M+H]^+=684$.

C. A solution of 0.052 g (0.076 mmol) of material from Example 8, step B in 2 mL of 5N hydrochloric acid was heated at 95° C. for 18 hours. The solution was concentrated in vacuo to afford 0.030 g (61%) of the title compound.

Analysis calculated for $C_{30}H_{41}Cl_2N_3O_6S*2.0H_2O*0.5HCl$: % C, 51.71; % H, 6.58; % N, 6.03. Found: % C, 51.54; % H 6.23; % N, 5.95.

Positive ion electrospray mass spectrum: $[M+H]^+=570$.

EXAMPLE 9

Preparation of (3S,4aR,6S,8aR)-6-[[(2S,4S)-2-carboxy-4-(N-methyl-N-benzylsulfonamido-1-pyrrolidinyl]methyl]decahydroisoquinoline-3-carboxylic acid dihydrochloride

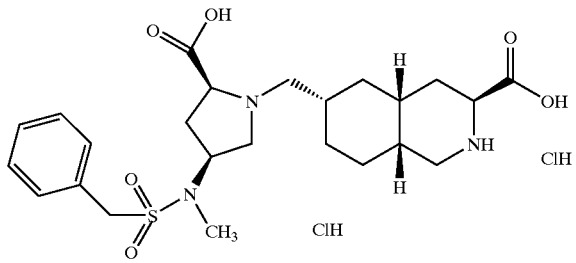

A. A solution of 0.30 g (0.51 mmol) of material from Example 8, step A in 5 mL of tetrahydrofuran was added 0.53 mL (0.53 mmol) of 1M sodium bis(trimethylsilyl)amide dropwise. The mixture was stirred 30 min then 0.072 g (0.51 mmol) of methyl iodide was added. The mixture was stirred for 2 hours at room temperature and then 0.1 g (0.71 mmol) of methyl iodide was added and the mixture was stirred for 2 hours. To the reaction was added 5 mL of water and 5 mL of diethyl ether. The organic layer was separated and the aqueous layer was extracted three times with 5 mL each of diethyl ether. The combined organics were dried (MgSO$_4$), filtered and concentrated in vacuo. Chromatography on 15 g silica gel (35% ethyl acetate/hexane) afforded 0.030 g (10%) of the title compound.

Positive ion electrospray mass spectrum: [M+H]$^+$=608.

B. A solution of 0.030 g (0.050 mmol) of material from Example 9, step A in 5 mL of 5N hydrochloric acid was heated at 95° C. for 18 hours. The solution was concentrated in vacuo to afford 0.017 g (61%) of the title compound.

$^1$H NMR (400 MHz, D$_2$O) δ 7.32 (5H m), δ 4.42 (1H s), δ 4.35 (2H s), δ 3.87–3.77 (1H m), δ 3.17–2.92 (3H m), δ 2.75 (1H m), δ 2.70 (3H s) δ 2.55 (1H m), δ 2.20 (1H m), δ 2.07–1.82 (4H m), δ 1.40–1.19 (3H m), δ 0.87 (1H m), δ 0.75 (1H t).

Positive ion electrospray mass spectrum: [M+H]$^+$=494.

EXAMPLE 10

Preparation of (3S,4aR,6S,8aR)-6-[[(2S,4S)-2-carboxy-4-(N-trifluoromethanesulfonamido-1-pyrrolidinyl]methyl]decahydroisoquinoline-3-carboxylic acid dihydrochloride

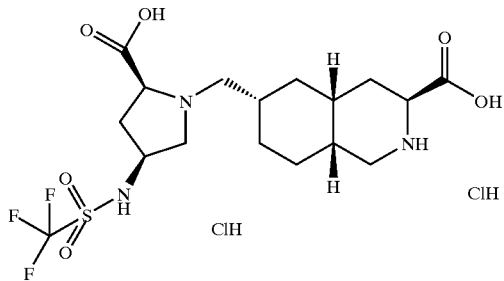

A. Preparation of N-t-butoxycarbonyl-trifluoromethanesulfonamide:

To a solution of 5.0 g (33.5 mmol) of trifluoromethanesulfonamide, 3.7 g (36.9 mmol) of triethylamine, and 0.40 g (3.3 mmol) of 4-dimethylaminopyridine in 100 mL of dichloromethane and was added 8.1 g (36.9 mmol) of di-tert-butyl dicarbonate. The reaction was stirred at ambient temperature for 18 hours and was diluted with 100 mL of ethyl acetate and washed with a 100 mL of a 10% aqueous solution of sodium hydrogen sulfate and 100 mL of brine. The organic layer was removed and dried over magnesium sulfate and concentrated under vacuo. The resulting white solid was suspended in hexane and filtered to afford 5.8 g (69%) of the title compound.

B. Preparation of Ethyl 2-methoxycarbonyl-6-[[2-carboxy-4-(N-t-butoxycarbonyl-N-trifluoromethanesulfonamido)-1-pyrrolidinyl]methyl]decahydroisoquinoline-3-carboxylate:

To a 0° C. solution of 0.30 g (0.70 mmol) of material from Preparation 1, 0.20 g (0.80 mmol) material from Example 10, step A, and 0.20 g (0.80 mmol) of triphenylphosphine in 5 mL of dry tetrahydrofuran was added 0.14 g (0.80 mmol) of diethylazodicarboxylate dropwise. The mixture was stirred at room temperature for 48 hours, and then concentrated in vacuo. Elution through a 5 g Varian Bond Elut® SCX column with 2M ammonia in methyl alcohol followed by chromatography on 10 g of silica gel gel (35% ethyl acetate/hexane) afforded 0.15 g (37%) of the title compound.

Positive ion electrospray mass spectrum: [M+H]$^+$=572.

C. A solution of 0.15 g (0.3 mmol) of material from Example 10, step B in 5 mL of 5N hydrochloric acid was heated at 95° C. for 5 hours. The solution was concentrated in vacuo to afford 0.13 g (82%) of the title compound.

Analysis calculated for C$_{17}$H$_{28}$Cl$_2$F$_3$N$_3$O$_6$S: % C, 38.50; % H, 5.32; % N, 7.92. Found: % C, 39.32; % H, 5.40; % N, 7.92.

Positive ion electrospray mass spectrum: [M+H]$^+$=458.

EXAMPLE 11

Preparation of (3S,4aR,6S,8aR)-6-[[(2S,4S)-2-carboxy-4-(N-(2-methylpropane)sulfonamido-1-pyrrolidinyl]methyl]decahydroisoquinoline-3-carboxylic acid dihydrochloride

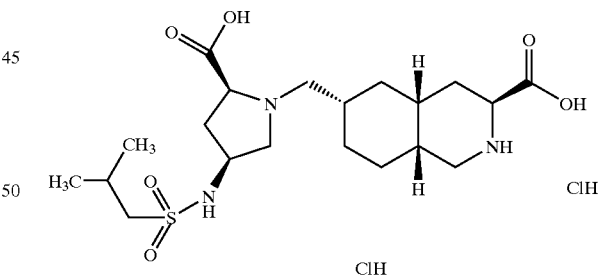

A. Preparation of N-t-butoxycarbonyl-2-methyl-propanesulfonamide:

To a solution of 2.5 g (18.2 mmol) of 2-methyl-propanesulfonamide, 2.0 g (20.0 mmol) of triethylamine, and 0.20 g (1.8 mmol) of dimethylaminopyridine in 60 mL of dichloromethane was added 4.3 g (20.0 mmol) of di-tert-butyl dicarbonate. The reaction was stirred at ambient temperature for 18 hours and was diluted with 100 mL of ethyl acetate and washed with a 60 mL of a 10% aqueous solution of sodium hydrogen sulfate and 60 mL of brine. The organic layer was removed and dried over magnesium sulfate and concentrated under vacuo. Chromatography on 75 g silica gel (35% ethyl acetate/hexane) afforded 2.0 g (46%) of the title compound.

B. Preparation of Ethyl 2-methoxycarbonyl-6-[[2-ethoxycarbonyl-4-(N-t-butoxycarbonyl-N-(2-methylpropane)sulfonamido)-1-pyrrolidinyl]methyl] decahydroisoquinoline-3-carboxylate:

To a 0° C. solution of 0.50 g (1.1 mmol) of material from Preparation 1, 0.30 g (1.2 mmol) material from Example 11, step A, and 0.30 g (1.2 mmol) of triphenylphosphine in 5 mL of dry tetrahydrofuran was added 0.20 g (1.2 mmol) of diethylazodicarboxylate dropwise. The mixture was stirred at room temperature for 48 hours, and then concentrated in vacuo. Elution through a 5 g Varian Bond Elut® SCX column with 2M ammonia in methyl alcohol afforded 0.55 g (75%) of the title compound.

Positive ion electrospray mass spectrum: $[M+H]^+=660$.

C. A solution of 0.20 g (0.30 mmol) of material from Example 11, step B in 12 mL of 5N hydrochloric acid was heated at 95° C. for 18 hours. The solution was concentrated in vacuo to afford 0.13 g (82%) of the title compound.

Analysis calculated for $C_{20}H_{37}Cl_2N_3O_6S*0.5H_2O$: % C, 45.54; % H, 7.26; % N, 7.97. Found: % C, 45.51; % H, 6.97; % N, 9.06.

Positive ion electrospray mass spectrum: $[M+H]^+=446$.

EXAMPLE 12 (480632)

Preparation of (3S,4aR,6S,8aR)-6-[[(2S,4S)-2-carboxy-4-(N-ethanesulfonamido)-1-pyrrolidinyl]methyl]decahydroisoquinoline-3-carboxylic acid

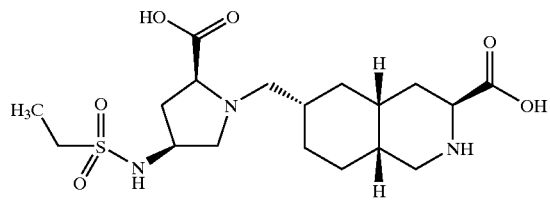

A. Preparation of Ethyl 2-methoxycarbonyl-6-[[2-ethoxycarbonyl-4-(methanesulfonato)-1-pyrrolidinyl]methyl]decahydroisoquinoline-3-carboxylate:

To a 0° C. solution of 2.6 g (5.9 mmol) of material from Preparation 1, 0.6 g (6.5 mmol) of triethylamine in 20 mL of dichloromethane was added 0.7 g (6.5 mmol) of methane sulfonyl chloride. The mixture was stirred at room temperature for 4 hours and was then diluted with 20 mL of water. The organic layer was removed and the aqueous layer was extracted three times with 10 mL of dichloromethane. The organic layers were combined and dried over magnesium sulfate, filtered, and concentrated under vacuo. Chromatography on 150 g silica gel (50% ethyl acetate/hexane) afforded 1.8 g (59%) of the title compound.

Positive ion electrospray mass spectrum: $[M+H]^+=519$.

B. Preparation of Ethyl 2-methoxycarbonyl-6-[[2-ethoxycarbonyl-4-azido-1-pyrrolidinyl]methyl] decahydroisoquinoline-3-carboxylate:

A solution of 1.8 g (3.5 mmol) of material from Example 12, step A and 0.67 g (10.4 mmol) of sodium azide in 10 mL of dry dimethylsulfoxide was heated at 80° C. for 18 hours. The mixture was cooled and quenched with 20 mL brine. The aqueous mixture was extracted four times with 10 mL of ethyl acetate. The organic layers were combined and dried over magnesium sulfate, filtered, and concentrated under vacuo. Chromatography on 100 g of silica gel (35% ethyl acetate/hexane) afforded 1.3 g (80%) of the title compound.

Positive ion electrospray mass spectrum: $[M+H]^+=466$.

C. Preparation of Ethyl 2-methoxycarbonyl-6-[[2-ethoxycarbonyl-4-amino-1-pyrrolidinyl]methyl] decahydroisoquinoline-3-carboxylate:

A solution of 1.3 g (2.8 mmol) of material from Example 12, step B and 0.8 g (3.1 mmol) of triphenylphosphine in 10 ml of tetrahydrofuran and 200 mL of water was stirred at room temperature for 18 hours. The mixture was diluted with 10 mL of brine and 10 ml of diethyl ether. The organic layer was removed and the aqueous layer was extracted three times with 10 mL of diethyl ether. The organic layers were combined and dried over magnesium sulfate, filtered and concentrated under vacuo. The residue was suspended in 10 mL of diethyl ether and 1N hydrochloric acid in diethyl ether was added dropwise with stirring. The resulting solid was filtered and washed with diethyl ether. The solid was eluted through a 10 g Varian Bond Elut® SCX column with 2M ammonia in methyl alcohol to afford 0.9 g (73%) of the title compound.

Positive ion electrospray mass spectrum: $[M+H]^+=440$.

D. Preparation of Ethyl 2-methoxycarbonyl-6-[[2-ethoxycarbonyl-4-(N-ethanesulfonamido)-1-pyrrolidinyl] methyl]decahydroisoquinoline-3-carboxylate:

To a solution of 0.3 g (0.7 mmol) of material from Example 12, step C, and 0.1 g (0.8 mmol) of 1,8-diazabicyclo[5.4.0]undec-7-ene in 3 mL of chloroform was added 0.1 g (0.8 mmol) of ethane sulfonyl chloride. The mixture was stirred at room temperature for 18 hours and was then diluted with 5 mL of brine and 5 mL of chloroform. The organic layer was removed dried over magnesium sulfate, filtered, and concentrated under vacuo. Chromatography on 60 g silica gel (50% ethyl acetate/hexane) afforded 0.1 g (27%) of the title compound.

Positive ion electrospray mass spectrum: $[M+H]^+=532$.

E. A solution of 0.10 g (0.20 mmol) of material from Example 12, step D in 2 mL of 6N hydrochloric acid was heated at 95° C. for 18 hours. The solution was concentrated in vacuo. Elution through a 2 g Varian Bond Elut® SCX column with 2M ammonia in methyl alcohol afforded 0.05 g (60%) of the title compound.

$^1$H NMR (400 MHz, $D_2O$) δ 4.16 (1H m), δ 3.90 (1H t), δ 3.64 (1H dd), δ 3.50 (2H dd), δ 3.37 (1H dd), δ 3.10–2.87 (9H m), δ 2.62 (3H m) δ 2.00–1.87 (4H m), δ 1.82–1.65 (2H m), δ 1.52 (4H m), δ 1.17 (4H t).

Positive ion electrospray mass spectrum: $[M+H]^+=418$.

EXAMPLE 13

Preparation of (3S,4aR,6S,8aR)-6-[[(2S,4S)-2-carboxy-4-(N-2-propanesulfonamido)-1-pyrrolidinyl]methyl]decahydroisoquinoline-3-carboxylic acid

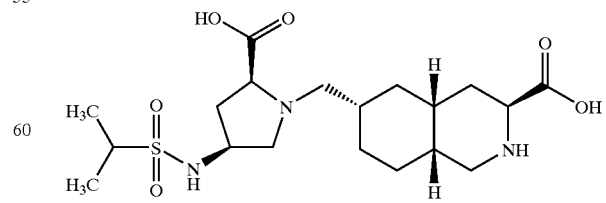

A. Preparation of Ethyl 2-methoxycarbonyl-6-[[2-ethoxycarbonyl-4-(N-2-propanesulfonamido)-1-pyrrolidinyl]methyl]decahydroisoquinoline-3-carboxylate:

To a solution of 0.3 g (0.7 mmol) of material from Example 12, step C, and 0.2 g (2.2 mmol) of triethylamine in 10 mL of dichloromethane was added 0.3 g (2.2 mmol) of 2-propane sulfonyl chloride. The mixture was stirred at room temperature for 18 hours and was then diluted with 5 mL of 10% aqueous sodium hydrogen sulfate. The organic layer was removed dried over magnesium sulfate, filtered, and concentrated under vacuo. Chromatography on 60 g silica gel (50% ethyl acetate/hexane) afforded 0.077 g (20%) of the title compound.

Positive ion electrospray mass spectrum: $[M+H]^+=546$.

B. A solution of 0.077 g (0.14 mmol) of material from Example 13, step A in 3 mL of 5N hydrochloric acid was heated at 95° C. for 18 hours. The solution was concentrated in vacuo. Elution through a 2 g Varian Bond Elut® SCX column with 2M ammonia in methyl alcohol afforded 0.044 g (60%) of the title compound.

$^1$H NMR (250 MHz, D$_2$O) δ 4.30 (1H m), δ 4.00 (1H t), δ 3.61 (1H dd), δ3.49 (1H dd), δ 3.35 (1H t), δ 3.21–3.00 (4H m), δ 2.76 (1H m) δ 2.16–1.94 (4H m), δ 1.93–1.70 (3H m), δ 1.61–1.49 (3H m), δ 1.30 (6H m), δ 0.97 (2H, m).

Positive ion electrospray mass spectrum: $[M+H]^+=432$.

EXAMPLE 14

Preparation of (3S,4aR,6S,8aR)-6-[[(2S,4S)-2-carboxy-4-(N-4-chlorobenzenesulfonamido)-1-pyrrolidinyl]methyl]decahydroisoquinoline-3-carboxylic acid dihydrochloride

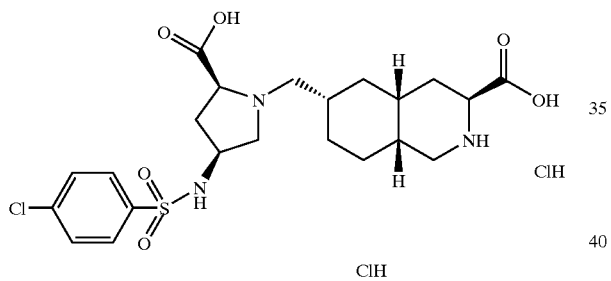

A. Preparation of 4-chlorobenzenesulfonamide:

To a solution of 10 g (47.4 mmol) of 4-chlorobenzenesulfonyl chloride in 60 mL of dichloromethane was added 60 mL of concentrated ammonium hydroxide that had been cooled to 0° C. before being added dropwise. The mixture was stirred for 3 hours at room temperature and then the organic layer was removed. The aqueous layer was extracted three times with 20 mL of diethyl ether and the combined organic layers were dried over magnesium sulfate, filtered, and concentrated under vacuo to afford 8.5 g (94%) of the title compound.

Negative ion electrospray mass spectrum: $[M-H]^-=190$.

B. Preparation of N-t-butoxycarbonyl-4-chlorobenzenesulfonamide:

To a solution of 6.1 g (31.8 mmol) of material from Example 14, step A, 3.5 g (35 mmol) of triethylamine, and 0.4 g (3.1 mmol) of 4-dimethylaminopyridine in 100 mL of dichloromethane was added 7.6 g (35 mmol) of di-tert-butyl dicarbonate. The reaction was stirred at ambient temperature for 18 hours and was then washed with a 50 mL of a 10% aqueous solution of sodium hydrogen sulfate and 50 mL of brine. The organic layer was removed and dried over magnesium sulfate, filtered, and concentrated under vacuo. The resulting solid was suspended in hexane and filtered and washed with hexane to afford 8.0 g (86%) of the title compound.

Negative ion electrospray mass spectrum: $[M-H]^-=290$.

C. Preparation of Ethyl 2-methoxycarbonyl-6-[[2-ethoxycarbonyl-4-(N-4-chlorobenzenesulfonamido)-1-pyrrolidinyl]methyl]decahydroisoquinoline-3-carboxylate:

To a 0° C. solution of 0.50 g (1.1 mmol) of material from Preparation 1, 0.35 g (1.2 mmol) material from Example 14, step B, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Elution through a 5 g Varian Bond Elut® SCX column with 2M ammonia in methyl alcohol afforded 0.52 g (66%) of the title compound.

Positive ion electrospray mass spectrum: $[M]^+=714$.

D. A solution of 0.20 g (0.30 mmol) of material from Example 14, step C in 12 mL of 5N hydrochloric acid was heated at 120° C. for 8 hours. The solution was concentrated in vacuo and the resulting solid was suspended in water and filtered and washed with water and then washed with diethyl ether to afford 0.052 g (33%) of the title compound.

Analysis calculated for $C_{22}H_{32}Cl_3N_3O_6S$: % C, 46.12; % H, 5.63; % N, 7.33. Found: % C, 45.90; % H, 5.48; % N, 7.16.

Positive ion electrospray mass spectrum: $[M]^+=500$.

EXAMPLE 15

Preparation of (3S,4aR,6S,8aR)-6-[[(2S,4S)-2-carboxy-4-(N-3-chlorobenzenesulfonamido)-1-pyrrolidinyl]methyl]decahydroisoquinolne-3-carboxylic acid dihydrochloride

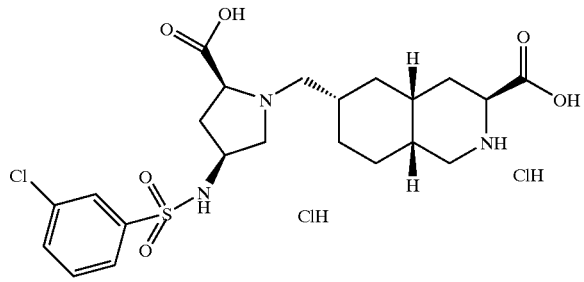

A. Preparation of 3-chlorobenzenesulfonamide:

To a solution of 10 g (47.4 mmol) of 4-chlorobenzenesulfonyl chloride in 60 mL of dichloromethane was added 60 mL of concentrated ammonium hydroxide that had been cooled to 0° C. before being added dropwise. The mixture was stirred for 3 hours at room temperature and then the organic layer was removed. The aqueous layer was extracted three times with 20 mL of diethyl ether and the combined organic layers were dried over magnesium sulfate, filtered, and concentrated under vacuo to afford 7.4 g (81%) of the title compound.

Negative ion electrospray mass spectrum: $[M-H]^-=190$.

B. Preparation of N-t-butoxycarbonyl-3-chlorobenzenesulfonamide:

To a solution of 6.1 g (31.8 mmol) of material from Example 15, step A, 3.5 g (35 mmol) of triethylamine, and 0.4 g (3.1 mmol) of 4-dimethylaminopyridine in 100 mL of dichloromethane was added 7.6 g (35 mmol) of di-tert-butyl dicarbonate. The reaction was stirred at ambient temperature for 18 hours and was then washed with a 50 mL of a 10% aqueous solution of sodium hydrogen sulfate and 50 mL of brine. The organic layer was removed and dried over magnesium sulfate, filtered, and concentrated under vacuo. The resulting solid was suspended in hexane and filtered and washed with hexane to afford 7.6 g (82%) of the title compound.

Negative ion electrospray mass spectrum: [M−H]⁻=290.

C. Preparation of Ethyl 2-methoxycarbonyl-6-[[2-ethoxycarbonyl-4-(N-3-chlorobenzenesulfonamido)-1-pyrrolidinyl]methyl]decahydroisoquinoline-3-carboxylate:

To a 0° C. solution of 0.50 g (1.1 mmol) of material from Preparation 1, 0.35 g (1.2 mmol) material from Example 15, step B, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Elution through a 5 g Varian Bond Elut® SCX column with 2M ammonia in methyl alcohol followed by chromatography on 50 g silica gel (35% ethyl acetate/hexane) afforded 0.57 g (72%) of the title compound.

Positive ion electrospray mass spectrum: [M+H]⁺=715.

D. A solution of 0.20 g (0.30 mmol) of material from Example 15, step C in 10 mL of 5N hydrochloric acid was heated at 100° C. for 18 hours. The solution was concentrated in vacuo to afford 0.126 g (33%) of the title compound.

Analysis calculated for $C_{22}H_{32}Cl_3N_3O_6S$: % C, 46.12; % H, 5.63; % N, 7.33. Found: % C, 46.24; % H, 5.75; % N, 7.32.

Positive ion electrospray mass spectrum: [M]⁺=500.

EXAMPLE 16

Preparation of (3S,4aR,6S,8aR)-6-[[(2S,4S)-2-carboxy-4-(N-2-chlorobenzenesulfonamido)-1-pyrrolidinyl]methyl]decahydroisoquinoline-3-carboxylic acid dihydrochloride

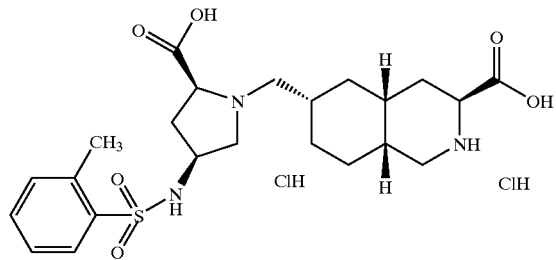

A. Preparation of 2-chlorobenzenesulfonamide:

To a solution of 5 g (23.7 mmol) of 2-chlorobenzenesulfonyl chloride in 30 mL of dichloromethane was added 30 mL of concentrated ammonium hydroxide that had been cooled to 0° C. before being added dropwise. The mixture was stirred for 3 hours at room temperature and then the organic layer was removed. The aqueous layer was extracted three times with 20 mL of diethyl ether and the combined organic layers were dried over magnesium sulfate, filtered, and concentrated under vacuo to afford 3.0 g (66%) of the title compound.

Negative ion electrospray mass spectrum: [M−H]⁻=190.

B. Preparation of N-t-butoxycarbonyl-2-chlorobenzenesulfonamide:

To a solution of 3.0 g (15.6 mmol) of material from Example 16, step A, 1.7 g (17.2 mmol) of triethylamine, and 0.2 g (1.5 mmol) of 4-dimethylaminopyridine in 50 mL of dichloromethane was added 3.8 g (17.2 mmol) of di-tert-butyl dicarbonate. The reaction was stirred at ambient temperature for 18 hours and was then washed with a 50 mL of a 10% aqueous solution of sodium hydrogen sulfate and 50 mL of brine. The organic layer was removed and dried over magnesium sulfate, filtered, and concentrated under vacuo to afford 3.6 g (79%) of the title compound.

Negative ion electrospray mass spectrum: [M−H]⁻=290.

C. Preparation of Ethyl 2-methoxycarbonyl-6-[[2-ethoxycarbonyl-4-(N-2-chlorobenzenesulfonamido)-1-pyrrolidinyl]methyl]decahydroisoquinoline-3-carboxylate:

To a 0° C. solution of 0.50 g (1.1 mmol) of material from Preparation 1, 0.35 g (1.2 mmol) material from Example 16, step B, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Elution through a 5 g Varian Bond Elut® SCX column with 2M ammonia in methyl alcohol followed by chromatography on 20 g silica gel (50% ethyl acetate/hexane) afforded 0.34 g (43%) of the title compound.

Positive ion electrospray mass spectrum: [M+H]⁺=715.

D. A solution of 0.34 g (0.50 mmol) of material from Example 16, step C in 10 mL of 5N hydrochloric acid was heated at 100° C. for 18 hours. The solution was concentrated in vacuo. The resulting solid was suspended in 10 mL of 1:1 acetone/diethyl ether and heated at 40° C. for 1 hour. The solid was filtered and washed with diethyl ether to afford 0.25 g (87%) of the title compound.

Analysis calculated for $C_{22}H_{32}Cl_3N_3O_6S$: % C, 46.12; % H, 5.63; % N, 7.33. Found: % C, 46.83; % H, 5.87; % N, 7.37.

Positive ion electrospray mass spectrum: [M]⁺=500.

EXAMPLE 17

Preparation of (3S,4aR,6S,8aR)-6-[[(2S,4S)-2-carboxy-4-(N-3-methylbenzenesulfonamido)-1-pyrrolidinyl]methyl]decahydroisoquinoline-3-carboxylic acid dihydrochloride

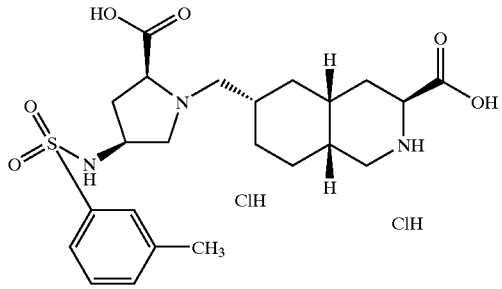

A. Preparation of 3-methylbenzenesulfonamide:

To a solution of 10 g (52.4 mmol) of 3-methylbenzenesulfonyl chloride in 60 mL of dichloromethane was added 60 mL of concentrated ammonium hydroxide that had been cooled to 0° C. before being added dropwise. The mixture was stirred for 3 hours at room temperature and then the organic layer was removed. The aqueous layer was extracted three times with 20 mL of diethyl ether and the combined organic layers were dried over magnesium sulfate, filtered, and concentrated under vacuo to afford 8.0 g (89%) of the title compound.

Negative ion electrospray mass spectrum: [M−H]⁻=170.

B. Preparation of N-t-butoxycarbonyl-3-methylbenzenesulfonamide:

To a solution of 5.0 g (29.2 mmol) of material from Example 17, step A, 3.2 g (32.1 mmol) of triethylamine, and 0.35 g (2.9 mmol) of 4-dimethylaminopyridine in 100 mL of dichloromethane was added 7.0 g (32.1 mmol) of di-tenbutyl dicarbonate. The reaction was stirred at ambient temperature for 18 hours and was then washed with a 50 mL of a 10% aqueous solution of sodium hydrogen sulfate and 50 mL of brine. The organic layer was removed and dried over magnesium sulfate, filtered, and concentrated under vacuo to afford 6.7 g (84%) of the title compound.

Negative ion electrospray mass spectrum: [M−H]⁻=270.

C. Preparation of Ethyl 2-methoxycarbonyl-6-[[2-ethoxycarbonyl-4-(N-3-methylbenzenesulfonamido)-1-pyrrolidinyl]methyl]decahydroisoquinolne-3-carboxylate:

To a 0° C. solution of 0.50 g (1.1 mmol) of material from Preparation 1, 0.35 g (1.2 mmol) material from Example 17, step B, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Elution through a 5 g Varian Bond Elut® SCX column with 2M ammonia in methyl alcohol followed by chromatography on 50 g silica gel (40% ethyl acetate/hexane) afforded 0.4 g (52%) of the title compound.

Positive ion electrospray mass spectrum: [M+H]⁺=694.

D. A solution of 0.4 g (0.60 mmol) of material from Example 17, step C in 10 mL of 5N hydrochloric acid was heated at 100° C. for 18 hours. The solution was concentrated in vacuo. The resulting solid was suspended in 10 mL of 1:1 acetone/diethyl ether and heated at 40° C. for 1 hour. The solid was filtered and washed with diethyl ether to afford 0.198 g (60%) of the title compound.

Analysis calculated for $C_{23}H_{35}Cl_2N_3O_6S$: % C, 50.00; % H, 6.39; % N, 7.61. Found: % C, 50.05; % H, 6.47; % N, 7.66.

Positive ion electrospray mass spectrum: [M]⁺=480.

EXAMPLE 18

Preparation of (3S,4aR,6S,8aR)-6-[[(2S,4S)-2-carboxy-4-(N-4-methylbenzenesulfonamido)-1-pyrrolidinyl]methyl]decahydroisoquinolne-3-carboxylic acid dihydrochloride

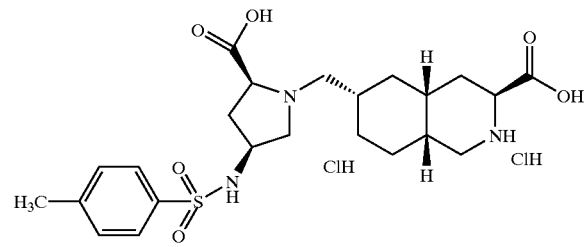

A. Preparation of N-t-butoxycarbonyl-4-methylbenzenesulfonamide:

To a solution of 5.0 g (29.2 mmol) of 4-methylbenzenesulfonamide, 3.2 g (32.1 mmol) of triethylamine, and 0.35 g (2.9 mmol) of 4-dimethylaminopyridine in 100 mL of dichloromethane was added 7.0 g (32.1 mmol) of di-tert-butyl dicarbonate. The reaction was stirred at ambient temperature for 18 hours and was then washed with a 50 mL of a 10% aqueous solution of sodium hydrogen sulfate and 50 mL of brine. The organic layer was removed and dried over magnesium sulfate, filtered, and concentrated under vacuo to afford 7.0 g (88%) of the title compound.

Negative ion electrospray mass spectrum: [M−H]⁻=270.

B. Preparation of Ethyl 2-methoxycarbonyl-6-[[2-ethoxycarbonyl-4-(N-4-methylbenzenesulfonamido)-1-pyrrolidinyl]methyl]decahydroisoquinoline-3-carboxylate:

To a 0° C. solution of 0.50 g (1.1 mmol) of material from Preparation 1, 0.35 g (1.2 mmol) material from Example 18, step A, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Elution through a 5 g Varian Bond Elut® SCX column with 2M ammonia in methyl alcohol followed by chromatography on 50 g silica gel (40% ethyl acetate/hexane) afforded 0.47 g (61%) of the title compound.

Positive ion electrospray mass spectrum: [M+H]⁺=694.

C. A solution of 0.4 g (0.60 mmol) of material from Example 18, step B in 20 mL of 5N hydrochloric acid was heated at 100° C. for 18 hours. The solution was concentrated in vacuo. The resulting solid was suspended in 10 mL of 1:1 acetone/diethyl ether and heated at 40° C. for 1 hour. The solid was filtered and washed with diethyl ether to afford 0.183 g (50%) of the title compound.

Analysis calculated for $C_{23}H_{35}Cl_2N_3O_6S$: % C, 50.00; % H, 6.39; % N, 7.61. Found: % C, 49.91; % H, 6.22; % N, 7.28.

Positive ion electrospray mass spectrum: [M]⁺=480.

EXAMPLE 19

Preparation of (3S,4aR,6S,8aR)-6-[[(2S,4S)-2-carboxy-4-(N-2-methylbenzenesulfonamido)-1-pyrrolidinyl]methyl]decahydroisoquinoline-3-carboxylic acid dihydrochloride

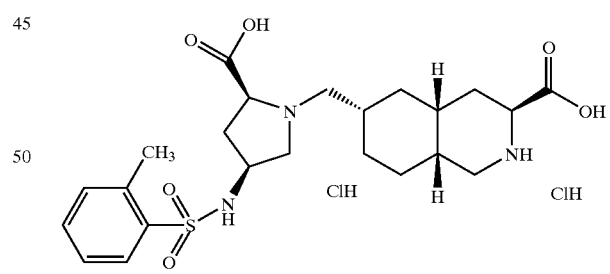

A. Preparation of N-t-butoxycarbonyl-2-methylbenzenesulfonamide:

To a solution of 5.0 g (29.2 mmol) of 2-methylbenzenesulfonamide, 3.2 g (32.1 mmol) of triethylamine, and 0.35 g (2.9 mmol) of 4-dimethylaminopyridine in 100 mL of dichloromethane was added 7.0 g (32.1 mmol) of di-tert-butyl dicarbonate. The reaction was stirred at ambient temperature for 18 hours and was then washed with a 50 mL of a 10% aqueous solution of sodium hydrogen sulfate and 50 mL of brine. The organic layer was removed and dried over magnesium sulfate, filtered, and concentrated under vacuo to afford 7.0 g (88%) of the title compound.

Negative ion electrospray mass spectrum: [M−H]⁻=270.

B. Preparation of Ethyl 2-methoxycarbonyl-6-[[2-ethoxycarbonyl-4-(N-2-methylbenzenesulfonamido)-1-pyrrolidinyl]methyl]decahydroisoquinoline-3-carboxylate:

To a 0° C. solution of 0.50 g (1.1 mmol) of material from Preparation 1, 0.35 g (1.2 mmol) material from Example 19, step A, and 0.33 g (1.2 mmol) of triphenylphosphine in 5 mL of dry tetrahydrofuran was added 0.22 g (1.2 mmol) of diethylazodicarboxylate dropwise. The mixture was stirred at room temperature for 18 hours, and then concentrated in vacuo. Elution through a 5 g Varian Bond Elut® SCX column with 2M ammonia in methyl alcohol followed by chromatography on 50 g silica gel (40% ethyl acetate/hexane) afforded 0.3 g (39%) of the title compound.

Positive ion electrospray mass spectrum: [M+H]⁺=694.

C. A solution of 0.3 g (0.4 mmol) of material from Example 19, step B in 20 mL of 5N hydrochloric acid was heated at 100° C. for 18 hours. The solution was concentrated in vacuo. The resulting solid was suspended in 10 mL of 1:1 acetone/diethyl ether and heated at 40° C. for 1 hour. The solid was filtered and washed with diethyl ether to afford 0.2 g (100%) of the title compound.

Analysis calculated for $C_{23}H_{35}Cl_2N_3O_6S$: % C, 50.00; % H, 6.39; % N, 7.61. Found: 15% C, 50.94; % H, 6.59; % N, 7.68.

Positive ion electrospray mass spectrum: [M]⁺=480.

EXAMPLE 20

Preparation of Ethyl (3S,4aR,6S,8aR)-6-[[(2S,4S)-2-ethoxycarbonyl-4-(N-benzylsulfonamido)-1-pyrrolidinyl]methyl]decahydroisoquinoline-3-carboxylate dihydrochloride

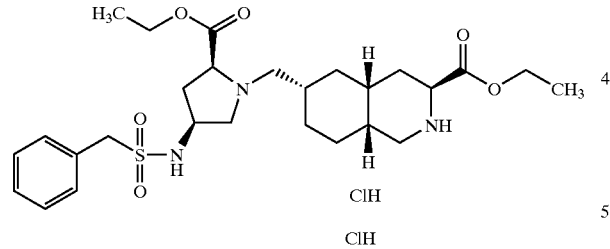

A solution of 3.1 g (6.5 mmol) of material from Example 7, step C in 20 mL of ethyl alcohol that has been saturated with gaseous hydrochloric acid was heated at 85° C. for 6 hours. The solution was concentrated in vacuo. The residue was eluted through a 10 g Varian Bond Elut® SCX column with 2M ammonia in ethyl alcohol followed by trituration with 2N hydrochloric acid in diethyl ether to afford 2.6 g (67%) of the title compound.

Analysis calculated for $C_{27}H_{41}N_3O_6S*1.5HCl$: % C, 54.93; % H, 7.26; % N, 7.12. Found: % C, 54.68; % H, 7.04; % N, 7.67.

Positive ion electrospray mass spectrum: [M+H]⁺=536.

EXAMPLE 21

Preparation of Ethyl (3S,4aR,6S,8aR)-6-[[(2S,4S)-2-ethoxycarbonyl-4-(5-methyltetrazol-2-yl)-1-pyrrolidinyl]methyl]-decahydroisoquinoline-3-carboxylate dihydrochloride

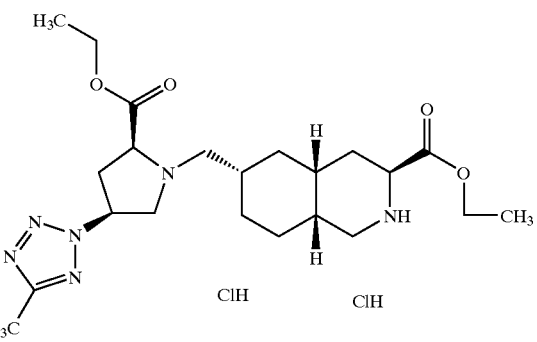

A solution of 0.4 g (0.8 mmol) of material from Example 2, step B in 25 mL of ethyl alcohol that has been saturated with gaseous hydrochloric acid was heated at 85° C. for 18 hours. The solution was concentrated in vacuo. The residue was suspended in a small volume of water and lyophylized to afford 0.31 g (75%) of the title compound.

Analysis calculated for $C_{22}H_{36}N_6O_4*2.5H_2O*2.0HCl$: % C, 46.64; % H, 7.65; % N, 14.85. Found: % C, 46.54; % H, 6.83; % N, 14.55.

Positive ion electrospray mass spectrum: [M+H]⁺=449.

EXAMPLE 22

Preparation of Ethyl (3S,4aR,6S,8aR)-6-[[(2S,4S)-2-ethoxycarbonyl-4-(5-adamantyltetrazol-2-yl)-1-pyrrolidinyl]methyl]-decahydroisoquinolne-3-carboxylate dihydrochloride

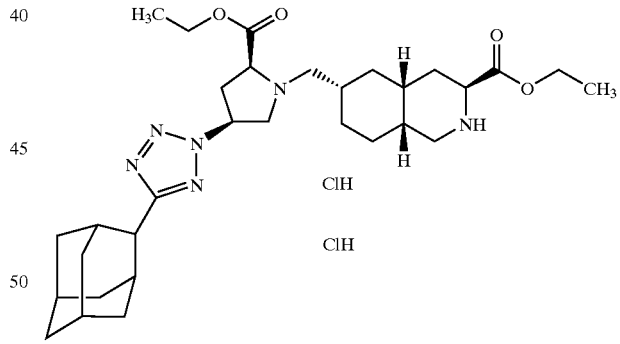

To a solution of 1.6 g (2.6 mmol) of material from Example 34, step B below, in 260 mL of dichloromethane was added 2.6 g (12.8 mmol) of iodotrimethylsilane dropwise. The mixture is stirred at room temperature for 18 hours. The solution was concentrated in vacuo and the resulting residue was purified by silica gel chromatography (gradient elution: 10% ethyl acetate/hexane to ethyl acetate). The colorless solid was triturated with 2N hydrochloric acid in diethyl ether to afford 2.4 g (45%) of the title compound.

Analysis calculated for $C_{31}H_{48}N_6O_4*2.0HCl$: % C, 58.03; % H, 7.85; % N, 13.10. Found: % C, 58.74; % H, 7.83; % N, 13.12.

Positive ion electrospray mass spectrum: [M+H]⁺=569.

EXAMPLE 23

Preparation of Ethyl (3S,4aR,6S,8aR)-6-[[(2S,4S)-2-ethoxycarbonyl-4-(5-cyclopentyltetrazol-2-yl)-1-pyrrolidinyl]methyl]-decahydroisoquinolne-3-carboxylate dihydrochloride

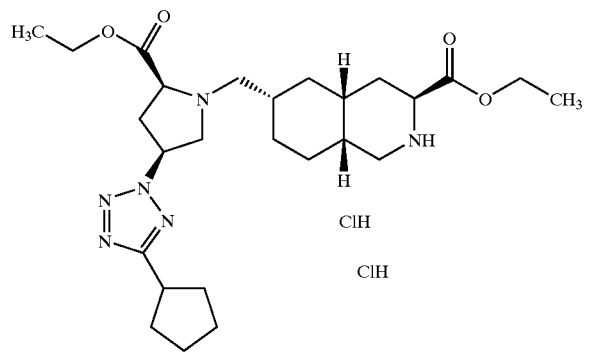

To a solution of 0.9 g (1.7 mmol) of material from Example 29, step B below, in 100 mL of dichloromethane was added 1.7 g (8.5 mmol) of iodotrimethylsilane dropwise. The mixture was stirred at room temperature for 18 hours. The solution was concentrated in vacuo and the resulting residue was purified by silica gel chromatography (ethyl acetate). The material was triturated with 2N hydrochloric acid in diethyl ether to afford 0.36 g (35%) of the title compound.

Analysis calculated for $C_{26}H_{42}N_6O_4 \cdot 2.0HCl$: % C, 54.26; % H, 7.71; % N, 14.60. Found: % C, 55.06; % H, 7.67; % N, 14.25.

Positive ion electrospray mass spectrum: $[M+H]^+=503$.

EXAMPLE 24

Preparation of Ethyl (3S,4aR,6S,8aR)-6-[[(2S,4S)-2-ethoxycarbonyl-4-(5-propyltetrazol-2-yl)-1-pyrrolidinyl]methyl]-decahydroisoquinoline-3-carboxylate dihydrochloride

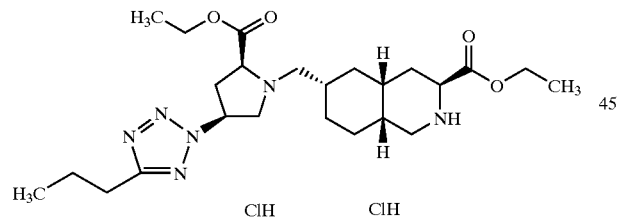

To a solution of 3.6 g (6.8 mmol) of material from Example 28, step A below, in 275 mL of dichloromethane was added 6.8 g (34.3 mmol) of iodotrimethylsilane dropwise. The mixture is stirred at room temperature for 18 hours. The solution was concentrated in vacuo and eluted through a Varian Bond Elut® SCX column with 2M ammonia in ethyl alcohol followed by chromatography on silica gel (gradient elution: ethyl acetate to 10% ethyl alcohol/ethyl acetate) to afford 1.5 g (47%) of the title compound. The material was triturated with 2N hydrochloric acid in diethyl ether to afford 1.36 g (43%) of the hydrochloric acid salt.

Analysis calculated for $C_{24}H_{40}N_6O_4 \cdot 1.75HCl$: % C, 53.34; % H, 7.78; % N, 15.55. Found: % C, 53.67; % H, 7.39; % N, 15.34.

Positive ion electrospray mass spectrum: $[M+H]^+=477$.

EXAMPLE 25

Preparation of Ethyl (3S,4aR,6S,8aR)-6-[[(2S,4S)-2-ethoxycarbonyl-4-(5-phenyltetrazol-2-yl)-1-pyrrolidinyl]methyl]-decahydroisoquinoline-3-carboxylate dihydrochloride

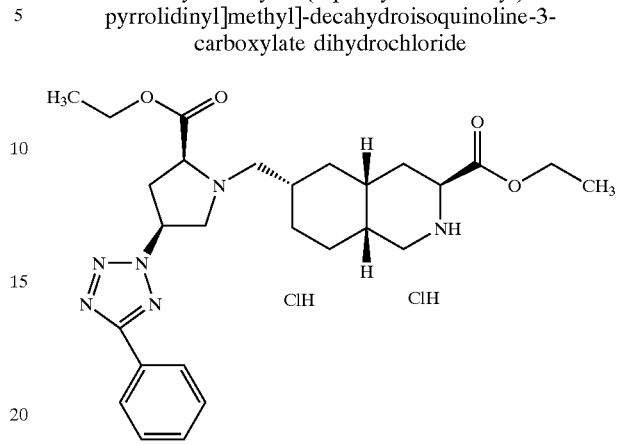

To a solution of 4.8 g (8.5 mmol) of material from Example 3, Step A in 300 mL of dichloromethane was added 8.5 g (42.9 mmol) of iodotrimethylsilane dropwise. The mixture was stirred at room temperature for 18 hours. The solution was concentrated in vacuo and the resulting residue was purified by silica gel chromatography (gradient elution: ethyl acetate to 50% ethyl alcohol/ethyl acetate) to afford 2.05 g (47%) of the title compound. The material was triturated with 2N hydrochloric acid in diethyl ether to afford 2.15 g (43%) of the hydrochloric acid salt.

Analysis calculated for $C_{27}H_{38}N_6O_4 \cdot 1.5H_2O \cdot 2.0HCl$: % C, 53.11; % H, 7.10; % N, 13.76. Found: % C, 52.97; % H, 6.86; % N, 12.95.

Positive ion electrospray mass spectrum: $[M+H]^+=511$.

EXAMPLE 26

Preparation of Ethyl (3S,4aR,6S,8aR)-6-[[(2S,4S)-2-ethoxycarbonyl-4-(N-methyl-N-benzylsulfonamido)-1-pyrrolidinyl]methyl]decahydroisoquinoline-3-carboxylate dihydrochloride

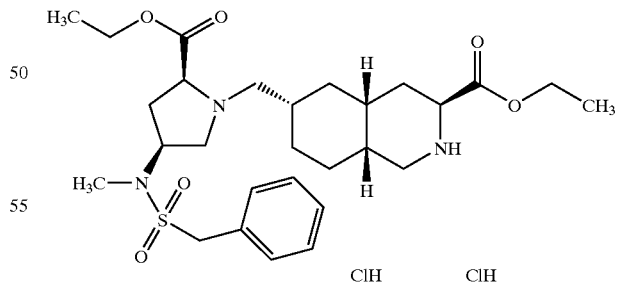

To a solution of 5.0 g (8.24 mmol) of material from Example 9, step A in 300 mL of dichloromethane was added 8.25 g (41.2 mmol) of iodotrimethylsilane dropwise. The mixture was stirred at room temperature for 18 hours. The solution was concentrated in vacuo and the resulting residue was purified by silica gel chromatography (gradient elution: ethyl acetate to 10% ethyl alcohol/ethyl acetate) to afford 3.03 g (66%) of the title compound. The material was triturated with 2N hydrochloric acid in diethyl ether to afford 3.3 g (65%) of the hydrochloric acid salt.

Analysis calculated for $C_{28}H_{43}N_3O_6S*1.0H_2O*2.0HCl$: % C, 52.49; % H, 7.39; % N, 6.56. Found: % C, 52.10; % H, 6.96; % N, 6.24.

Positive ion electrospray mass spectrum: $[M+H]^+=550$.

EXAMPLE 27

Preparation of (3S,4aR,6S,8aR)-6-[[(2S,4S)-2-carboxy-4-(5-(2,2-dimethylethyl)tetrazol-2-yl)-1-pyrrolidinyl]methyl]-decahydroisoquinoline-3-carboxylic acid

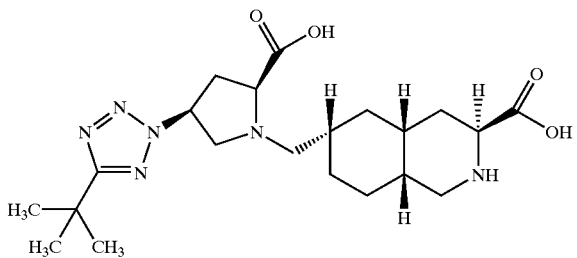

A. Preparation of Ethyl 2-methoxycarbonyl-6-[[2-ethoxycarbonyl-4-(5-(2,2-dimethylethyl)tetrazol-2-yl)-1-pyrrolidinyl]methyl]decahydroisoquinoline-3-carboxylate:

A solution of 521 mg (1.18 mmol) of material from Preparation 1, step B, 180 mg (1.4 mmol) of 5-(1,1-dimethyl)-ethyltetrazole and 366 mg (1.4 mmol) triphenylphosphine in 5 mL tetrahydrofuran was cooled to 0° C. DEAD (220 µL, 1.4 mmol) was added dropwise, and the reaction allowed to warm to room temperature and stirred for 17 hours. The solvents were then removed under vacuum. Chromatography (SCX, 2M ammonia in methanol, then $SiO_2$, 30% ethyl acetate/hexanes) afforded 160 mg (53.6%) of the title compound.

B. A mixture of 160 mg (0.27 mmol) of material from Example 27, step A and 20 mL of 6.0N HCl was heated to reflux. After 17 hours, the reaction mixture was allowed to cool to room temperature. The resulting mixture was concentrated in vacuo. Chromatography (SCX, 2N ammonia/methanol) afforded 80 mg (68.2%) of the title compound.

Analysis calculated for $C_{12}H_{34}N_6O_4.2H_2O$: C, 53.6; H, 8.1; N, 17.9. Found: C 53.85, H 7.81, N, 19.0.

Ion Spray MS: (MW=434): [M+H]=435.

EXAMPLE 28

Preparation of (3S,4aR,6S,8aR)-6-[[(2S,4S)-2-carboxy-4-(5-propyltetrazol-2-yl)-1-pyrrolidinyl]methyl]-decahydroisoquinoline-3-carboxylic acid

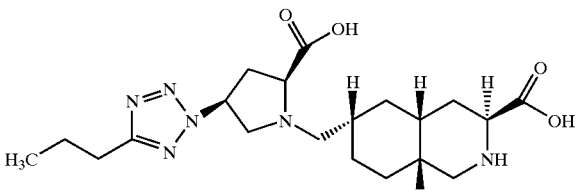

A. Preparation of Ethyl 2-methoxycarbonyl-6-[[2-ethoxycarbonyl-4-(5propyltetrazol-2-yl)-1-pyrrolidinyl]methyl]decahydroisoquinoline-3-carboxylate:

Following the procedure from Example 27, step A, and using 507 mg (1.1 mmol) of material from Preparation 1, step B, 155 mg (1.4 mmol) of 5-propyltetrazole and 361 mg (1.4 mmol) of triphenylphosphine, and DEAD (220 µL, 1.4 mmol), 210 mg (34.2%) of the title compound was prepared.

B. Following the procedure in Example 27, step B, and using 210 mg (0.40 mmol) of the compound from Example 31, step A, 140 mg (28.9%) of the title compound was prepared.

Analysis calculated for $C_{20}H_{32}N_6O_4.1.4H_2O$: C, 53.89; H, 7.81; N, 18.8. Found: C, 54.185, H, 7.02, N, 18.8.

Ion Spray MS: (MW=420): [M+H]=421.

EXAMPLE 29

Preparation of (3S,4aR,6S,8aR)-6-[[(2S,4S)-2-carboxy-4-(5-cyclopentyltetrazol-2-yl)-1-pyrrolidinyl]methyl]-decahydroisoquinoline-3-carboxylic acid dihydrochloride

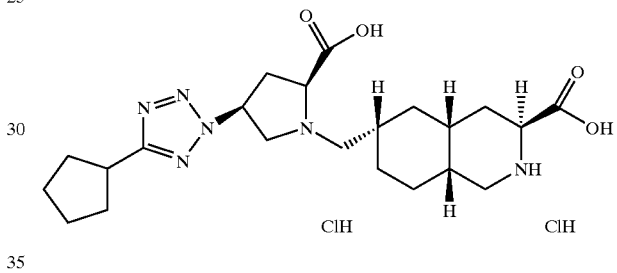

A. Preparation of 5-cyclopentyltetrazole: A mixture of 5.0 g (0.052 mol) of cyclopentylnitrile and 15 g (0.045 mol) of azidotributyltin was heated to 90° C., and stirred for 17 hours. The mixture was allowed to cool to room temperature, and 30 mL of 1.0N HCl was added. The mixture was extracted 3×25 mL diethyl ether, and the ether layers combined and extracted 3×25 mL 1.0N NaOH. The base layers were combined and washed 1×25 mL dichloromethane. The basic layer was acidified to pH=2 using 5N HCl. The resulting acidic layer was extracted 3×(3:1) dichloromethane/isopropanol. The organic layers were dried over $Na_2SO_4$, and the solvents removed under vacuum to afford 3.1 g (43.1%) of the title compound.

B. Preparation of Ethyl 2-methoxycarbonyl-6-[[2-ethoxycarbonyl-4-(5cyclopentyltetrazol-2-yl)-1-pyrrolidinyl]methyl]decahydroisoquinoline-3-carboxylate:

Following the procedure from Example 27, step A, and using 504 mg (1.1 mmol) of material from Preparation 1, step B, 189 mg (1.4 mmol) of material from Example 29, step A, 361 mg (1.4 mmol) of triphenylphosphine, and DEAD (220 µL, 1.4 mmol), 140 mg (21.9%) of the title compound was prepared.

C. Following the procedure in Example 27, step B, and using 140 mg (0.25 mmol) of the compound from Example 29, step B, 130 mg (29.1%) of the title compound was prepared.

Analysis calculated for $C_{22}H_{34}N_6O_4.3.2H_2O.2HCl$: C, 45.78; H, 7.40; N, 14.5. Found: C, 45.41; H, 6.56; N, 14.75.

Ion Spray MS: (MW=446): [M+H]=447.

EXAMPLE 30

Preparation of (3S,4aR,6S,8aR)-6-[[(2S,4S)-2-carboxy-4-(5-(2-methylpropyl)tetrazol-2-yl)-1-pyrrolidinyl]methyl]-decahydroisoquinoline-3-carboxylic acid hydrochloride

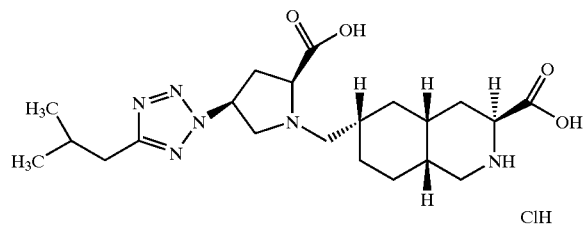

A. Preparation of Ethyl 2-methoxycarbonyl-6-[[2-ethoxycarbonyl-4-(5-(2-methylpropyl)ltetrazol-2-yl)-1-pyrrolidinyl]methyl]decahydroisoquinoline-3-carboxylate:

Following the procedure from Example 27, step A, and using 518 mg (1.2 mmol) of material from Preparation 1, step B, 178 mg (1.4 mmol) of 5-(2-methylpropyl)/tetrazole and 361 mg (1.4 mmol) of triphenylphosphine, and DEAD (220 μL, 1.4 mmol), 140 mg (25.5%) of the title compound was prepared.

B. Following the procedure in Example 27, step B, and using 140 mg (0.25 mmol) of the compound from Example 30, step A, 55 mg (49.6%) of the title compound was prepared.

Analysis calculated for $C_{21}H_{34}N_6O_4 \cdot HCl$: C, 53.5; H, 7.49; N, 17.8. Found: C, 53.2, H, 7.1, N, 15.2.

Ion Spray MS: (MW=434): [M+H]=435.

EXAMPLE 31

Preparation of (3S,4aR,6S,8aR)-6-[[(2S,4S)-2-carboxy-4-(5-cyclopropyltetrazol-2-yl)-1-pyrrolidinyl]methyl]-decahydroisoquinoline-3-carboxylic acid

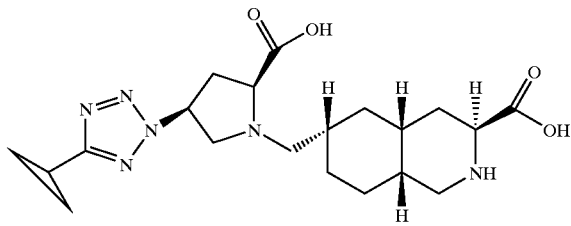

A. Preparation of Ethyl 2-methoxycarbonyl-6-[[2-ethoxycarbonyl-4-(5-cyclopropyltetrazol-2-yl)-1-pyrrolidinyl]methyl]decahydroisoquinoline-3-carboxylate:

Following the procedure from Example 27, step A, and using 504 mg (1.1 mmol) of material from Preparation 1, step B, 170 mg (1.4 mmol) of 5-cyclopropyltetrazole and 361 mg (1.4 mmol) of triphenylphosphine, and DEAD (220 μL, 1.4 mmol), 140 mg (23.9%) of the title compound was prepared.

B. Following the procedure in Example 27, step B, and using 140 mg (0.25 mmol) of the compound from Example 31, step A, 130 mg (84.6%) of the title compound was prepared.

$^1$H NMR (400 MHz, D$_2$O) δ 5.60 (1H s), δ 4.30 (2H s), δ 3.95–3.91 (1H m), δ3.90–3.85 (1H m), δ 3.22–3.00 (5H m), δ 2.75–2.7 (1H m), δ 2.10–1.80 (7H m) δ 1.75 (3H s) δ 1.60–0.80 (6H m).

Ion Spray MS: (MW=417): [M+H]=418.

EXAMPLE 32

Preparation of (3S,4aR,6S,8aR)-6-[[(2S,4S)-2-carboxy-4-(5-ethyltetrazol-2-yl)-1-pyrrolidinyl]methyl]-decahydroisoquinoline-3-carboxylic acid

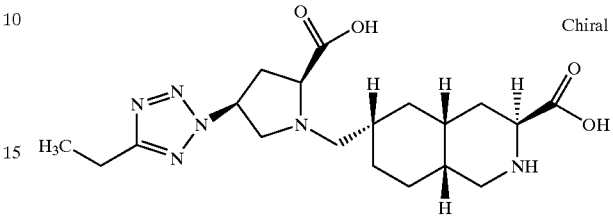

A. Preparation of Ethyl 2-methoxycarbonyl-6-[[2-ethoxycarbonyl-4-(5-ethyltetrazol-2-yl)-1-pyrrolidinyl]methyl]decahydroisoquinoline-3-carboxylate:

Following the procedure from Example 27, step A, and using 500 mg (1.1 mmol) of material from Preparation 1, step B, 160 mg (1.4 mmol) of 5-ethyltetrazole and 361 mg (1.4 mmol) of triphenylphosphine, and DEAD (220 μL, 1.4 mmol), 140 mg (23.8%) of the title compound was prepared.

B. Following the procedure in Example 27, step B, and using 140 mg (0.25 mmol) of the compound from Example 32, step A, 110 mg (92.2%) of the title compound was prepared.

$^1$H NMR (400 MHz, D$_2$O) δ 5.65 (1H s), δ 4.43–4.25 (2H m), δ 3.95–3.85 (2H m), δ 3.22–2.90 (4H m), δ 2.80–2.65 (4H m), δ 2.00–1.80 (4H m) δ 1.45 (4H s) δ 1.60–0.80 (6H m).

Ion Spray MS: (MW=406): [M+H]=407.

EXAMPLE 33

A. Preparation of (3S,4aR,6S,8aR)-6-[[(2S,4S)-2-carboxy-4-(5-(2-propyl)tetrazol-2-yl)-1-pyrrolidinyl]methyl]-decahydroisoquinoline-3-carboxylic acid dihydrochloride

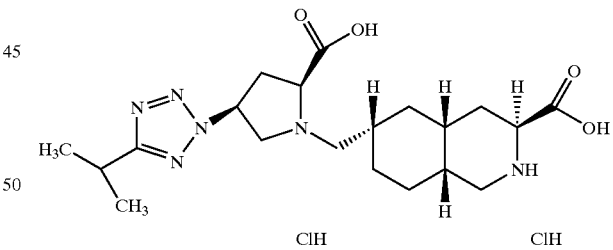

A. Preparation of Ethyl 2-methoxycarbonyl-6-[[2-ethoxycarbonyl-4-(5-(2-propyl)tetrazol-2-yl)-1-pyrrolidinyl]methyl]decahydroisoquinoline-3-carboxylate:

Following the procedure from Example 27, step A, and using 504 mg (1.1 mmol) of material from Preparation 1, step B, 170 mg (1.4 mmol) of 5-(2-propyl)-tetrazole and 361 mg (1.4 mmol) of triphenylphosphine, and DEAD (220 μL, 1.4 mmol), 38 mg (6.2%) of the title compound was prepared.

B. Following the procedure in Example 27, step B, and using 38 mg (0.07 mmol) of the compound from Example 33, step A, 30 mg (98.1%) of the title compound was prepared.

Analysis calculated for $C_{20}H_{32}N_6O_4 \cdot 2HCl \cdot 1.5H_2O$: C, 46.15; H, 7.17; N, 16.15. Found: C, 46.34; H, 6.92; N, 15.98.
Ion Spray MS: (MW=419): [M+H]=420.

EXAMPLE 34

Preparation of (3S,4aR,6S,8aR)-6-[[(2S,4S)-2-carboxy-4-(5-adamantyltetrazol-2-yl)-1-pyrrolidinyl]methyl]-decahydroisoquinoline-3-carboxylic acid dihydrochloride

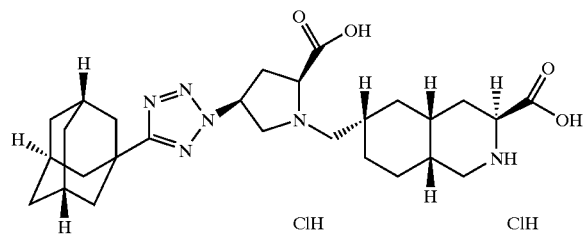

A. Preparation of 5-adamantyltetrazole:

Following the procedure of Example 29, step A, and using 3.0 g (0.52 mol) of adamantylnitrile, 0.35 g (9.2%) of the title compound was obtained.

B. Preparation of Ethyl 2-methoxycarbonyl-6-[[2-ethoxycarbonyl-4-(5-adamantyltetrazol-2-yl)-1-pyrrolidinyl]methyl]decahydroisoquinoline-3-carboxylate:

Following the procedure from Example 27, step A, and using 504 mg (1.1 mmol) of material from Preparation 1, step B, 170 mg (1.4 mmol) of material from Example 34, step A and 361 mg (1.4 mmol) of triphenylphosphine, and DEAD (220 μL, 1.4 mmol), 54 mg (7.3%) of the title compound was prepared.

C. Following the procedure in Example 27, step B, and using 52 mg (0.08 mmol) of the compound from Example 34, step B, 37.8 mg (80.1%) of the title compound was prepared.

Analysis calculated for $C_{27}H_{40}N_6O_4 \cdot 2HCl \cdot 3H_2O$: C, 50.7; H, 7.56; N, 13.1. Found 50.98, H, 7.08, N, 12.38.
Ion Spray MS: (=512): [M+H]=513.

EXAMPLE 35

Preparation of (3S,4aR,6S,8aR)-6-[[(2S,4S)-2-carboxy-4-(5-pentyltetrazol-2-yl)-1-pyrrodinyl]methyl]-decahydroisoquinoline-3-carboxylic acid

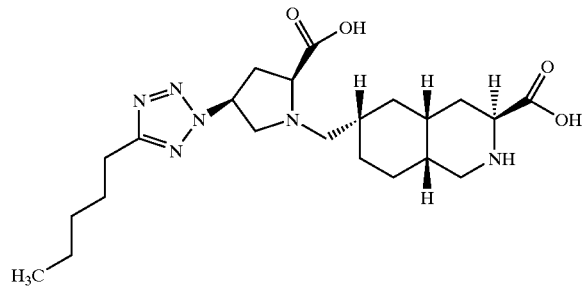

A. Preparation of Ethyl 2-methoxycarbonyl-6-[[2-ethoxycarbonyl-4-(5-pentyltetrazol-2-yl)-1-pyrrolidinyl]methyl]decahydroisoquinoline-3-carboxylate:

Following the procedure from Example 27, step A, and using 504 mg (1.1 mmol) of material from Preparation 1, step B, 222.7 mg (1.6 mmol) of 5-n-pentyltetrazole and 420 mg (1.6 mmol) of triphenylphosphine, and DEAD (220 μL, 1.4 mmol), 77 mg (12.1%) of the title compound was prepared.

B. Following the procedure in Example 27, step B, and using 75 mg (0.13 mmol) of the compound from Example 35, step A, 70 mg (87.6%) of the title compound was prepared.

$^1$H NMR (400 MW, $D_2O$) δ 5.65 (1H d, J=12.8 Hz), δ 4.43–4.25 (2H m), δ 3.95–3.85 (2H m), δ 3.22–3.00 (5H m), δ 2.80–2.63 (3H m), δ 2.00 (1H d, J=12.6 Hz), δ 1.95–1.80 (4H m) δ 1.45 (6H s) δ 1.60–1.10 (6H m), δ 0.80 (3H t, J=4.6 Hz).

Ion Spray MS: (MW=448): [M+H]=449.

EXAMPLE 36

Preparation of (3S,4aR,6S,8aR)-6-[[(2S,4S)-2-carboxy-4-(5-(1,1'-biphenyl)tetrazol-2-yl)-1-pyrrolidinyl]methyl]-decahydroisoquinoline-3-carboxylic acid

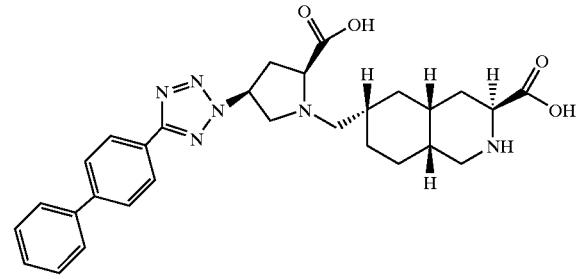

A. Preparation of Ethyl 2-methoxycarbonyl-6-[[2-ethoxycarbonyl-4-(5-(1,1'-biphenyl)tetrazol-2-yl)-1-pyrrolidinyl]methyl]decahydroisoquinoline-3-carboxylate:

Following the procedure from Example 27, step A, and using 504 mg (1.1 mmol) of material from Preparation 1, step B, 355 mg (1.6 mmol) of 5-[1,1'-biphenyl]4-yl-tetrazole and 420 mg (1.6 mmol) of triphenylphosphine, and DEAD (220 μL, 1.4 mmol), 244 mg (33.2%) of the title compound was prepared.

B. Following the procedure in Example 27, step B; and using 240 mg (0.38 mmol) of the compound from Example 36, step A, 150 mg (74.8%) of the title compound was prepared.

$^1$H NMR (400 MHz, $CD_3OD$) δ 8.18 (2H d, J=8.1 Hz), δ 7.68 (2H d, J=9.2 Hz), δ 7.62 (1H d, J=8.1 Hz), δ 7.23 (2H t, J=8.1 Hz), δ 7.18 (1H t, J=7.0 Hz), δ 5.93 (1H s), δ 4.43 (1H d, J=12.5 Hz), δ 4.10–3.95 (2H m), δ 3.22–3.00 (4H m), δ 2.15–1.50 (14H m), δ 1.15 (1H s).

Ion Spray MS: (MW=530): [M+H]=531.

EXAMPLE 37

Preparation of (3S,4aR,6S,8aR)-6-[[(2S,4S)-2-carboxy-4-(5-(4-methoxyphenyl)tetrazol-2-yl)-1-pyrrolidinyl]methyl]-decahydroisoquinoline-3-carboxylic acid

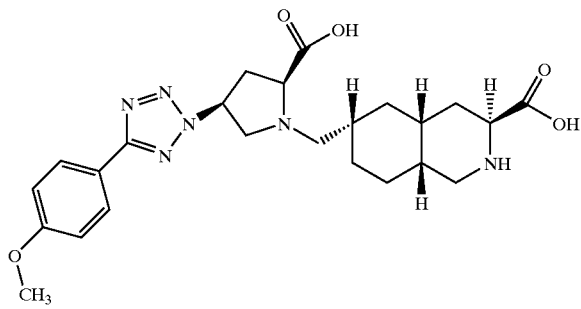

A. Preparation of Ethyl 2-methoxycarbonyl-6-[[2-ethoxycarbonyl-4-(5-(4methoxyphenyl)tetrazol-2-yl)-1-pyrrolidinyl]methyl]decahydroisoquinoline-3-carboxylate:

Following the procedure from Example 27, step A, and using 504 mg (1.1 mmol) of material from Preparation 1, step B, 212 mg (1.6 mmol) of 5-[4-methoxyphenyl]-tetrazole and 441 mg (1.6 mmol) of triphenylphosphine, and DEAD (220 mL, 1.4 mmol), 182 mg (25.2%) of the title compound was prepared.

B. Following the procedure in Example 27, step B, and using 180 mg (0.30 mmol) of the compound from Example 37, step A, 192 mg (87.0%) of the title compound was prepared.

$^1$H NMR (400 MHz, CD$_3$OD) δ 7.88 (2H d, J=8.0 Hz), δ 6.92 (2H d, J=7.9 Hz), δ 5.93 (1H s), δ 4.43 (1H d, J=11.6 Hz), δ 4.38–4.30 (1H m), δ 3.90–3.79 (2H m), δ 3.70 (3H s), δ 3.22–3.00 (5H m), δ 2.70–2.64 (2H m), δ 2.15–1.90 (5H m), δ 1.59 (4H m), δ 1.15 (1H s).

Ion Spray MS: (MW=484): [M+H]=485.

EXAMPLE 38

Preparation of (3S,4aR,6S,8aR)-6-[[(2S,4S)-2-carboxy-4-(5-(4-methylsulfonyl)tetrazol-2-yl)-1-pyrrolidinyl]methyl]-decahydroisoquinoline-3-carboxylic acid

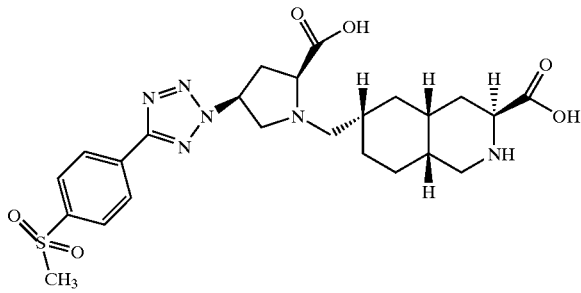

A. Preparation of 5-(4-methylsulfonylphenyl)-tetrazole:

Following the procedure of Example 29, step A, and using 3.0 g (0.52 mol) of 4-methylsulfonylphenyl nitrile, 2.4 g (64.6%) of the title compound was obtained.

B. Preparation of Ethyl 2-methoxycarbonyl-6-[[2-ethoxycarbonyl-4-(5-(4-methylsulfonylphenyl)tetrazol-2-yl)-1-pyrrolidinyl]methyl]decahydroisoquinoline-3-carboxylate:

Following the procedure from Example 27, step A, and using 504 mg (1.1 mmol) of material from Preparation 1, step B, 268 mg (1.6 mmol) of material from Example 38, step A and 443 mg (1.6 mmol) of triphenylphosphine, and DEAD (220 μL, 1.4 mmol), 333 mg (45.6%) of the title compound was prepared.

C. Following the procedure in Example 27, step B, and using 330 mg (0.51 mmol) of the compound from Example 38, step C, 324 mg (95.2%) of the title compound was prepared.

$^1$H NMR (400 MHz, CD$_3$OD) δ 8.09 (2H d, J=8.1 Hz), δ 7.84 (2H d, J=7.9 Hz), δ 5.89 (1H s), δ 4.45 (1H d, J=11.3 Hz), δ 4.37–4.303 (1H m), δ 3.90–3.83 (2H m), δ 3.52–3.0 (9H m), δ 2.74–2.69 (1H m), δ 2.15–1.79 (5H m), δ 1.58 (3H m) δ1.43–1.39 (1H m), δ 0.90 (1H s).

Ion Spray MS: (MW=548): [M+H]=549.

EXAMPLE 39

Preparation of (3S,4aR,6S,8aR)-6-[[(2S,4S)-2-carboxy-4-(5-(4-trifluoromethylphenyl)tetrazol-2-yl)-1-pyrrolidinyl]methyl]-decahydroisoquinoline-3-carboxylic acid

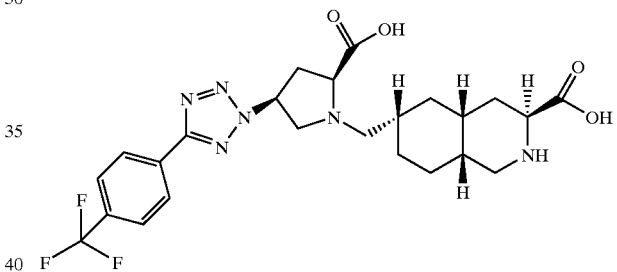

A. Preparation of Ethyl 2-methoxycarbonyl-6-[[2-ethoxycarbonyl-4-(5-(4-trifluoromethylphenyl)tetrazol-2-yl)-1-pyrrolidinyl]methyl]decahydroisoquinoline-3-carboxylate:

Following the procedure from Example 27, step A, and using 504 mg (1.1 mmol) of material from Preparation 1, step B, 340 mg (1.6 mmol) of 5-[4-trifluoromethylphenyl]-tetrazole and 419 mg (1.6 mmol) of triphenylphosphine, and DEAD (220 μL, 1.4 mmol), 266 mg (36%) of the title compound was prepared.

B. Following the procedure in Example 27, step B, and using 263 mg (0.42 mmol) of the compound from Example 39, step A, 180 mg (82.1%) of the title compound was prepared:

$^1$H NMR (400 MHz, D$_2$O) δ 8.09 (2H d, J=8.0 Hz), δ 7.70 (2H d, J=7.9 Hz), δ 5.95 (1H s), δ 4.60–4.44 (2H m), δ 4.41–3.87 (2H m), δ 3.40–3.09 (5H m), δ 2.85–2.78 (1H m), δ 2.17–1.83 (5H m), δ 1.72–1.27 (5H m), δ 1.05 (1H m).

Ion Spray MS: (MW=522): [M+H]=523.

EXAMPLE 40

Preparation of (3S,4aR,6S,8aR)-6-[[(2S,4S)-2-carboxy-4-(5-(4-fluorophenyl)tetrazol-2-yl)-1-pyrrolidinyl]methyl]-decahydroisoquinoline-3-carboxylic acid

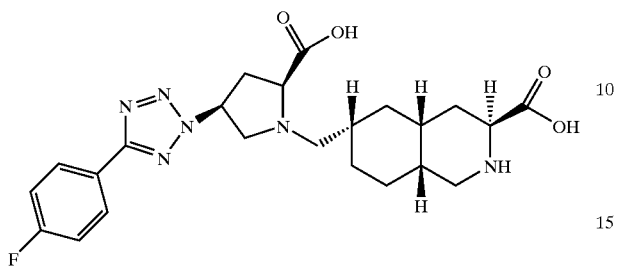

A. Preparation of Ethyl 2-methoxycarbonyl-6-[[2-ethoxycarbonyl-4-(5-(4-fluorophenyl)tetrazol-2-yl)-1-pyrrolidinyl]methyl]decahydroisoquinoline-3-carboxylate:

Following the procedure from Example 27, step A, and using 504 mg (1.1 mmol) of material from Preparation 1, step B, 261 mg (1.6 mmol) of 5-[4-fluorophenyl]-tetrazole and 419 mg (1.6 mmol) of triphenylphosphine, and DEAD (220 μL, 1.4 mmol), 301 mg (45%) of the title compound was prepared B. Following the procedure in Example 27, step B, and using 301 mg (0.51 mmol) of the compound from Example 40, step A, 261 mg (92.2%) of the title compound was prepared.

$^1$H NMR (400 MHz, D$_2$O) δ 7.99 (2H d, J=8.0 Hz), δ 7.09 (2H d, J=7.9 Hz), δ 5.91 (1H s), δ 4.51–4.20 (3H m), δ 3.90–3.80 (2H m), δ 3.40–3.01 (5H m), δ 2.80–2.71 (1H m), δ 2.10–1.81 (5H m), δ 1.68–1.55 (4H m), δ 0.90 (1H m).

Ion Spray MS: (MW=472): [M+H]=473.

EXAMPLE 41

Preparation of (3S,4aR,6S,8aR)-6-[[(2S,4S)-2-carboxy-4-(5-(4-phenoxyphenyl)tetrazol-2-yl)-1-pyrrolidinyl]methyl]-decahydroisoquinoline-3-carboxylic acid

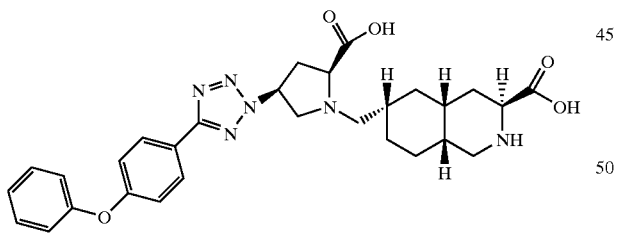

A. Preparation of Ethyl 2-methoxycarbonyl-6-[[2-ethoxycarbonyl-4-(5-(4-phenoxyphenyl)tetrazol-2-yl)-1-pyrrolidinyl]methyl]decahydroisoquinoline-3-carboxylate:

Following the procedure from Example 27, step A, and using 500 mg (1.1 mmol) of material from Preparation 1, step B, 380 mg (1.6 mmol) of 5-[4-phenoxyphenyl]-tetrazole and 419 mg (1.6 mmol) of triphenylphosphine, and DEAD (220 μL, 1.4 mmol), 311 mg (40%) of the title compound was prepared.

B. Following the procedure in Example 27, step B, and using 311 mg (0.47 mmol) of the compound from Example 41, step A, 251 mg (97.8%) of the title compound was prepared.

$^1$H NMR (400 MHz, D$_2$O) δ 7.5 (2H br s), δ 6.85 (2H br s), δ 6.7 (1H s), δ 6.5 (4H br s), δ 5.68 (1H s), δ 4.30 (2H br s), δ 3.82 (2H br s), δ 3.29–2.96 (5H m), δ 2.60 (1H br s), δ 2.00–1.22 (1H m),

Ion Spray MS: (MW=545): [M+H]=546.

EXAMPLE 42

Preparation of (3S,4aR,6S,8aR)-6-[[(2S,4S)-2-carboxy-4-(5-(4-propyloxyphenyl)tetrazol-2-yl)-1-pyrrolidinyl]methyl]-decahydroisoquinoline-3-carboxylic acid

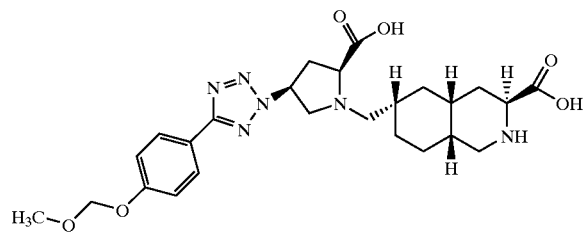

A. Preparation of Ethyl 2-methoxycarbonyl-6-[[2-ethoxycarbonyl-4-(5-(4-propyloxyphenyl)tetrazol-2-yl)-1-pyrrolidinyl]methyl]decahydroisoquinoline-3-carboxylate:

Following the procedure from Example 27, step A, and using 500 mg (1.1 mmol) of material from Preparation 1, step B, 326 mg (1.6 mmol) of 5-[4-propyloxyphenyl]-tetrazole and 419 mg (1.6 mmol) of triphenylphosphine, and DEAD (220 μL, 1.4 mmol), 280 mg (40.6%) of the title compound was prepared.

B. Following the procedure in Example 27, step B, and using 275 mg (0.45 mmol) of the compound from Example 42, step A, 211 mg (92.1%) of the title compound was prepared.

$^1$H NMR (400 MHz, D$_2$O) δ 7.78 (2H d, J=10.4 Hz), δ 6.93 (2H d, J=10.3 Hz), δ 5.79 (1H s), δ 4.50–4.24 (2H m), δ 3.90–3.81 (4H m), δ 3.30–3.09 (5H m), δ 2.73–2.63 (1H m), δ 2.05–1.78 (5H m), δ 1.65–1.50 (7H m), δ 1.05–0.78 (4H m).

Ion Spray MS: (W=512): [M+H]=513.

EXAMPLE 43

Preparation of (3S,4aR,6S,8aR)-6-[[(2S,4S)-2-carboxy-4-(5-(4-chlorophenyl)tetrazol-2-yl)-1-pyrrolidinyl]methyl]-decahydroisoquinoline-3-carboxylic acid

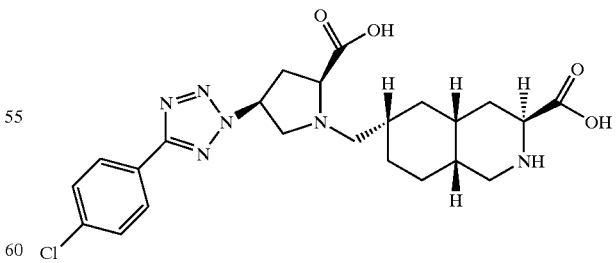

A. Preparation of Ethyl 2-methoxycarbonyl-6-[[2-ethoxycarbonyl-4-(5-(4-chlorophenyl)tetrazol-2-yl)-1-pyrrolidinyl]methyl]decahydroisoquinoline-3-carboxylate:

Following the procedure from Example 27, step A, and using 500 mg (1.1 mmol) of material from Preparation 1, step B, 288 mg (1.6 mmol) of 5-[4-chlorophenyl]-tetrazole and 419 mg (1.6 mmol) of triphenylphosphine, and DEAD (220 μL, 1.4 mmol), 285 mg (42.9%) of the title compound was prepared.

B. Following the procedure in Example 27, step B, and using 280 mg (0.46 mmol) of the compound from Example 43, step A, 156 mg (69.4%) of the title compound was prepared.

$^1$H NMR (400 M&z, D$_2$O) δ 7.86 (2H d, J=8.2 Hz), δ 7.42 (2H d, J=8.1 Hz), δ 5.82 (1H s), δ 4.45 (1H m), δ 4.35 (1H m), δ 3.92–3.80 (2H m), δ 3.30–3.00 (4H m), δ 2.10–1.23 (12H m), δ 0.75 (1H m).

Ion Spray MS: (MW=488): [M+H]=489.

EXAMPLE 44

Preparation of (3S,4aR,6S,8aR)-6-[[(2S,4S)-2-carboxy-4-(5-(2-chlorophenyl)tetrazol-2-yl)-1-pyrrolidinyl]methyl]-decahydroisoquinoline-3-carboxylic acid

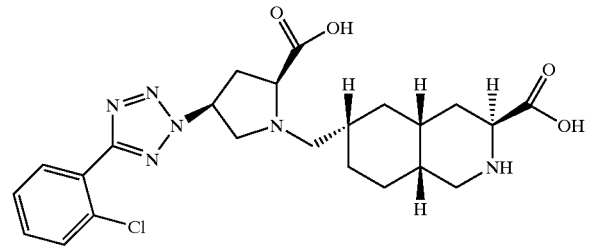

A. Preparation of Ethyl 2-methoxycarbonyl-6-[[2-ethoxycarbonyl-4-(5-(2-chlorophenyl)tetrazol-2-yl)-1-pyrrolidinyl]methyl]decahydroisoquinoline-3-carboxylate:

Following the procedure from Example 27, step A, and using 500 mg (1.1 mmol) of material from Preparation 1, step B, 288 mg (1.6 mmol) of 5-[2-chlorophenyl]-tetrazole and 419 mg (1.6 mmol) of triphenylphosphine, and DEAD (220 μL, 1.4 mmol), 250 mg (37.6%) of the title compound was prepared.

B. Following the procedure in Example 27, step B, and using 250 mg (0.41 mmol) of the compound from Example 44, step A, 120 mg (59.8%) of the title compound was prepared.

$^1$H NMR (400 MHz, D$_2$O) δ 7.72 (1H d, J=8.0 Hz), δ 7.50 (1H d, J=7.9 Hz), δ 7.42–7.30 (2H m), δ 5.90 (1H s), δ 4.50–4.44 (1H m), δ 4.41–4.30 (1H m), δ 3.95–3.90 (2H m), δ 3.30–2.98 (5H m), δ 2.81–2.73 (1H m), δ 2.08–1.25 (10H m), δ 0.98 (1H m).

Ion Spray MS: (W=488): [M+H]=489.

EXAMPLE 45

Preparation of (3S,4aR,6S,8aR)-6-[[(2S,4S)-2-carboxy-4-(5-(3-methoxyphenyl)tetrazol-2-yl)-1-pyrrolidinyl]methyl]-decahydroisoquinoline-3-carboxylic acid

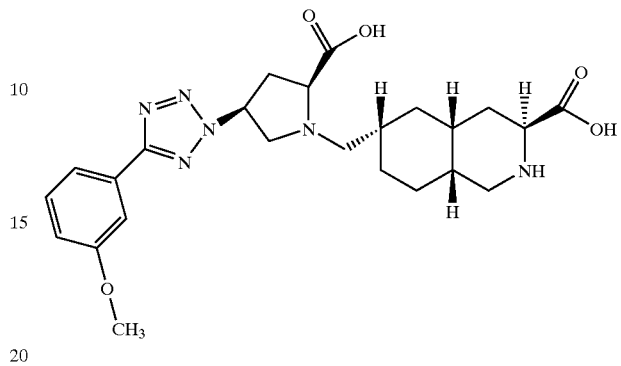

A. Preparation of Ethyl 2-methoxycarbonyl-6-[[2-ethoxycarbonyl-4-(5-(3-methoxyphenyl)tetrazol-2-yl)-1-pyrrolidinyl]methyl]decahydroisoquinoline-3-carboxylate:

Following the procedure from Example 27, step A, and using 500 mg (1.1 mmol) of material from Preparation 1, step B, 281 mg (1.6 mmol) of 5-[3-methoxyphenyl]-tetrazole and 419 mg (1.6 mmol) of triphenylphosphine, and DEAD (220 μL, 1.4 mmol), 211 mg (32.1%) of the title compound was prepared.

B. Following the procedure in Example 27, step B, and using 205 mg (0.34 mmol) of the compound from Example 45, step A, 161 mg (97.8%) of the title compound was prepared.

$^1$H NMR (400 MHz, D$_2$O) δ 7.55–7.24 (3H m), δ 6.95 (1H d, J=7.8 Hz), δ 5.90 (1H s), δ 4.45–4.34 (2H m), δ 3.90–3.80 (21 m), δ 3.69 (3H s), δ 3.30–2.98 (4H m), δ 2.78–2.63 (1H m), δ 2.08–1.62 (5H m), δ 1.60–1.22 (5H m) δ 1.00–0.90 (1H m).

Ion Spray MS: (MW=484): [M+H]=485.

EXAMPLE 46

Preparation of (3S,4aR,6S,8aR)-6-[[(2S,4S)-2-carboxy-4-(5-(2-methoxyphenyl)tetrazol-2-yl)-1-pyrrolidinyl]methyl]-decahydroisoquinoline-3-carboxylic acid

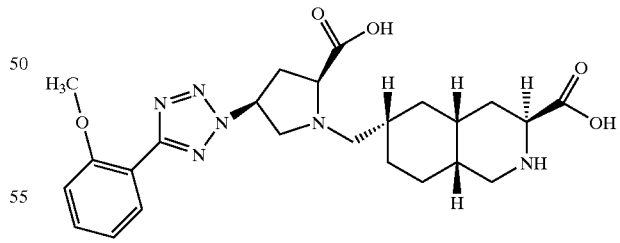

A. Preparation of Ethyl 2-methoxycarbonyl-6-[[2-ethoxycarbonyl-4-(5-(2-methoxyphenyl)tetrazol-2-yl)-1-pyrrolidinyl]methyl]decahydroisoquinoline-3-carboxylate:

Following the procedure from Example 27, step A, and using 500 mg (1.1 mmol) material from Preparation 1, step B, 281 mg (1.6 mmol) of 5-[2-methoxyphenyl]-tetrazole and 419 mg (1.6 mmol) of triphenylphosphine, and DEAD (220 μL, 1.4 mmol), 210 mg (31.0%) of the title compound was prepared.

B. Following the procedure in Example 27, step B, and using 210 mg (0.35 mmol) of the compound from Example 46, step A, 174 mg (97.4%) of the title compound was prepared.

$^1$H NMR (400 MHz, D$_2$O) δ 7.75 (1H d, J=8.1 Hz), δ 7.43 (1H d, J=8.1 Hz), δ 7.18–7.00 (2H m), δ 5.84 (1H s), δ 4.53 4.34 (4H m), δ 3.90–3.40 (4H m), δ 3.39–3.01 (5H m), δ 2.96–2.78 (1H m), δ 2.10–1.60 (4H m), δ 1.59–0.90 (6H m).

Ion Spray MS: (MW=484): [M+H]=485.

EXAMPLE 47

Preparation of (3S,4aR,6S,8aR)-6-[[(2S,4S)-2-carboxy-4-(5-(4-chlorobenzyl)tetrazol-2-yl)-1-pyrrolidinyl]methyl]-decahydroisoquinoline-3-carboxylic acid

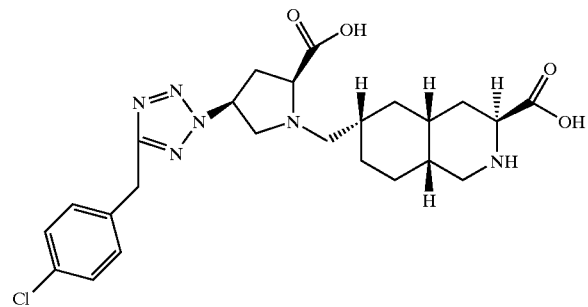

A. Preparation of Ethyl 2-methoxycarbonyl-6-[[2-ethoxycarbonyl-4-(5-(4-chlorobenzyl)tetrazol-2-yl)-1-pyrrolidinyl]methyl]decahydroisoquinoline-3-carboxylate:

Following the procedure from Example 27, step A, and using 500 mg (1.1 mmol) of material from Preparation 1, step B, 310 mg (1.6 mmol) of 5-[4-chlorobenzyl]-tetrazole and 419 mg (1.6 mmol) of triphenylphosphine, and DEAD (220 μL, 1.4 mmol), 201 mg (20.3%) of the title compound was prepared.

B. Following the procedure in Example 27, step B, and using 201 mg (0.32 mmol) of the compound from Example 47, step A, 150 mg (93.1%) of the title compound was prepared.

$^1$H NMR (400 MHz, D$_2$O) δ 7.30 (2H d, J=8.1 Hz), δ 7.18 (2H d, J=8.1 Hz), δ 5.71 (1H s), δ 4.53–4.00 (4H m), δ 3.90–3.80 (2H m), δ 3.30–3.01 (5H m), δ 2.80–2.68 (1H m), δ 2.10–1.68 (6H m), δ 1.59–0.90 (6H m).

Ion Spray MS: (MW=502): [M+H]=503.

EXAMPLE 48

Preparation of (3S,4aR,6S,8aR)-6-[[(2S,4S)-2-carboxy-4-(5-benzyltetrazol-2-yl)-1-pyrrolidinyl]methyl]-decahydroisoquinoline-3-carboxylic acid

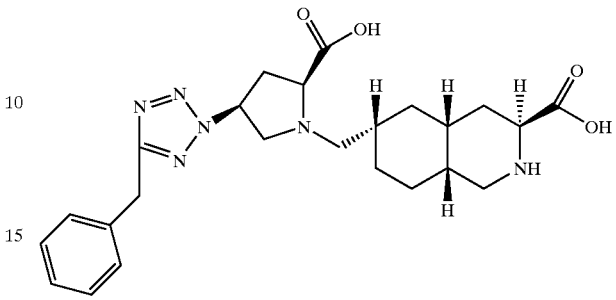

A. Preparation of Ethyl 2-methoxycarbonyl-6-[[2-ethoxycarbonyl-4-(5-benzyltetrazol-2-yl)-1-pyrrolidinyl]methyl]decahydroisoquinoline-3-carboxylate:

Following the procedure from Example 27, step A, and using 500 mg (1.1 mmol) of material from Preparation 1, step B, 260 mg (1.6 mmol) of 5-[benzyl]-tetrazole and 419 mg (1.6 mmol) of triphenylphosphine, and DEAD (220 μL, 1.4 mmol), 205 mg (22.0%) of the title compound was prepared.

B. Following the procedure in Example 27, step B, and using 205 mg (0.35 mmol) of the compound from Example 48, step A, 145 mg (88.5%) of the title compound was prepared.

$^1$H NMR (400 MHz, D$_2$O) δ 7.40–7.20 (5H m), δ 5.81 (1H s), δ 4.63–4.40 (2H m), δ 4.21 (2H s), δ 4.01–3.81 (2H m), δ 3.27–3.00 (5H m), δ 2.90–2.78 (1H m), δ 2.19–1.73 (5H m), δ 1.59–0.90 (7H m).

Ion Spray MS: (MW=468): [M+H]=469.

EXAMPLE 49

Preparation of (3S,4aR,6S,8aR)-6-[[(2S,4S)-2-carboxy-4-(5-(3-chlorophenyl)tetrazol)-2-yl)-1-pyrrolidinyl]methyl]-decahydroisoquinoline-3-carboxylic acid

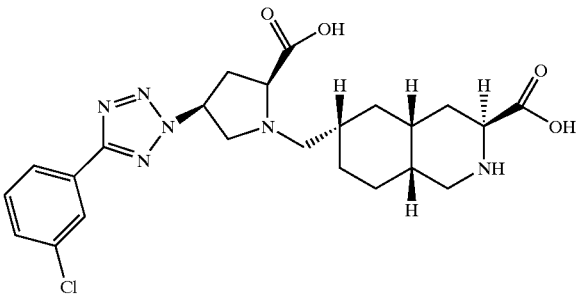

A. Preparation of Ethyl 2-methoxycarbonyl-6-[[2-ethoxycarbonyl-4-(5-(3-chlorophenyl)tetrazol-2-yl)-1-pyrrolidinyl]methyl]decahydroisoquinoline-3-carboxylate:

Following the procedure from Example 27, step A, and using 500 mg (1.1 mmol) of material from Preparation 1, step B, 288 mg (1.6 mmol) of 5-[3-chlorophenyl]-tetrazole and 419 mg (1.6 mmol) of triphenylphosphine, and DEAD (220 μL, 1.4 mmol), 178 mg (18.5%) of the title compound was prepared.

B. Following the procedure in Example 27, step B, and using 178 mg (0.30 mmol) of the compound from Example 49, step A, 141 mg (96.3%) of the title compound was prepared.

$^1$H NMR (400 MHz, D$_2$O) δ 7.80–7.60 (2H m), δ 7.4–7.2 (2H m), δ 5.81 (1H s), δ 4.53–4.40 (1H m), δ 3.90–3.78 (2H m), δ 3.30–2.75 (7H m), δ 1.90–1.20 (10H m), δ 1.00–0.90 (1H m).

Ion Spray MS: (MW=488): [M+H]=489.

EXAMPLE 50

Preparation of (3S,4aR,6S,8aR)-6-[[(2S,4S)-2-carboxy-4-(5-(methylthiomethyl)tetrazol-2-yl)-1-pyrrolidinyl]methyl]-decahydroisoquinoline-3-carboxylic acid

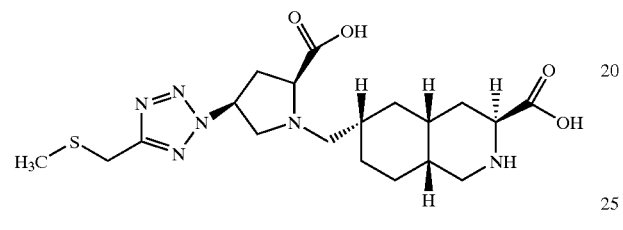

A. Preparation of Ethyl 2-methoxycarbonyl-6-[[2-ethoxycarbonyl-4-(5-(methylthiomethyl)tetrazol-2-yl)-1-pyrrolidinyl]methyl]decahydroisoquinoline-3-carboxylate:

Following the procedure from Example 27, step A, and using 500 mg (1.1 mmol) of material from Preparation 1, step B, 182 mg (1.4 mmol) of 5-[methylthiomethyl]-tetrazole and 419 mg (1.6 mmol) of triphenylphosphine, and DEAD (220 μL, 1.4 mmol), 135 mg (17.5%) of the title compound was prepared.

B. Following the procedure in Example 27, step B, and using 135 mg (0.24 mmol) of the compound from Example 50, step A, 112 mg (96.3%) of the title compound was prepared.

$^1$H NMR (400 MHz, D$_2$O) δ 5.42–5.20 (1H m), δ 4.80–4.71 (1H m), δ 4.43–4.05 (3H m), δ 3.80–3.30 (3H m), δ 3.02–2.80 (3H m), δ 2.40–0.91 (15H m).

Ion Spray MS: (MW=438): [M+H]=439.

EXAMPLE 51

Preparation of (3S,4aR,6S,8aR)-6-[[(2S,4S)-2-carboxy-4-(5-methoxymethyltetrazol-2-yl)-1-pyrrolidinyl]methyl]-decahydroisoquinoline-3-carboxylic acid

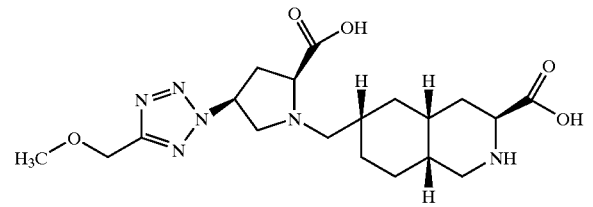

A. Preparation of Ethyl 2-methoxycarbonyl-6-[[2-ethoxycarbonyl-4-(5-methoxymethyltetrazol-2-yl)-1-pyrrolidinyl]methyl]decahydroisoquinoline-3-carboxylate:

Following the procedure from Example 27, step A, and using 500 mg (1.1 mmol) of material from Preparation 1, step B, 159 mg (1.4 mmol) of 5-[methoxymethyl]-tetrazole and 419 mg (1.6 mmol) of triphenylphosphine, and DEAD (220 μL, 1.4 mmol), 180 mg (29.7%) of the title compound was prepared.

B. Following the procedure in Example 27, step B, and using 180 mg (0.34 mmol) of the compound from Example 51, step A, 150 mg (95.6%) of the title compound was prepared.

$^1$H NMR (400 MHz, D$_2$O) δ 5.44–5.22 (1H m), δ 4.81–4.73 (1H m), δ 4.45–4.00 (3H m), δ 3.80–3.32 (6H, m), δ 3.02–2.80 (3H m), δ 2.45–0.90 (12H m).

Ion Spray MS: (MW=422): [M+H]=423.

EXAMPLE 52

Preparation of (3S,4aR,6S,8aR)-6-[[(2S,4S)-2-carboxy-4-(5-(3-phenyl-1,2,4-triazole-1-yl)tetrazol-2-yl)-1-pyrrolidinyl]methyl]-decahydroisoquinoline-3-carboxylic acid

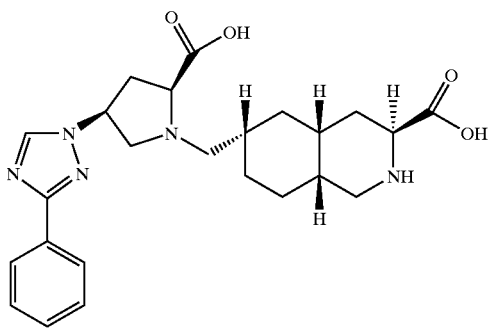

A. Preparation of Ethyl 2-methoxycarbonyl-6-[[2-ethoxycarbonyl-4-(-(3-phenyl-1,2,4-triazole-1-yl)tetrazol-2-yl)-1-pyrrolidinyl]methyl]decahydroisoquinoline-3-carboxylate:

Following the procedure from Example 27, step A, and using 504 mg (1.1 mmol) of material from Preparation 1, step B, 200 mg (1.4 mmol) of 3-phenyl-1,2,4-triazole and 420 mg (1.6 mmol) of triphenylphosphine, and DEAD (220 μL, 1.4 mmol), 137 mg (17.6%) of the title compound was prepared.

B. Following the procedure in Example 27, step B, and using 134 mg (0.23 mmol) of the compound from Example 52, step A, 10 mg (10.8%) of the title compound was prepared.

$^1$H NMR (400 MHz, D$_2$O) δ 8.50 (1H s), δ 7.80 (2H d, J=9.2 Hz), δ 7.32–7.15 (3H m), δ 5.23 (H br s), δ 4.50–4.45 (1H m), δ 4.35–4.20 (1H m), δ 4.05 (1H d, J=12.4 Hz), δ 3.92–3.85 (1H m), δ 3.650–3.58 (1H m), δ 3.15–2.95 (5H m), δ 2.20–2.10 (1H s), δ 2.05–0.90 (10H m).

Ion Spray MS: (MW=453): [M+H]=454.

EXAMPLE 53

To establish that the iGluR$_5$ receptor subtype is mediating neurogenic protein extravasation, a functional characteristic of migraine, the binding affinity of the panel compounds to the iGluR$_5$ receptor is first measured using standard methods. For example, the activity of compounds acting at the iGluR$_5$ receptor antagonists can be determined by radiolabelled ligand binding studies at the cloned and expressed human iGluR$_5$ receptor (Korczak et al., 1994, Recept. Channels 3; 41–49), and by whole cell voltage clamp electrophysiological recordings of currents in acutely isolated rat dorsal root ganglion neurons (Bleakman et al., 1996, Mol. Pharmacol. 49; 581–585). The selectivity of compounds acting at the iGluR$_5$ receptor subtype can then be determined by comparing antagonist activity at the iGluR$_5$ receptor with antagonist activity at other AMPA and kainate receptors. Methods useful for such comparison studies include: receptor-ligand binding studies and whole-cell voltage clamp electrophysiological recordings of functional activity at human GluR$_1$, GluR$_2$, GluR$_3$ and GluR$_4$ receptors Fletcher et al., 1995, Recept. Channels 3; 21–31); receptor-ligand binding studies and whole-cell voltage clamp electrophysiological recordings of functional activity at human GluR$_6$ receptors (Hoo et al., Recept. Channels 2;327–338); and whole-cell voltage clamp electrophysiological recordings of functional activity at AMPA receptors in acutely isolated cerebellar Purkinje neurons (Bleakman et al., 1996, Mol. Pharmacol. 49; 581–585) and other tissues expressing AMPA receptors (Fletcher and Lodge, 1996, Pharmacol. Ther. 70; 65–89).

iGluR$_5$ Antagonist Binding Affinity Profiles

Cell lines (HEK293 cells) stably transfected with human iGluR receptors are employed. Displacement of $^3$[H] AMPA by increasing concentrations of antagonist is measured on iGluR$_1$, iGluR$_2$, iGluR$_3$, and iGluR$_4$ expressing cells, while displacement of 3[H] kainate (KA) is measured on iGluR$_5$, iGluR$_6$, iGluR$_7$, and KA2-expressing cells. Estimated antagonist binding activity ($K_i$) in $\mu$M, for example, is determined for Compounds of Formula I. As an indicia of selectivity, the ratio of binding affinity to the iGluR$_2$ AMPA receptor subtype, versus the binding affinity to iGluR$_5$ kainate receptor subtype ($K_i$ at iGluR$_2$/$K_i$ at iGluR5) is also determined. The iGluR5 receptor antagonist compounds, as provided by the present invention, provide a $K_i$ at the iGluR5 receptor subtype of less than 5000 $\mu$M, preferably less than 500 $\mu$M, even more preferably less than 50 $\mu$M, and most preferably less than 5 $\mu$M. The preferred selective iGluR5 receptor antagonists compounds, as provided by the present invention, display a greater binding affinity (lower $K_i$) for iGluR$_5$ than that for iGluR$_2$, preferably at least 10 fold greater for iGluR$_5$ than that for iGluR$_2$, and even more preferably at least 100 fold, and most preferably at least 1000 fold than that for iGluR$_2$.

EXAMPLE 54

The following animal model may be employed to determine the ability of the compounds of Formula I or Formula II to inhibit protein extravasation, an exemplary functional assay of the neuronal mechanism of migraine.

Animal Model of Dural Protein Extravasation

A. Harlan Sprague-Dawley rats (225–325 g) or guinea pigs from Charles River Laboratories (225–325 g) are anesthetized with sodium pentobarbital intraperitoneally (65 mg/kg or 45 mg/kg respectively) and are placed in a stereotaxic frame (David Kopf Instruments) with the incisor bar set at −3.5 mm for rats or −4.0 mm for guinea pigs. Following a midline sagital scalp incision, two pairs of bilateral holes are drilled through the skull (6 mm posterially, 2.0 and 4.0 mm laterally in rats; 4 mm posteriorly and 3.2 and 5.2 mm laterally in guinea pigs, all coordinates referenced to bregma). Pairs of stainless steel stimulating electrodes, insulated except at the tips (Rhodes Medical Systems, Inc.), are lowered through the holes in both hemispheres to a depth of 9 mm (rats) or 10.5 mm (guinea pigs) from dura.

B. The femoral vein is exposed and a dose of the test compound is injected intravenously (i.v.) at a dosing volume of 1 ml/Kg or, in the alternative, test compound is administered orally (p.o) via gavage at a volume of 2.0 ml/Kg. Approximately 7 minutes post i.v. injection, a 50 mg/Kg dose of Evans Blue, a fluorescent dye, is also injected intravenously. The Evans Blue complexes with proteins in the blood and functions as a marker for protein extravasation. Exactly 10 minutes post-injection of the test compound, the left trigeminal ganglion is stimulated for 3 minutes at a current intensity of 1.0 mA (5 Hz, 4 msec duration) with a Model 273 potentiostat/galvanostat (EG&G Princeton Applied Research).

C. Fifteen minutes following stimulation, the animals are euthanized by exsanguination with 20 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

D. A fluorescence microscope (Zeiss) equipped with a grating monochromator and a spectrophotometer is used to quantify the amount of Evans Blue dye in each sample. An excitation wavelength of approximately 535 nm is utilized and the emission intensity at 600 nm is determined. The microscope is equipped with a motorized stage and also interfaced with a personal computer. This facilitates the computer-controlled movement of the stage with fluorescence measurements at 25 points (500 mm steps) on each dural sample. The mean and standard deviation of the measurements are determined by the computer.

E. The extravasation induced by the electrical stimulation of the trigeminal ganglion has an ipsilateral effect (i.e. occurs only on the side of the dura in which the trigeminal ganglion is stimulated). This allows the other (unstimulated) half of the dura to be used as a control. The ratio ("extravasation ratio") of the amount of extravasation in the dura from the stimulated side, over the amount of extravasation in the unstimulated side, is calculated. Control animals dosed with only with saline, yield an extravasation ratio of approximately 2.0 in rats and approximately 1.8 in guinea pigs. In contrast, a compound which completely prevents the extravasation in the dura from the stimulated side yields an extravasation ratio of approximately 1.0.

Dose-response curves may be generated for each of the compounds of Formula I and Formula II and the dose that inhibits the extravasation by 50% (ID$_{50}$) or 100% (ID$_{100}$) can then be approximated.

What is claimed is:

1. A compound of the formula:

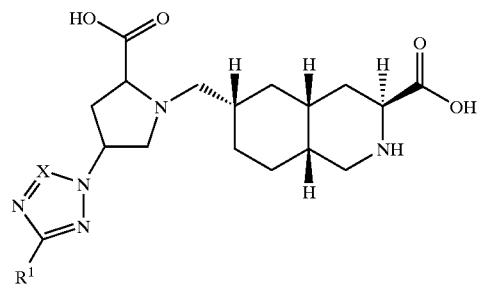

wherein,

R$^1$ represents hydrogen, (C$_1$–C$_6$)alkyl, (C$_1$–C$_6$)alkoxy, (C$_3$–C$_{10}$)cycloalkyl, SO$_2$R$^2$, SR$^2$, CH$_2$SR$^2$, (C$_1$–C$_6$) alkyl(C$_1$–C$_6$)alkoxy, aryl, (C$_1$–C$_6$)alkylaryl, (C$_1$–C$_6$) alky(substituted)aryl, or substituted aryl;

$R^2$ represents $(C_1-C_6)$alkyl; and

X represents CH or N;

or a pharmaceutically acceptable salt or prodrug thereof.

2. The compound according to claim 1 wherein X represents N.

3. The compound according to claim 2 wherein $R^1$ represents $(C_1-C_6)$alkyl, $(C_3-C_{10})$cycloalkyl, $SR^2$, or substituted aryl.

4. A compound of formula:

[chemical structure]

wherein $R^1$ represents hydrogen, $(C_1-C_6)$alkyl, $(C_1-C_6)$alkoxy, $(C_3-C_{10})$cycloalkyl, $SO_2R^2$, $SR^2$, $CH_2SR^2$, $(C_1-C_6)$alkyl$(C_1-C_6)$alkoxy, aryl, $(C_1-C_6)$alkylaryl, $(C_1-C_6)$alky(substituted)aryl, or substituted aryl;

$R^2$ represents $(C_1-C_6)$alkyl;

X represents CH or N, and $R^3$ and $R^4$ each independently represent hydrogen, $(C_1-C_{20})$alkyl, $(C_2-C_6)$alkenyl, $(C_1-C_6)$alkylaryl, $(C_1-C_6)$alkyl$(C_3-C_{10})$cycloalkyl, $(C_1-C_6)$alkyl-N,N-$C_1-C_6$ dialkylamine, $(C_1-C_6)$alkyl-pyrrolidine, $(C_1-C_6)$alkyl-piperidine, or $(C_1-C_6)$alkyl-morpholine, with the proviso that at least one of $R^3$ or $R^4$ is other than hydrogen;

or a pharmaceutically acceptable salt thereof.

5. The compound according to claim 4 wherein X represents N.

6. The compound according to claim 5 wherein $R^1$ represents $(C_1-C_6)$alkyl, $(C_3-C_{10})$cycloalkyl, $SR^2$, or substituted aryl.

7. The compound according to claim 6 wherein $R^3$ represents hydrogen and R4 represents $(C_1-C_{20})$alkyl.

8. The compound according to claim 7 wherein $R^4$ represents $(C_1-C_6)$alkyl.

9. The compound according to claim 6 wherein $R^3$ represents $(C_1-C_{20})$alkyl and $R^4$ represents hydrogen.

10. The compound according to claim 9 wherein $R^3$ represents $(C_1-C_6)$alkyl.

11. The compound according to claim 6 wherein $R^3$ and $R^4$ each independently represent $(C_1-C_{20})$alkyl.

12. The compound according to claim 11 wherein $R^3$ and $R^4$ each independently represent $(C_1-C_6)$alkyl.

13. The compound according to claim 12 wherein $R^3$ and $R^4$ each independently represent ethyl.

14. A compound of the formula:

[chemical structure]

wherein

Y represents $(CH_2)$n;

$R^5$ represents aryl, substituted aryl, $(C_1-C_6)$alkyl, $(C_1-C_6)$alkylaryl, or $CF_3$;

$R^6$ represents hydrogen, $(C_1-C_6)$alkyl, or $(C_1-C_6)$alkylaryl; and n represents 0, 1, 2, or 3;

or a pharmaceutically acceptable salt or prodrug thereof.

15. The compound according to claim 14 wherein n is 0 or 1.

16. The compound according to claim 15 wherein $R^6$ represents hydrogen or $(C_1-C_6)$alkyl.

17. The compound according to claim 16 wherein $R^5$ represents aryl, substituted aryl, or $(C_1-C_6)$alkyl.

18. The compound according to claim 17 wherein $R^6$ represents hydrogen.

19. The compound according to claim 18 wherein n represents 1 and $R^5$ represents aryl.

20. A compound which is (3S, 4aR, 6S, 8aR)-6-[[(2S, 4S)-2-carboxy-4-(N-benzylsulfonamido)-1-pyrrolidinyl]methyl]decahydroisoquinoline-3-carboxylic acid or a pharmaceutically acceptable salt or prodrug thereof.

21. A compound according to claim 20 wherein the pharmaceutically acceptable salt is the dihydrochloride salt.

22. A compound of the formula:

[chemical structure]

wherein

Y is $(CH_2)$n;

$R^3$ and $R^4$ each independently represent hydrogen, $(C_1-C_{20})$alkyl, $(C_2-C_6)$alkenyl, $(C_1-C_6)$alkylaryl, $(C_1-C_6)$alkyl$(C_3-C_{10})$cycloalkyl, $(C_1-C_6)$alkyl-N,N-$C_1-C_6$ dialkylamine, $(C_1-C_6)$alkyl-pyrrolidine, $(C_1-C_6)$alkyl-piperidine, or $(C_1-C_6)$alkyl-morpholine, with the proviso that at least one of $R^3$ or $R^4$ is other than hydrogen;

$R^5$ represents aryl, substituted aryl, $(C_1-C_6)$alkyl, $(C_1-C_6)$alkylaryl, or $CF_3$;

$R^6$ represents hydrogen, $(C_1-C_6)$alkyl, or $(C_1-C_6)$alkylaryl; and n is 0, 1, 2, 3, or a pharmaceutically acceptable salt thereof.

23. The compound according to claim 22 wherein n represents 0 or 1.

24. The compound according to claim 23 wherein R6 represents hydrogen or $(C_1-C_6)$alkyl.

25. The compound according to claim 24 wherein $R^5$ represents aryl, substituted aryl, or $(C_1-C_6)$alkyl.

26. The compound according to claim 25 wherein $R^6$ represents hydrogen.

27. The compound according to claim 26 wherein $R^3$ represent hydrogen and $R^4$ represents $(C_1-C_{20})$alkyl.

28. The compound according to claim 27 wherein $R^4$ represents $(C_1-C_6)$alkyl.

29. The compound according to claim 26 wherein $R^3$ represents $(C_1-C_{20})$alkyl and $R^4$ represents hydrogen.

30. The compound according to claim 29 wherein $R^3$ represents $(C_1-C_6)$alkyl.

31. The compound according to claim 26 wherein $R^3$ and $R^4$ each independently represent $(C_1-C_{20})$alkyl.

32. The compound according to claim 31 wherein $R^3$ and $R^4$ each independently represent $(C_1-C_6)$alkyl.

33. The compound according to claim 32 wherein $R^3$ and $R^4$ each independently represent ethyl.

34. The compound according to claim 26 wherein n represents 1 and $R^5$ represents aryl.

35. The compound according to claim 34 wherein $R^3$ represent hydrogen and $R^4$ represents $(C_1-C_{20})$alkyl.

36. The compound according to claim 35 wherein $R^4$ represents $(C_1-C_6)$alkyl.

37. The compound according to claim 34 wherein $R^3$ represents $(C_1-C_{20})$alkyl and $R^4$ represents hydrogen.

38. The compound according to claim 37 wherein $R^3$ represents $(C_1-C_6)$alkyl.

39. The compound according to claim 34 wherein $R^3$ and $R^4$ each independently represent $(C_1-C_{20})$alkyl.

40. The compound according to claim 39 wherein $R^3$ and $R^4$ each independently represent $(C_1-C_6)$alkyl.

41. The compound according to claim 40 wherein $R^3$ and $R^4$ each independently represent ethyl.

42. A compound which is Ethyl (3S, 4aR, 6S, 8aR)-6-[[(2S, 4S)-2-ethoxycarbonyl-4-(N-benzylsulfonamido)-1-pyrrolidinyl]methyl]decahydroisoquinoline-3-carboxylate or a pharmaceutically acceptable salt thereof.

43. A compound according to claim 42 wherein the pharmaceutically acceptable salt is the dihydrochloride salt.

44. A method of treating a neurological disorder or neurodegenerative disease selected from the group consisting of cerebral deficits subsequent to cardiac bypass surgery and grafting, stroke, cerebral ischemia, spinal cord lesions resulting from trauma or inflammation, perinatal hypoxia, cardiac arrest, hypoglycemic neuronal damage, tremors, drug tolerance and withdrawal, brain edema, epilepsy, depression, anxiety, post traumatic stress syndrome, tardive dyskinesia, phycosis, headache, cluster headache, tension-type headache, chronic daily headache, acute pain, chronic pain, severe pain, intractable pain, neuropathic pain, post-traumatic pain, and migraine, which comprises administering to a patient in need thereof an effective amount of a compound according to claim 1.

45. The method according to claim 44 wherein the neurological disorder is migraine.

46. A pharmaceutical composition comprising an effective amount of a compound according to claim 1, in combination with a pharmaceutically acceptable carrier, diluent, or excipient.

47. A method of treating a neurological disorder or neurodegenerative disease selected from the group consisting of cerebral deficits subsequent to cardiac bypass surgery and grafting, stroke, cerebral ischemia, spinal cord lesions resulting from trauma or inflammation, perinatal hypoxia, cardiac arrest, hypoglycemic neuronal damage, tremors, drug tolerance and withdrawal, brain edema, epilepsy, depression, anxiety, post traumatic stress syndrome, tardive dyskinesia, phycosis, headache, cluster headache, tension-type headache, chronic daily headache, acute pain, chronic pain, severe pain, intractable pain, neuropathic pain, post-traumatic pain, and migraine, which comprises administering to a patient in need thereof an effective amount of a compound according to claim 4.

48. A method of treating a neurological disorder or neurodegenerative disease selected from the group consisting of cerebral deficits subsequent to cardiac bypass surgery and grafting, stroke, cerebral ischemia, spinal cord lesions resulting from trauma or inflammation, perinatal hypoxia, cardiac arrest, hypoglycemic neuronal damage, tremors, drug tolerance and withdrawal, brain edema, epilepsy, depression, anxiety, post traumatic stress syndrome, tardive dyskinesia, phycosis, headache, cluster headache, tension-type headache, chronic daily headache, acute pain, chronic pain, severe pain, intractable pain, neuropathic pain, post-traumatic pain, and migraine, which comprises administering to a patient in need thereof an effective amount of a compound according to claim 14.

49. A method of treating a neurological disorder or neurodegenerative disease selected from the group consisting of cerebral deficits subsequent to cardiac bypass surgery and grafting, stroke, cerebral ischemia, spinal cord lesions resulting from trauma or inflammation, perinatal hypoxia, cardiac arrest, hypoglycemic neuronal damage, tremors, drug tolerance and withdrawal, brain edema, epilepsy, depression, anxiety, post traumatic stress syndrome, tardive dyskinesia, phycosis, headache, cluster headache, tension-type headache, chronic daily headache, acute pain, chronic pain, severe pain, intractable pain, neuropathic pain, post-traumatic pain, and migraine, which comprises administering to a patient in need thereof an effective amount of a compound according to claim 22.

50. A pharmaceutical composition comprising an effective amount of a compound according to claim 4 in combination with a pharmaceutically acceptable carrier, diluent, or excipient.

51. A pharmaceutical composition comprising an effective amount of a compound according to claim 14 in combination with a pharmaceutically acceptable carrier, diluent, or excipient.

52. A pharmaceutical composition comprising an effective amount of a compound according to claim 22 in combination with a pharmaceutically acceptable carrier, diluent, or excipient.

* * * * *